US006995300B2

(12) United States Patent
Myers et al.

(10) Patent No.: US 6,995,300 B2
(45) Date of Patent: *Feb. 7, 2006

(54) ISOLATION OF SU1, A STARCH DEBRANCHING ENZYME, THE PRODUCT OF THE MAIZE GENE SUGARY1

(75) Inventors: Alan M. Myers, Ames, IA (US); Martha Graham James, Des Moines, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 332 days.

This patent is subject to a terminal disclaimer.

(21) Appl. No.: 10/179,562

(22) Filed: Jun. 25, 2002

(65) Prior Publication Data

US 2005/0204425 A1    Sep. 15, 2005

Related U.S. Application Data

(63) Continuation-in-part of application No. 09/256,741, filed on Feb. 24, 1999, now Pat. No. 6,410,716, which is a continuation-in-part of application No. 08/410,784, filed on Mar. 24, 1995, now Pat. No. 5,912,413.

(51) Int. Cl.
*C12N 15/82* (2006.01)
*C12N 15/29* (2006.01)
*C12N 5/10* (2006.01)
*A01H 5/00* (2006.01)
*C12P 19/04* (2006.01)

(52) U.S. Cl. .................... 800/284; 800/278; 800/286; 435/320.1; 435/419; 536/23.2; 536/23.6; 536/24.5

(58) Field of Classification Search ............... 800/278, 800/284, 286; 435/320.1, 419; 536/23.6, 536/24.5, 23.2
See application file for complete search history.

(56) References Cited

OTHER PUBLICATIONS

Pan, David et al., "A Debranching Enzyme Deficiency in Endosperms of the Sugary-1 Mutants of Maize", Plant Physiol. 74: 324-328 (1984).
Creech, Roy G., "Carbohydrate Synthesis in Maize", Advances in Agronomy, 20: 275-311 (1968).
Preiss, Jack, "Biology and Molecular Biology of Starch Synthesis and its Regulation", Oxford Surveys of Plant Molecular and Cell Biology, 7: 59-114 (1991).
Sumner, James B. et al., "The Water-Soluble Polysaccharides of Sweet Corn", Archives of Biochemistry, 4: 7-9 (1994).

*Primary Examiner*—David T. Fox
(74) *Attorney, Agent, or Firm*—Weingarten, Schurgin, Gagnebin & Lebovici LLP

(57) ABSTRACT

SU1, a starch debranching enzyme active in maize endosperm (*Zea mays*), and the cDNA and genomic sequences encoding SU1 are disclosed. The amino acid sequence is significantly similar to that of bacterial isoamylases, enzymes that hydrolyze α-(1→6) glycosidic bonds. Amino acid sequence similarity establishes SU1 as a member of the α-amylase superfamily of starch hydrolytic enzymes. Also disclosed are antibodies reactive with the SU1 protein, methods of producing antibodies to the SU1 protein, methods of producing fusion proteins including SU1 as well as recombinant SU1 and methods of producing transgenic plants with a modified Su1 gene. The native or expressed SU1 protein can serve as a replacement for the bacterial and fungal enzymes currently used in the starch processing industry.

11 Claims, 41 Drawing Sheets

```
  1   R   L   V   T   H   S   T   R   T   H   Y   L   I   G   Q   S   Q   T   N   W                    20
  1   CGTCTCGTCACACTCCACTCGAACGCACTACTTGATCGGCCAAAGCCAAACGAACTGG                                         60
 21   A   P   S   P   P   L   P   L   P   M   A   Q   K   L   P   C   V   S   S   P                    40
 61   GCTCCCTCCGCCCCTCCACTTCCTCTCCCCATGGCGCAGAAGCTCCCCTGCGTCTCGTCGCCG                                    120
                                     NcoI
 41   R   P   L   L   A   V   P   A   G   R   W   R   A   G   V   R   G   R   P   N                    60
121   CGCCCGCTGCTCGCCGTGCCCGCGGGCCGGTGGCGCGCCGGTGCGCGGCCGTGCGGGGCCCAAT                                   180
 61   V   A   G   L   G   R   G   R   L   S   L   H   A   A   A   A   R   P   V   A                    80
181   GTGGCGGGACTGGGCCGGGGCCGGTTGTCTCTCCACGCCGCCGCGGCCCGTGGCC                                           240
 81   E   A   V   Q   A   E   E   D   D   D   D   D   E   E   V   A   E   E   R   *                   100
241   GAGGCGGTGCAGGCGGAGGAGGACGACGACGACGAGGAGGTGGCCGAGGAGAGG                                            300
101   F   A   L   G   G   A   C   R   V   L   A   G   M   P   A   P   L   G   A   T                   120
301   TTCGCGCTCGGGGGCGCGTGCCGGGTGCTGCCGGGAATGCCCGCGCCGCTCGGCGCCACC                                      360
                                                                   NarI
121   A   L   R   G   G   V   N   F   A   V   Y   S   S   G   A   S   A   A   S   L                   140
361   GCGCTCCGCGGCGGGGTGTCAACTTCGCCGTCTACTCCAGCGGTGCCTCCGCCGCGTCGCTG                                    420
                             HincII
141   S   L   F   A   P   G   D   L   K   A   D   R   V   T   E   E   V   P   L   D                   160
421   AGCCTCTTCGCTCCCGGCGACCTCAAGGCGGATAGGGTGACCGAGGAGGTGCCCCTCGAT                                      480
161   P   L   L   N   R   T   G   N   V   W   H   V   F   I   H   G   D   E   L   H                   180
481   CCCCTGCTCAACCGAACGGGAAACGTGTGGCACGTGTTCATCCACGGGGACGAGCTGCAC                                      540
                                              PmlI
```

```
                 G   M   L   C   G   Y   R   F   D   G   V   F   A   P   E   R   G   Q   Y   Y                          200
541  GGCATGCTCTGCGGATACAGGTTCGATGGCGTGTTCGCCCCTGAGCGCGGACAGTACTAC                                                         600
         SphI
                 D   V   S   N   V   V   V   D   P   Y   A   K   A   V   V   S   R   G   E   Y                          220
601  GATGTGTCCAACGTTGTGGTGGATCCATACGCTAAGGCAGTGGTAAGCCGAGGTGAATAT                                                         660
                         BamHI
                 G   V   P   A   P   G   G   S   C   W   P   Q   M   A   G   M   I   P   L   P                          240
661  GGTGTGCCTGCGCCTGGTGGTAGTTGTTGGCCTCAAATGGCTGGTATGATCCCTCTTCCC                                                         720
                 Y   N   K   F   D   W   Q   G   D   L   P   L   G   Y   H   Q   K   D   L   V                          260
721  TATAATAAGTTTGATTGGCAAGGTGACCTACCCCTTGGTTACCATCAGAAGGACCTTGTC                                                         780
                                                               KpnI
                 I   Y   E   M   H   L   R   G   F   T   K   H   N   S   K   T   K   H   P                              280
781  ATATATGAAATGCATTTGCGTGGATTCACAAAGCACAACTCAAGCACAAACACCCA                                                             840
                 G   T   Y   I   G   A   V   S   K   L   D   H   L   K   E   L   G   V   N   C                          300
841  GGAACTTACATTGGTGCTGTGTCAAAGCTTGACCATCTAAAGGAACTTGGAGTGAACTGT                                                         900
                                                       HindIII
                 I   E   L   M   P   C   H   E   F   N   E   L   E   Y   F   S   S   S   S   K                          320
901  ATAGAGCTAATGCCCTGCCATGAGTTCAATGAGCTAGAGTACTTCAGCTCCTCTTCGAAG                                                         960
                 M   N   F   W   G   Y   S   T   I   N   F   F   S   P   M   A   R   Y   S                              340
961  ATGAACTTCTGGGGATATTCCACAATAAATTTTTTCTCACCAATGGCAAGATATTCTTCA                                                        1020
                 S   G   I   R   D   S   G   C   G   A   I   N   E   F   K   A   F   V   R   E                          360
1021 AGTGGCATAAGAGACTCTGGATGTGGCGCCATAAATGAATTTAAAGCTTTTGTAAGGGAG                                                        1080
                                                                             HindIII
                 A   H   K   R   G   I   E   V   I   M   D   V   V   F   N   H   T   A   E   G                          380
1081 GCCCACAAACGGGGAATTGAGGTGATCATGGATGTTGTCTTCAATCATACAGCTGAAGGT                                                        1140
                                         BclI
```

FIG. 1C

```
 381  N  E  K  G  P  I  L  S  F  R  G  I  D  N  S  T  Y  Y  M  L                                    400
1141  AATGAGAAAGGCCCAATATTATCCTTTAGGGGATAGATAATAGTACATACTACATGCTT                                   1200
 401  A  P  K  G  E  F  Y  N  Y  S  G  C  G  N  T  F  N  C  N  H                                    420
1201  GCACCTAAGGGAGAGTTTTATAATTATTCGGTTGTGTGGAAATACCTTCAATTGTAATCAT                                   1260
 421  P  V  V  R  E  F  I  V  D  C  L  R  Y  W  V  T  E  M  H  V                                    440
1261  CCTGTAGTCCGTGAATTTATAGTGGATTGCTTGAGATACTGGGTAACAGAAATGCATGTT                                   1320
 441  D  G  F  R  F  D  L  A  S  I  L  T  R  G  C  S  L  W  D  P                                    460
1321  GATGGTTTTCGTTTTGACCTTGCATCTATACTGACCAGAGGATGCAGTCTATGGGATCCA                                   1380
                                                                BamHI
 461  V  N  V  Y  G  S  P  M  E  G  D  M  I  T  T  G  T  P  L  V                                    480
1381  GTTAATGTGTATGGAAGTCCAATGGAAGGTGACATGATTACGACAGGGACACCTCTTGTT                                   1440
 481  A  P  P  L  I  D  M  I  S  N  D  P  I  L  G  N  V  K  L  I                                    500
1441  GCCCCACCACTTATTGACATGATTAGCAATGACCCAATTCTTGGAAATGTCAAGCTCATT                                   1500
 501  A  E  A  W  D  A  G  G  L  Y  Q  E  G  Q  F  P  H  W  N  V                                    520
1501  GCTGAAGCATGGGATGCAGGAGGTCTCTATCAAGAAGGTCAGTTTCCTCACTGGAACGTT                                   1560
 521  W  S  E  W  N  G  K  Y  R  D  T  V  R  Q  F  I  K  G  T  D                                    540
1561  TGGTCAGAGTGGAATGGGAAATATCGCGATACCGTGCGTCAGTTCATCAAAGGCACAGAT                                   1620
 541  G  F  A  G  A  F  E  C  L  C  G  S  P  Q  L  Y  Q  A  G                                       560
1621  GGATTTGCTGGTGCTTTTGAATGCCTATGTGGAAGTCCACAGTTATACCAGGCAGGG                                      1680
 561  G  R  K  P  W  H  S  I  G  F  V  C  A  H  D  G  F  T  L  A                                    580
1681  GGGAGGAAGCCTTGGCACAGTATCGGCTTTGTATGTGCACACGATGGATTTACACTGGCT                                   1740
```

FIG. 1D

| Pos | Sequence | Pos |
|---|---|---|
| 581 | D L V T Y N S K Y N L S N G E D F R D G | 600 |
| 1741 | GATTTGGTCACATACAATAGCAAGTACAACTTGTCAAATGGTGAGGACTTCAGAGATGGG | 1800 |
| 601 | E N H N L S W N C G E E G E F A S L S V | 620 |
| 1801 | GAAAATCATAATCTTAGCTGGAATTGTGGGGAGGAGAGAATTTGCAAGTCTGTCAGTC | 1860 |
| 621 | R R L R K R Q M R N F F V C L M V S Q G | 640 |
| 1861 | CGAAGATTAAGGAAGAGGCAAATGCGCAATTTCTTTGTTTGTCTTTATGGTTTCTCAGGGA | 1920 |
| 641 | V P M F Y M G D E Y G H T K G G N N T | 660 |
| 1921 | GTTCCAATGTTCTACATGGGCGATGAATATGGTCACACAAAGGAGGAACAACAATACG | 1980 |
| 661 | Y C H D H Y V N Y F R W D K K E E Q S | 680 |
| 1981 | TACTGCCATGACCATTATGTCAATTATTCCGTTGGGATAAGAAGGAAGAACAATCCTCT | 2040 |
| 681 | D L Y R F C R L M T E F R K E C E S L G | 700 |
| 2041 | GATTTGTACAGATTCTGCCGTCTCATGACCGAATTCCGCAAAGAATGTGAATCTCTTGGC | 2100 |
|   |  EcoRI |  |
| 701 | L E D F P T S E R L K W H G H Q P G K P | 720 |
| 2101 | CTTGAGGACTTCCCGACTTCAGAACGGTTGAAATGCACGGTCATCAGCCCGGGAAGCCT | 2160 |
| 721 | D W S E A S R F V A F T M K D E T K G E | 740 |
| 2161 | GACTGGTCAGAGGCAAGCCGATTCGTTGCCTTCACCATGAAGGACGAAACCAAAGGCGAG | 2220 |
| 741 | I Y V A F N T S H L P V V V G L P E R S | 760 |
| 2221 | ATCTACGTGGCCTTCAACACCAGTCACCTTCCGGTGGTTGTTGGGCTTCCAGAGCGCTCT | 2280 |
|   | BglII |  |
| 761 | G F R W E P V V D T G K E A P Y D F L T | 780 |
| 2281 | GGGTTCCGATGGGAGCCGGTGGTGGACACCGGCAAGGAGGCACCATATGACTTCCTCACC | 2340 |

```
781  D   G   L   P   D   D   R   A   V   T   V   V   Y   Q   F   S   H   F   L   N   S   N
2341 GATGGCCTGCCAGATCGTGCTGTCACCGTCTACCAGTTCTCTCATTCCTCAACTCCAAT                                    2400

801  L   Y   P   M   L   S   Y   S   S   I   I   L   V   L   R   P   D   V   *
2401 CTCTATCCTATGCTCAGCTACTCCTCCATCATCCTTGTATTGCGCCCTGATGTCTGAAAG                                    2460

2461 AAGCAGATACAATAGAGTATACTATAGCGGTTGTTCTCTAGGCTGTAGCATGCAGTGGAA                                    2520
                                                              SphI

2521 ACTGGAAAAATGTTGGGGTTGCTCTGTGTCGGTAGTTTACATGCGCATGTCGGTATGTGT                                    2580

2581 ACATAAAGCTGGTGGATCTCAGTTCTCAGATGGACTCGAGACGGCAAAACCATTGCCAG                                     2640
                                            XhoI

2641 TTGGCTGGTTCTCTGAAGTTTTGTTTGGTGTAAAGAAATGGTGGTCCATCATCTACTCTT                                    2700

2701 TTTTTTTTTTTT  2712
```

*FIG. 1E*

1 CACCGAACTA TCATATATAT AGGTCTGCAT GATATTGATG GTTGCAATGT AGTGGTAAAA

61 CAGGTAGATT AAAATAACAA AATGTATATG TATAGCCCAG GATCACCAAT GAATTACAAA

121 ATCTTTTTTC ATAACAATAT AACACATTTA TATATAAGTT ATCATGATAT TAATATGTTC

181 CCATTGCAAC GCACGGGAAC TAACCTAGTA ATTAATTAAT TTATTACCTC CTTTCGACGA

241 ACCAGCCGGC ACCAAAAGAT GGATCACCGT GCACGGAGCG TGCGTCCGTT GCGGGAAACG

301 ACGGGGATCT AGGCGACGCC GTGACGGTGA TGCTCCCGTT CACGTTTCGC GGCTTTCGCT

361 GCACCCCTTT GATTCACGGT GGCCCCACAG AAAAGCCCAT GTCCACGGGG CCCACTCCCG

421 GGTCCGGACA CGCGCCGAGG GAGAGGGGCT CCCAGATTTT CTAGGGACTG CTACCTTCTT

481 TTTTTAGATA AATAATAGAC CAAAATCCGG TTTTAGGGCA TGTTTGGTTC CCTACCTAAC

541 TTGCCACACT TTGCCTAACT TTTCTGCCTA AGGTTAGTTC TTCAATTTGA ACGACTAACC

601 TTAGGCAAAG TGTGGCGTAT TTAGCCACGA ACCAAACAGG CCCTTACTAT TTCGAGGGTA

661 AGCGCAAATT CACATAACTT AAAAAAAAAT CTAAACATC TCACAAAACA TAACAAAATT

721 ATAAGTCTAG AAGACTTAAT AACTCCCCTA CTCATCAGCG ACTCAAACTC ACTTTAAAAA

FIG. 2A

```
781  ACGGCTCATT ACAACTCAAT CCTATTTAAA AACCTCCAAC CCTGATAAGC AAAAAACTGC

841  GTGGCCACCA ACTTCAGATA ACGACAGACT TTAATTAAAA GATCAGCTGC TTCTTCACTT

901  TTCTGTAGCT GCGTCTAGAG TCTGAGCCAA TGAGTTCCTC CAAATAAAAC CTGCAAATAA

961  GTCAACATAT GTACTTTGTT AAATATTAAT TCATTTCTAC TTATTCAAAT AGCACAGCAC

1021 ATGCTGAGAC ACCATAATAA TCAAATTCTT AGTATTTAGA TCCATCTCAT CAACCAACTC

1081 CAAAGATATG TTTGACAGTT CTTAGTATTT AGGGACTGCT GCCGAGTACG TTCCTTCAGA

1141 TCCTCTTTGG TTCTTCCTTT TCTATTTTAT TTATATTGTC ACTTTACTAG ACCATAGTAA

1201 GAGAGAATTC TCTTTTGAGT TAATTAACCA CCCACACCGT ACAAATTGAG CAAGCCTTTG

1261 TTATCTCCAC ATACATGTAT ATTAATATAA GATACATATA TCTCGTTTTT TAAAGAAATA

1321 TCGCATTGGG TTTATTATTA TTTTAAGACT AGTTTGTAAA CTCTATTTTT CTGAGAAATT

1381 CCTATTTTTC AAGAGAAAAT AAACTAATTT ATTTGAAAAA ATGTAAAACT TTTGATAAAA

1441 TAGGATTGTC AAACTAGACC TTATTATATG TATATGTATA TGTATAAAGT ATCACTGTGA

1501 AAAGTATGAA AAAGTTTAG TTCTTTTCTT TTGGTGAATA TAAGAGTATA AATAATAAAA
```

*FIG. 2B*

```
1561 AGTGGAATAG TATAGTGCCT GAAAAGCGGC AACTAGATCG TGTTTGCCAG TACGCGGGCC

1621 CCACAGAAAA AGCCCACGTC CGCCTCCCGC TGCGAAAAAA CGACACGGGC CGAGTGGACG

1681 ACGGTGGCCG GACGCAGACG CAGACGCTTC CGGCTGTGAA AAACGCACG CTCCGACCCC

1741 GCCGTCCGCC GATCCGAGGC TCCGGCCCCA CTCTGTCAGC GTCACTGCGT GAGCGAGCGG

1801 GCGGGTGCGT GATCCGGACC CGCCCCTCCT CACACCGTCG CGCACGGGAG CCAAGACGAC

1861 GCCGCGCTCC GTCGCATCCA CCTCGTCTCG TCACACACTC CACTCGAACG CACTACTTGA

1921 TCGGCCAAAG CCAAACGAAC TGGGCTCCCT CCCCTCCACT TCCTCTCCCC ATGGCGCAGC

1981 AGCTCCCCTG CGTCTCGTCG CCGCGCCCGC TGCTCGCCGT GCCCGCGGGC CGGTGGCGCG

2041 CCGGCGTGCG GGGCCGGCCC AATGTGGCGG GACTGGGGCG GGGCGGCTG TCTCTCCACG

2101 CCGCCGCCGC GCGGCCCGTG GCCGAGGCGG TGCAGGCGGA GGAGGACGAC GACGACGACG

2161 ACGAGGAGGT GGCCGAGGAG AGGTTCGCGC TGGGCGGCGC GTGCCGGGTG CTCGCGGGAA

2221 TGCCCGCGCC GCTCGGCGCC ACCGCGCTCC GCGGCGGTGT CAACTTCGCC GTCTACTCCA

2281 GCGGTGCCTC CGCCGCGTCG CTGTGCCTCT TCGCTCCCGG CGACCTCAAG GCGGTGAGCA
```

*FIG. 2C*

```
2341 TCCCCCACCC CTAGTCTTTG ATGAATGCAA TTTCTGCAAC CGGTGCTCGG ATCCTTCTGT

2401 GTCGTTCTTC TTCTCTTTTG GAATTTGAAT GGAAGGGAAG TCGGCTTACT AACTTACTCC

2461 TCTATTTCTC TCTCTCTCGA ATAACTTGCT TCTCGATGCT GTACGCTAAT TGTTGGCTTC

2521 ATACGATACG CCGGTGCTGA AATGGACTGA GTTCTCTGTA TTCCTGGTAT GATGCAGGAT

2581 AGGGTGACCG AGGAGGTGCC CCTCGATCCC CTGCTCAACC GAACGGGAAA CGTGTGGCAC

2641 GTGTTCATCC ACGGGGACCA GCTGCACGGC ATGCTCTACG GATACAGGTT CGATGGCGTG

2701 TTCGCCCCTG AGCGCGGACA GTACTACGAT GTGTCCAACG TTGTGGTGGA TCCATACGCT

2761 AAGGTGACGG GCTGTTGTCT TTACTTTGGC TATGCGTGTG AGCTGTGACA CACTCAGAAA

2821 CTGATTGCTG GGTGCTTGCT CATGTTTTAG TTGTTTACTT CTTCTTGTTG TTGTTTTCTC

2881 TAGGCAGGCA GTGGTAAGCC GAGGTGAATA TGGTGTGCCT GCGCCTGGTG GTAGTTGTTG

2941 GCCTCAAATG GCTGGTATGA TCCCTCTTCC CTATAATAAG GTAAGCCAGA ACTACTCTCG

3001 CTCACACTAC CTTCCTGTTT GCTTTCATGC TGTATCCTTC TCTTCCAGTT TTATGATCTC

3061 CCCATGTCTG ACTCACTCAC GATTAAACAA TAAAAAGAAA CCACCGCATA TATTTGGCTC
```

*FIG. 2D*

```
3121 ATTGATGCAT TTGAAAAGCT CCGCATGAAC TAACTGAACA AAGCGCCTAG ATATCAACTG

3181 TAGGTTAGGA CTCATTGGCT TCTGCTTACT TAGTTTCTGC TTTGCCAGGT TCAAATGGAG

3241 TCGAAGTTAT ATTTCACGTG CTATTCATGT TGTCTTGTTA TTTCATTTCG TATGATAAGG

3301 GTTTGCATTT GCAGTTTGAT TGGCAAGGTG ACCTACCCCT TGGGTACCAT CAGAAGGACC

3361 TTGTCATATA TGAAATGCAT TTGCGTGGAT TCACAAAGCA CAACTCAAGC AAGACAAAAC

3421 ACCCAGGAAC TTACATTGGT GCTGTGTCAA AGCTTGACCA TCTAAAGGTA CTGTTACGAA

3481 CAGACTAGCT ATAAGTCTGC GAAAGTGTCC TCATGCATTT GTTTAGGTTT TGCAACTATG

3541 CCAAGTAATG CTGCCCTAGT CTATTAGTTC ATAGGCATAA ACACAGATTT TACTTTGTGC

3601 TTACATAAAT GTTTTGCTC AGTAAACTTG TCAGTGGTAT TGGTCGTCTT AGACTTTTTG

3661 GCATGTGTTT GTTGTTGGAA TATAATATAA GTGAATTGTC AACCTTCTCC TATCAGCTTA

3721 AGCTTTTGGA TAGAAAGAAT TGGTTGGTGC ATGTAACTTA ATATGGTATT AAAGACAGAG

3781 GTCATGAATT CGAATCCTGA CTAGCACAAT TAAATAAAAC CCAAAAGCTT AAGCTTATAG

3841 GAAGAGATGG ATAATTCACT TATATTATAT TCTAACATTT ATGACTAAAC TCTTTGTTTG
```

*FIG. 2E*

```
3901 ACCTGCATAA ACTCCCTTCA CAGGAACTTG GAGTGAACTG TATAGAGCTA ATGCCCTGCC

3961 ATGAGTTCAA TGAGCTAGAG TACTTCAGCT CCTCTTCGAA GTATGTGGAT TTGGATTACA

4021 GTATATAGAT GCCATCAGTT TTATAGGACT CTGGAACTGA TATCTTTTTG TTTCATTGAG

4081 CATGATCGTA TATGACCTTT TCGTTCTATT TTCCATGATA TTTCCCCCAT TTCCAGATTT

4141 GCTAGTGTGA TCTCCAATTT TGTGCCTTAC CCTTATAGCT TGATCACAAC TGACTTATAT

4201 TCATATATTG ACACATTATT TCATATAATT GTTCATCCTT GTGCCAGGAT GAACTTCTGG

4261 GGATATTCCA CAATAAATTT TTTCTCACCA ATGGCAAGAT ATTCTTCAAG TGGCATAAGA

4321 GACTCTGGAT GTGGTGCCAT AAATGAATTT AAAGCTTTTG TAAGGGAGGC CCACAAACGG

4381 GGAATTGAGG TAACCAAGCC AATTTAAGTT AATGGCTGAA TGCTAACCGA AATAAGAGCT

4441 TCCTTATATC ATTTTTGACA TGGAGATATG TCACTATTAG GTGATCATGG ATGTTGTCTT

4501 CAATCATACA GCTGAAGGTA ATGAGAAAGG CCCAATATTA TCCTTTAGGG GGATAGATAA

4561 TAGTACATAC TACATGCTTG CACCTAAGGT GAGATACATT ATTCATCTTG TAATCGTTCT

4621 TTCATGGACC ACAAAGTATT TATGTATTCC ATTTCATAGA TTCACGTCTA TATAACAAGC
```

*FIG. 2F*

4681 TATTTGAAGA GCATTTATTT GTGCAGGGAG AGTTTTATAA TTATTCTGGT TGTGGAAATA

4741 CCTTCAATTG TAATCATCCT GTAGTCCGTG AATTTATAGT GGATTGCTTG AGGTACAAAT

4801 CTGTATATAA CTTCTGTTAA ATTGCTCCTA ATTTCCTTCT GCCGCTTGTC ATTCTATTGG

4861 ATGATGCAAG TTTTTGAGGG ATGGATAGCA ATGTTTATGC TTTGCTGCCT GAATATATAA

4921 GCATTTTAAA TTTCTAGTAT TCAAACAAAA CAAAGAAACA AGTTTTCTTT AATTGATATT

4981 TCGTCATTGA CTATCAGTGT TTAAGCTATA TATTTGTTAA GATAAATTGT TTATGCACTA

5041 ATATTTGAGT TTGATGTTGC AGATACTGGG TAACAGAAAT GCATGTTGAT GGTTTTCGTT

5101 TTGACCTTGC ATCTATACTG ACCAGAGGAT GCAGGTAAAA TGTTATTCTT ATTTTCTCCT

5161 TATTTGTCT TTTTAGGCAT TCTTAAGCCA ACCTTTCCTT TACCAGTCTA TGGGATCCAG

5221 TTAATGTGTA TGGAAGTCCA ATGGAAGGTG ACATGATTAC GACAGGGACA CCTCTTGTTG

5281 CCCCACCACT TATTGACATG ATTAGCAATG ACCCAATTCT TGGAAATGTC AAGGTAGCTG

5341 TTATATTTTA TACTTATGTT TTATTTTTTT TCTCCAAAAG CGCAGGAGAA CTGCGCCCCG

5401 TTATATATTA AGAAAAGAGA AACAAAGGTC TATAGAAGAC CCAGATACAA GACTCTCCTT

FIG. 2G

```
5461  ACGGAGGCCA GAAACAAGCA TACAAAAAAC TGTCCATAAA GACACTAACC CTCCCAACAT

5521  CTGCCCCTAA GCATTAGGAA GCGGAGCCAA CTACATTCGG GGCCCTAGCC AGGTCTAGTG

5581  AGCCTAGATT TTTAGCTCCA GCCATAACCC AACATACAAG TTCATCTAAG AAGCTTCTCT

5641  GTAGTCTTGC TAGTGAAGGA GATTCCACAT TGAAGATTAC TTTGTTGCGG TGAAGCCATA

5701  CACACCACGC CCCAGAATG  ATGACACTGT TGAGCCCCCT TTTTCCTACT TTTGTGCCCT

5761  CTAATAACCA GACGTCTCCA CCACTCCGCG AAAGAGGTTC ATCAACAGCA GGAGTAAGGT

5821  GGCCCAAGCT GAAAGGAGAT AAAATACTGA ACCAAAATTG ACGGGTAAAG ATGCATGAGG

5881  TTAGGAGGTA CTGAATTGTT TCCAGTTGTT GATCACATAA GGAGCAAGCA TCTGGATGTG

5941  GCAAACCTCT CTTTTCTAAC CTGTCAGCGG TCCAACACCT ATTCCTCATA GCCAACCACA

6001  GGAAGAATTT GCATTTCGGA GGAGCCCATG TCTTCCAAAG CCTTTTCCAT GGCTCAAAGG

6061  TGGTTGAACC TGAGAATAAG ATTTTTCAAC AAGATTTAGA CGAGAAATTC CCTGAGATCT

6121  CATTCCTCCA CCTGTGCTGA TCAGGAACTT GGGATAATTC AACCCCCTCA CTGAATCCCA

6181  TAACAGCAGG TACTGCTGCA GCCCAGCCAG CGAGAGAGGT GCTTTAATAT CCCTAACCCA
```

*FIG. 2H*

```
6241 CTGCCAATTT TCAAGGGCTC GAGCCACAGT TCTTGAATAT AGAAATCTTT TGCCCACCTT

6301 AGCTACCACC TCAGGGGCAA AATCCCTGAT CGCAGCCCCA TTTAGCCATC TATCAGTCCA

6361 GAAAAGAGTG CTGGTGCCAT TCCCAACCAT AGAAATCAGA GAATCTGAAA ACAGATTCTT

6421 GACATGCTGC TGTATAGGAA GCTTCAGTCC CTGCCAAGGC CTGTTTGGGT CCATTTTTTT

6481 CCAACCATAA CCATTTTGAT TGAAAAGCCC AGCTCATGAA TTGCAGATTA GGGATTTCCC

6541 AAGCCCCCCA AGATCAATAG GCCTTGTAAC AATATCTCAA GAAACCAGAC AGCTGCCTCC

6601 ATTAGCCTCT TTCCTTCTCT TCCAAATAAA CCCCTTCTA ATTTGTCTA TAGCTTTAAT

6661 CATCCAATTG GATATTCATT GCAATAAGAA GATAGACTGG GATAGCCGAA GGCACATATC

6721 GCACAAGAGC TATTCTACCA GCAAGGTTAA GAAGATGTGC TTTCCAATTT GCAATAAGAA

6781 GGTTATTTGG TTGATTATGA TTCTTAATAC TTATGTTTTA TCATCTGCAC TAACTGAAGA

6841 TTCAAAGCCA TTTTGTGGTT TTGGATACGT GTACACATGC TATGTAACTA ATCTCAGTTA

6901 CCATGTGCTT GATGCTTTTG GGTAATATAT GAACCTGATT GGCTGTTAAA TATGCAGAAC

6961 AGTATATATA ATAATCGACT GTATCAACAT ATTGTAGTTT CTTGGTTTTT GTTCTCACTA
```

*FIG. 2I*

7021 CTTCCTCCAT TGTATTTATA GCTCATTGCT GAAGCATGGG ATGCAGGAGG TCTCTATCAA

7081 GTTGGTCAGT TTCCTCACTG GAACGTTTGG TCAGAGTGGA ATGGAAAGGT AAGATACTTT

7141 CAGAGACTTC AAAGTCTTTT TGCTACTTGG TACTTTCTAA ATAACAAATG AAGCCTTGTC

7201 AAATACAGAA TGTAAGTTTC AACAGATATA TTTAAATAGA TGAGTGCTTC TATCTACCTG

7261 TGAATTGTTG CAGGGATCTA AAACTGTTTA AAATTCTAAT GTTAGTTTCT TCTAGAGGCA

7321 AATCGGTAAT TTGGTCTGGT AAGTGGATAC AGTTTGGAAT AATGGATGGA ACCAGAATCT

7381 ACGTTCAGGC CCAACTATCA AACAGACTCA GGGCTGTTTG GGGCAAGTT CCAGTTCCAG

7441 TTTTCAAGCT TCTGAAGAAG CTGGCTCCAA GGAACCTGAG CCTAGGATAC TTGGATCTCA

7501 TCATTATGTT TTTTGTTCTA GAGAAGCTGG GTTCAGAAAG GCCAACACTT AGGACTTCCC

7561 AGCCCAACTG TTTTTATGTG GGTTGAGCAG AGAAGCCCAG CTAGACAGAA AACACAAATA

7621 ACTGCATTTG TTGGACTTAT AGAATTTTAA AATTATAAAC ACAAGAATGA TTTTGAGAT

7681 ATACTTCACA GGCCAACACT TAGGAGTATG TTTCAAACAA TAGCCTCACT GACAACATTA

7741 GGTAAGTGCA TCTTTGATCT TTATCAGAGC ATGATGCTGA TGAAGTTTTG ATAATTACCA

*FIG. 2J*

```
7801 TATGATCTTT TGCATCCTTC TTCAGCTAAA CCAACAGCTT CCAACTTTTT GTTCTCTATA

7861 GTTGTTTCAC CAAAGTACTA ACTTGCTTAG TTGTTTTCTC AGTATCGCGA TACCGTGCGT

7921 CAGTTCATCA AAGGCACAGA TGGATTTGCT GGTGCTTTTG CTGAATGCCT ATGTGGAAGT

7981 CCACAGTTAT ACCAGGTAAT GTAGCATAAG TACCCATCAA TGAGCACGGT GCTACATGAC

8041 CTGAACAGAA ACTTTTGAAG GAACTGGGTG ATAGTGTTAC AGATAAACAG AAATAACATA

8101 ATATGACAAT CTAGCATATA TTTCAGCCTA GAAGTTTAAC ACAAGTTCCA TTCTATGTAG

8161 TAGTATAACC TTTAGGATCC ATCTGCAAGT GAGAGATCAC ATTCTTTTCT TGAGTGTCT

8221 AATGGACCTC TTCAAGCCAT TGAAAACTCC TACTATATAT GTATTTGTT GGATGAGAAG

8281 CCGCATGAAT AAATACTATC TTCTGTGAAC TGATGAAAGC ATTAACAATG AATTGCCGAA

8341 TACTCCATGT ATTGTATGCA ATTAGGTGGA TTAGTGTTTA TCTACAAATA ATAGTTTGGT

8401 ATTGATAAGT ACATGCCTTT TATTATCAGG CAGGGGGGAG GAAGCCTTGG CACAGTATCA

8461 ACTTTGTATG TGCACACGAT GGATTTACAC TGGCTGATTT GGTCACATAC AATAGCAAGT

8521 ACAACTTGTC AAATGGTGAG GACAACAGAG ATGGGGAAAA TCATAATCTT AGCTGGAATT
```

FIG. 2K

```
8581 GTGGGGAGGT AATTTGAAAT CTCATGCTTT TATCTCTTGT AGGCTTTTTA TGTTAGTCAA

8641 ATGTCTGTCA AATGACTTGT CATAGTTTTC TAGCCATGAG TACCAAACTG GTTCACCTA

8701 AACAGGCTAT ATAGTTTGTA CACGTGCATT TCCAGCTAAA TTTATGTGGC AAGTATATAC

8761 AGATCATCTC TATAGTGTAG CGCACTTTAG AGTTTCATTT GAATAATGCA GGAAGGAGAA

8821 TTTGCAAGTC TGTCAGTCCG AAGATTAAGG AAGAGGCAAA TGCGCAATTT CTTTGTTTGT

8881 CTTATGGTTT CTCAGGTAAG AATTAGTATC TGATGTTTTA AGTTTTTTAT GGATTGTGCT

8941 TTCAGGTCCC TGTTTGTTCA GGGTAGAACT CAAGGTTGCA TTTGCAGTCA GTGGTATGCT

9001 GGAATATGCA TCATTGGTTC AGTCCTTGAG TTTAGTCACT TGATGAGGGT TACTACTTGC

9061 TAAGTTGTGT TGAGGATCTG TGTTTTCCAA AAGATTATGC CATGTTGCAT TGAATATCCA

9121 ACTAGCTGTA TTTGTACCTG AAGAAACATA TTTATTTAAA CAAAAATTAC TGTAAACATC

9181 ATTTATTTGA CAAGGTTTCA GTCTTTCCAT GCATCCTAAT ATAGGGGTAA GGTTAAAGTG

9241 GATCTGAAGT CACATTGTTA TTTTTTGTAT TGATCTACTA CTACCTATCA ATTGTTTTCA

9301 TTTTCTAAAT TTTTAGGGAG TTCCAATGTT CTACATGGGC GATGAATATG GTCACACAAA
```

FIG. 2L

```
9361  GGGAGGGAAC AACAATACGT ACTGCCATGA CCATTATGTC AGTCCGATGC CAACACATAT

9421  TAACACATTG TTTTAATCAA TTTCTTTGAC ATTCTTGTAA TCTTCTAGCC TTTTATTTTG

9481  GTTGTGCAGG TCAACTATTT CCGTTGGGAT AAGAAGGAAG AACAATCCTC TGATTTGTAC

9541  AGATTCTGCC GTCTCATGAC CAAATTCCGC AAGTAATACT CTTCCCGCCA AATATTTCCG

9601  TGCTATACCG ATGATGGTTC ATCTGTTCAC CAAATGGCGA GATCTGTACA GTTTACGTTG

9661  TCATACTGTC TATTCATGTT CTTTTGGTGT GCAATACAGG GAATGTGAAT CTCTTGGCCT

9721  TGAGGACTTC CCGACTTCAG AACGGTTGAA ATGGCACGGT CATCAGCCCG GGAAGCCTGA

9781  CTGGTCAGAG GCAAGCCGAT TCGTTGCCTT CACCATGGTA CTGACATAAC ACCTACCACC

9841  ATCATCACTA GTCATTTCAA GAATCATTTT TCTACCATTA AGTAATCAGA AGATCAAAAA

9901  AGGAGTGCTG ATGGTTTCTA TGTATCTGTT ACTGCAGAAG GACGAAACCA AAGGCGAGAT

9961  CTACGTGGCC TTCAACACCA GTCACCTTCC GGTGGTTGTC GGGCTTCCAG AGCGCTCTGG

10021 GTTCCGATGG GAGCCGGTGG TGGACACCGG CAAGGAGGCA CCATATGACT TCCTCACCGA

10081 TGGCCTACCA GATCGTGCTG TCACCGTCTA CCAGTTCTCT CATTTCCTCA ACTCCAATCT
```

FIG. 2M

```
10141 CTATCCTATG CTCAGCTACT CCTCCATCAT CCTTGTATTG CGCCCTGATG TCTGAAAGAA

10201 GCGGATACAA TAGAGTATAC TGTAGCGGTT GTTCTCTAGG CTGTAGCATG CAGTGGAAAC

10261 TGGAAAATGT TGGGGTTGCT CTGTTGTCGG TAGTTTACAT GCGCATGTCG GTATGTGTAG

10321 CTAAAGCTGG TGGATCTCAG TTCTCAGATC GGACTCGAGC CGGGGAAAAC CATTGCCCGG

10381 TTGGCTGGTT CTCTGAAGTT GTGTTTGGTG TAAAGAAATG GTGGTCCATC ATCTACTCAA

10441 TTTTTTTCTC TTTTTTTAAT GAAATAAATT GATTCAAAAT TAACTCATTC CTCAACTTAA

10501 TAATTAGTAT ATACACGAGG AATAAATTAA TTCTATCAAA TTTATGAAAT GAAATCCAAC

10561 ATTATTCGAA GAAGAATCGA CAACTACTAA CACGGCACTG CTCCCGGAGA AAGAGGAAAA

10621 CCTGGCAAAT GGATTACGAT GTGAGGGTCG CTAAAGTAAA GAGTACGACA AAACTTTCAT

10681 AGCATAAGCT CAGAACTTAC GTTGTCATTA TAGGCGATAC TGTCCTACCA ACTCCGCCGC

10741 CTGCGCTACA AACTCCAGGT ATCCTTGGTC ATGGTCACAT ACCTTCGAAA GGTATGGAGC

10801 ATTGTACCCA CGTAAACAAC CCATAGTATT TTTAACCAAA GTACGTTGGC AAGAACGAAG

10861 CACAGTACCA CACGCTTGTC AACAGAAGAC CCTTTTTACC TTTCTACACA CTCTCCAAAG
```

FIG. 2N

```
10921 GAGATCCTTG TAAGAGGAAT CTTCCTTGAG CTATAAAGG AAGGGTTGGT CTTCTCTATT

10981 CAGATGAACA CACACTCCGA TCCACGCACG CACTACTCAC ACCAGAGACT TGGGACGCTT

11041 CCCTCTCTCG CCTGCTTGCA CCTCGTACTA CGAATAATTT GGTGTTGGTA GTGTAGCCAC

11101 CGAAGACTAA GTAGGGATAT TCGGCCGAAC CAATATAATT CTGCGTCCAC ATCACAACCC

11161 CCGAGCCTAC GCGCCCTACA AATTTATTCG TCGGTACTTA CTCAAACTCG CCACTAAGGC

11221 CAGGGTTCGA GCCCAATATC TAACGCTCCC ATACCATTGT TAGGTGTCTA GGACATTGGC

11281 TCTGTTGGGG GCCTTTCTCT TTCGAAGGTC CTCAAAAGTG CGACTAACCA TTTGTTTTCA

11341 GTATGATATA TATTATTACA GGAAGCTTCA GCTTTGGGAT GAAAGTTCTC TCATGATAAA

11401 GGCATGTGAT ATGAATATAC AACCCGAAGG TGACATGGAT GGACGCCAAG CTGTGGCTCA

11461 AGGAGCTTCA GCTTGGATGG AAGACAAACC GACCTAAGGG GGAAAAGACT ACTTAGTCCT

11521 TGATAACTTG TATTATAACT AAGAGTAAAT GCCAGGGGTA TGAATGTAAT CTTATCCGGG

11581 CTGCATCCTG TGCCTATAAA TAGATGAACA GTATCACTGT ACTGTTCACG CTGGATTGTA

11641 ATCTCTCTCT CGCGTCATCT TTGCATTCTC ACCTTCTGGC GAACTGAAGG TACATTGTTT
```

*FIG. 20*

11701 TATAAATATC ATTAATGTTA TCCTATTTGT AAATATGAAT ATAATTGAAT GGTTTTGTTC

11761 TTTCCCCCCT TATTTGTAT

*FIG. 3B* silver stained
SDS-PAGE anti-SU1
immunoblot

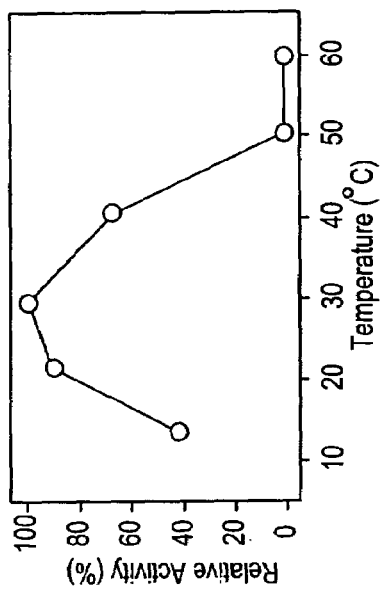
FIG. 15B
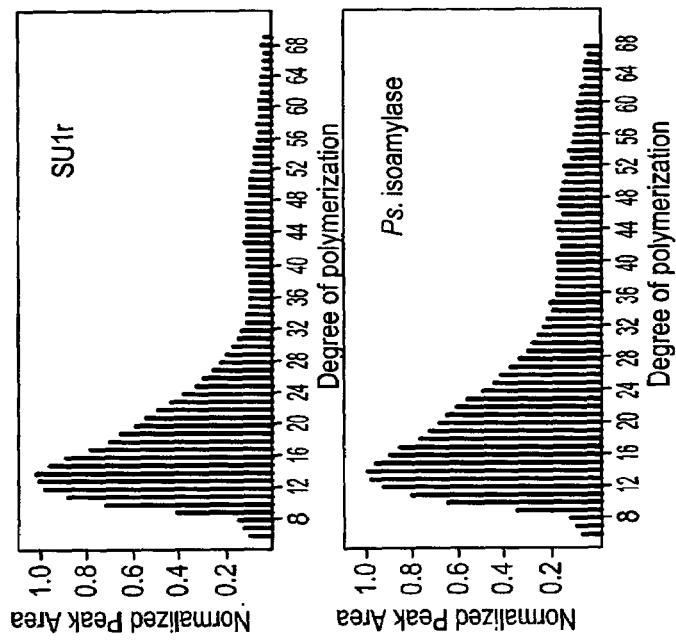
FIG. 16A
FIG. 16B
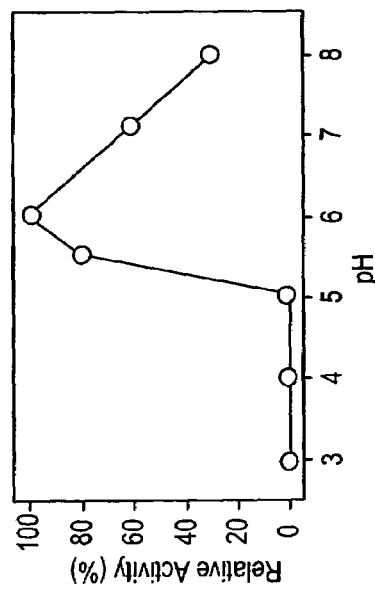
FIG. 15A
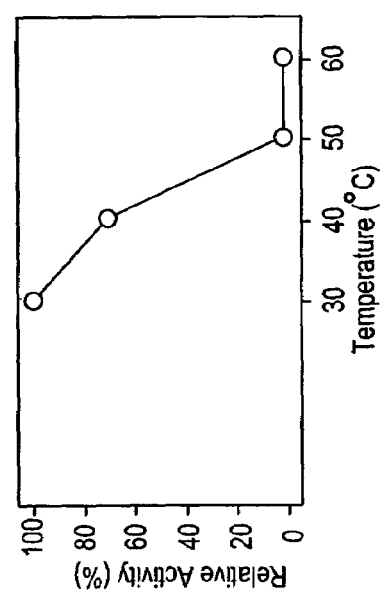
FIG. 15C

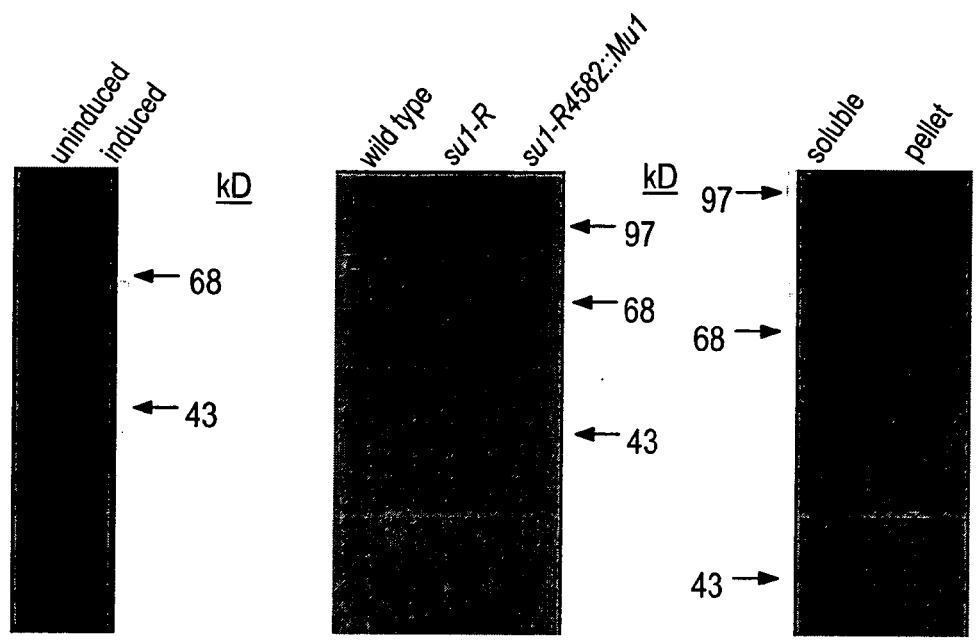
FIG. 18A　　FIG. 18B　　FIG. 18C
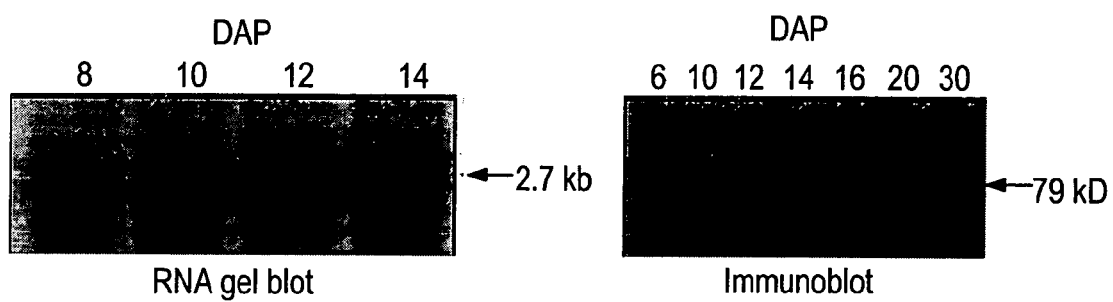
FIG. 19A　　FIG. 19B

Silver-stained gel

Immunoblot with anti-SU1

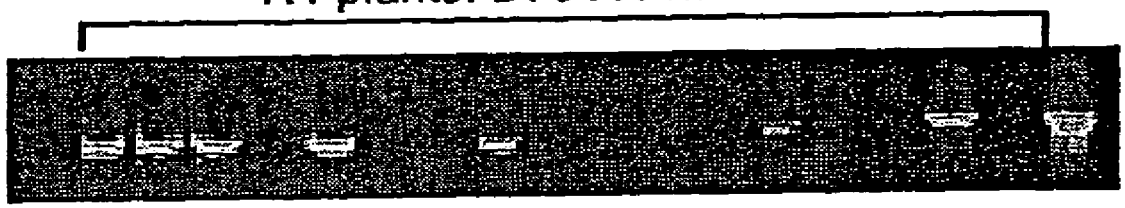
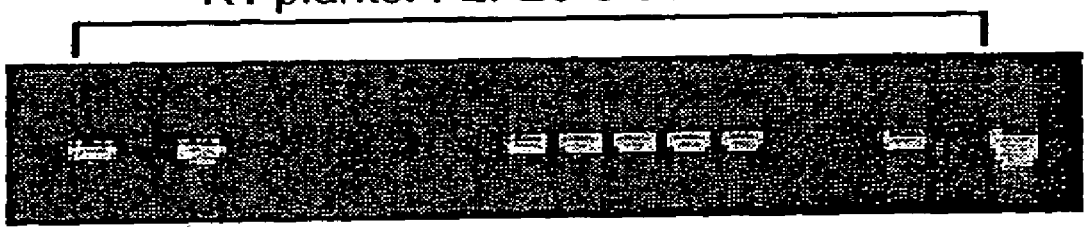
*FIG. 26*

nos 3'-end probe
Sul cDNA probe
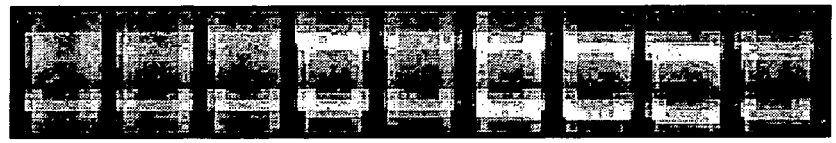
EtBr-stained gel
FIG. 27

ISOLATION OF SU1, A STARCH DEBRANCHING ENZYME, THE PRODUCT OF THE MAIZE GENE SUGARY1

CROSS REFERENCE TO RELATED APPLICATIONS

This application is a continuation-in-part application of application Ser. No. 09/256,741 filed on Feb. 24, 1999, now U.S. Pat. No. 6,410,716, which is a continuation-in-part of application Ser. No. 08/410,784 filed on Mar. 24, 1995, now U.S. Pat. No. 5,912,413, the whole of which are hereby incorporated by reference herein.

STATEMENT REGARDING FEDERALLY SPONSORED RESEARCH OR DEVELOPMENT

This invention was made in part with government support under U.S. Department of Agriculture Grant No. 95-34340-1605. Therefore, the U.S. Government has certain rights in this invention.

BACKGROUND OF THE INVENTION

Starch is the major storage carbohydrate in higher plants. The biochemical mechanisms of starch biosynthesis are of interest for understanding fundamental aspects of plant physiology and also for their potential utility in manipulating plant growth for practical purposes. Not only is starch a critical primary source of dietary carbohydrates, but it is also used extensively for various industrial purposes ranging from formation of packaging materials to ethanol production. Despite its wide availability in nature and many industrial applications, the mechanisms by which starch is formed in plant endosperm tissue are not well understood.

Starch consists essentially of a mixture of the homopolysaccharides amylose and amylopectin. Amylose is a linear chain of glucosyl units joined by $\alpha$-(1→4) glycosidic bond and normally constitutes about 25% of the total endosperm starch in maize (Zea mays). Amylopectin comprises many linear chains of glucosyl monomers joined by $\alpha$-(1→4) linkages and constitutes approximately 75% of the starch. The chains of amylopectin are joined to each other by $\alpha$-(1→6) glycosidic bonds, often referred to as branch linkages.

Sugary1 (Su1) is one of the oldest known mutations of maize and has been utilized as a sweet corn variety in North America since the 1700s. Phenotypically, immature mutant kernels with the Su1 gene mutations accumulate sucrose and other simple sugars, including phytoglycogen (Black et al., 1966; Evensen and Boyer, 1986), which gives corn its desirable sweetness. Specific efforts to improve particular varieties of sweet corn date back to the middle of the nineteenth century. More recently, Sumner and Somers reported in 1944 that the principal polysaccharide storage product in SU1 endosperm was a high molecular weight polysaccharide they called phytoglycogen. In 1958, Erlander proposed that phytoglycogen was a normal intermediate in the process of starch synthesis and that a debranching enzyme removed some of the branches by hydrolyzing the $\alpha$-1,6 branch points.

Phytoglycogen resembles amylopectin in the respect that $\alpha$-(1→4)-linked chains are joined by $\alpha$-(1→6) branch linkages, but the ratio of $\alpha$-(1→6) to $\alpha$-(1→4) linkages is significantly higher in phytoglycogen than it is in amylopectin (Manners, 1985). Although it has been suggested that the Su1 gene codes for a starch debranching enzyme (Pan and Nelson, 1984), three different protein isoforms, each with a different level of glycosidase activity, were observed. It is not clear whether this observation was due to differential posttranslational modifications of the proteins, or whether the active enzyme is a multimer which requires combination with products of other gene loci. Further investigation into the mechanisms of starch biosynthesis in plants would be desirable.

BRIEF SUMMARY OF THE INVENTION

The invention is based on the discovery of a maize endosperm cDNA that encodes a novel starch debranching enzyme, termed SU1. The Su1 gene produces a mRNA transcript of approximately 2.8 kb in kernels which includes a continuous open reading frame of 789 codons. The amino acid sequence deduced from the nucleotide sequence is significantly similar to that of bacterial isoamylases, enzymes that hydrolyze $\alpha$-(1→6) glycosidic bonds. Amino acid sequence similarity establishes SU1 as a member of the $\alpha$-amylase superfamily of starch hydrolytic enzymes, and indicates that SU1 is a starch debranching enzyme active in maize endosperm.

cDNA sequences encoding the SU1 protein or portions thereof can be incorporated into replicable expression vectors and the vectors transfected into an appropriate host (e.g., bacterial, yeast, eucaryotic cell culture). Alternatively, genomic DNA fragments encoding the SU1 protein can be utilized in situ. The expressed SU1 protein can be used as a replacement for the bacterial and fungal enzymes currently used in the starch processing industry. Also, the expressed products can be employed as immunogens in order to raise antibodies against SU1. Antibodies reactive with the SU1 protein show that SU1 is expressed in wild type maize endosperm tissue.

Thus, the invention generally features nucleic acid isolates encoding starch debranching enzyme, SU1, or portions thereof; the encoded SU1 protein or portions thereof; methods of producing SU1 or portions thereof; cells transformed with a recombinant vector containing the Su1 gene; antibodies to the SU1 protein or fragment thereof and methods to produce such antibodies; transgenic plants containing the Su1 gene, and methods to produce the transgenic plants.

The invention features a nucleic acid isolate able to hybridize under stringent conditions to the complement of a nucleic acid sequence encoding the SU1 protein, and the protein or polypeptide fragment, e.g., immunogenic fragment, thereof encoded by the nucleic acid isolate. The invention also features a recombinant expression vector comprising a nucleic acid isolate able to hybridize under stringent conditions to the complement of a sequence encoding the SU1 protein, and cells transformed with the recombinant expression vector, and methods of expressing the SU1 protein or polypeptide fragment encoded within the recombinant expression vector.

Also featured is a method of producing SU1 protein or polypeptide fragment thereof, comprising transforming a host cell with a nucleic acid able to hybridize under stringent conditions to a sequence encoding the Su1 protein having the amino acid sequence shown in FIG. 1 and linked to a nucleic acid sequence under the control of an inducible promotor, and inducing the inducible promotor to form a fusion protein comprising the SU1 protein.

The invention also features methods of producing antibodies to an SU1 fusion protein, and antibodies produced by such method. Also featured are transgenic plants containing the Su1 gene, and methods of making the transgenic plants.

As used herein, the term "mutate" and "mutation" refers to a nucleic acid sequence that possess one or more base pair insertions, deletions, or changes. As used herein, the term "identify" is intended to include other activities that require identification of an entity, such as isolation or purification. The terms "isolated" or "purified" refer to a nucleic acid or protein sequence that has been separated or isolated from the environment in which it was prepared or in which it naturally occurs. Such nucleic acid or protein sequences may be in the form of chimeric hybrids or fusions, useful for combining the function of the nucleic acid or protein sequences of the invention with other species and also include recombinant forms. The term "determinant" as used herein includes the site on an antigen at which a given antibody molecule binds. The term "immunogenic fragment" refers to a fragment of SU1 protein that reacts with antibodies specific for a determinant of SU1.

The SU1 protein can be used as an alternative hydrolase, including bacterial and fungal starch hydrolases and debranching enzymes, that are utilized in industrial starch processing applications. SU1 cDNA, SU1 genomic DNA, or portions thereof may be utilized as markers for the identification of specific corn varieties, and for the development of corn varieties with starch properties tailored for specific industrial applications. SU1 cDNA or genomic DNA fragments, can be used to produce these proteins or peptide fragments or as probes to identify nucleic acid molecules encoding related proteins or polypeptides (e.g., homologous polypeptides from related species and heterologous molecules from the same species). Assays for SU1 function, production or expression by cells are made possible by the development of antibodies reactive with the SU1 protein.

Other features and advantages of the invention will be apparent from the following description of the preferred embodiments thereof and from the claims.

BRIEF DESCRIPTION OF THE DRAWINGS

FIGS. 1A–1E show the sequence of the SU1 cDNA clone (SEQ ID NO:1) and its amino acid sequence translation (SEQ ID NO:2);

FIGS. 2A–2P show the sugary1 genomic sequence (SEQ ID NO:3);

FIGS. 3A–3B show the deduced amino acid sequence of SU1 and comparison with isoamylase from *Pseudomonas* (SEQ ID NO:39);

FIGS. 15A–15C are graphs showing pH and temperature optima for SU1r activity and stability;

FIGS. 16A and 16B show chain length distribution produced by SU1r and *Pseudomonas* isoamylase, respectively. Amylopectin from wx maize was debranched by SU1r (1 h) or *Pseudomonas* isoamylase (24 h), and chain length distribution was determined quantitatively by HPAEC-ENZ-PAD and normalized to the most abundant glucan chain;

FIGS. 18A–18C show immunoblot analyses with anti-SU1 polyclonal antibody in *E. coli* extracts, total kernel extracts, and soluble and granule-associated proteins, respectively;

FIGS. 19A and 19B show temporal expression of SU1 mRNA and SU1 protein, as indicated by RNA gel blot analysis using a SU1 cDNA probe and immunoblot analysis with anti-SU1 polyclonal antibody, respectively.

FIG. 20A shows the elution profile of SU1 activity, while FIG. 20B represents the immunoblot analysis of the fractions with anti-SU1;

FIG. 21A shows the elution profile of activity of SU1, while FIG. 21B represents immunoblot analysis of the indicated fractions with anti-SU1;

FIG. 26 shows Mendelian segregation of SU1 transgenes;

FIG. 27 shows expression of SU1 sense transgenes at the mRNA level; and

DETAILED DESCRIPTION OF THE INVENTION

Figure 4A:
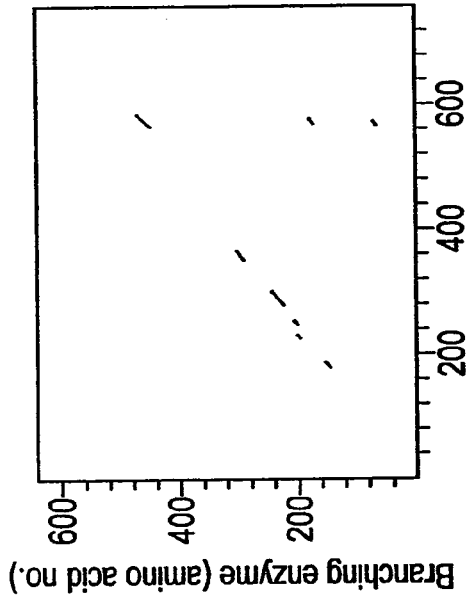
FIGS. 4A–4C are graphs showing a comparsion of the deduced amino acid sequence of SU1 of isoamylase from *P. amyloderamosa*, branching enzyme from *Bacillus stearothermophilus*, and α-amylase from *Bacillus megaterium*, respectively.

The genes coding for debranching enzymes have not previously been identified or cloned in plants. Currently, bacterial and fungal starch hydrolases, including debranching enzymes, are utilized in industrial applications. A debranching enzyme native to maize would have utility in industrial starch processing applications, and may have unique advantages over the microbial enzymes of the prior art. In addition, portions of the SU1 clone may have potential use as markers for the identification of specific corn varieties, and also for the development of corn varieties with starch properties tailored for specific industrial applications.

The 2712-bp nucleotide sequence of the SU1 cDNA clone (Gen Bank Accession No. U18908) is shown in FIGS. 1A–1E (SEQ ID NO:1). A sequence of 14 consecutive T residues is located at one end of the clone, identifying the polyadenylation site and the 3' end of the mRNA. A continuous open reading frame (ORF) of 789 codons begins 88 nucleotides from the 5' end of the cDNA clone and terminates 240 nucleotides prior to the poly(A) adenylation site. This ORF corresponds to a polypeptide of 789 amino acids (SEQ ID NO:2).

The nucleotide sequence of a full-length genomic clone of SU1 also has been determined (Accession No. AF030882), and the fine structure of the Su1 gene has been established through comparisons with the SU1 cDNA. This sequence is shown in FIGS. 2A–2P (SEQ ID NO:3). The transcribed region of SU1 is 8555 bp in length and comprises 18 exons ranging in size from 72 bp to >501 bp. These exons are interrupted by 17 introns ranging in size from 72 bp to 1708 bp. The specific nucleotide ranges and sizes of individual exons and introns are given in Table I.

The intron donor- and acceptor splice sites show complete homology to the invariant consensus cleavage sites (Singer and Berg, 1991). The nucleotide sequence of the translated regions of the gene was 99.8% identical to that reported for the SU1 cDNA. The site in the 3' exon at which transcript cleavage and polyadenylation occur matches the conserved RNA processing site known in other plant genes (Gallie, 1993). Two closely-spaced putative transcription start sites were identified by nuclease protection assay approximately 50 bp upstream of the ATG codon most likely to initiate translation (ATG at nt 1971; transcription start site at nt 1920 and nt 1922); another putative transcription start site was identified by RACE-PCR 87 bp upstream of the same ATG at nt 1884. The potential transnational start site adheres closely to the established consensus sequence for this region in higher plants (Joshi, 1987).

TABLE I

Nucleotide Ranges and Sizes of Exons and Introns

| Exon/Intron | Nucleotide Range | Size (bp) |
|---|---|---|
| E1 | 1884–2333 | 450 |
| I1 | 2334–2577 | 244 |
| E2 | 2578–2763 | 186 |
| I2 | 2764–2887 | 124 |
| E3 | 2887–2980 | 93 |
| I3 | 2981–3314 | 334 |
| E4 | 3315–3467 | 153 |
| I4 | 3468–3923 | 456 |
| E5 | 3924–4000 | 77 |
| I5 | 4001–4247 | 247 |
| E6 | 4248–4389 | 142 |
| I6 | 4390–4480 | 91 |
| E7 | 4481–4588 | 108 |
| I7 | 4589–4706 | 118 |
| E8 | 4707–4792 | 86 |
| I8 | 4793–5062 | 270 |
| E9 | 5063–5134 | 72 |
| I9 | 5135–5206 | 72 |
| E10 | 5207–5333 | 127 |
| I10 | 5334–7041 | 1708 |
| E11 | 7042–7128 | 87 |
| I11 | 7129–7902 | 774 |
| E12 | 7903–7995 | 93 |
| I12 | 7996–8429 | 434 |
| E13 | 8430–8588 | 159 |
| I13 | 8589–8811 | 223 |
| E14 | 8812–8895 | 84 |
| I14 | 8896–9316 | 421 |
| E15 | 9317–9397 | 81 |
| I15 | 9398–9489 | 92 |
| E16 | 9490–9572 | 83 |
| I16 | 9573–9699 | 127 |
| E17 | 9700–9817 | 118 |
| I17 | 9818–9937 | 120 |
| E18 | 9938–10438 | 501 |

Analysis of the region upstream of the transcriptional start site(s) in SU1 did not reveal obvious TATA or CCAAT promoter elements. Two sequences similar to G-box elements (Schulze-Lefert et al., 1989; van der Steege et al., 1992) were identified in the promoter region (nt 1634-1642 and nt 1679-1688), which may be important for environmental induction of SU1 transcription. An upstream region of approximately 200 bp (nt 12-nt 213) shares high sequence identity with upstream regions of two other maize genes, oleosin KD18 (79% identity; Accession No. J05212), and GapC2 (80% identity: Accession No. X73151).

Observing hybridization of SU1 cDNA probes to multiple genomic DNA fragments indicates that the gene product, SU1, is a member of a gene family in maize. As many as 14 different regions of the genome form heteroduplexes with a specific portion of the SU1 cDNA even under high-stringency conditions. Not all probe segments from the SU1 cDNA hybridize with high efficiency to multiple regions of the maize genome, suggesting that specific domains of SU1 are conserved in the putative gene family. The single transcript detected by hybridization to SU1 cDNA probes in maize kernels 20 days after pollination originates from the Su1 gene.

The SU1-related genes may code for enzymes present in germinating kernels or other plant tissues that are active in starch utilization. Multiple α-(1→6) hydrolase activities have been characterized in these tissues (Manners and Rowe, 1969; Lee et al., 1971). The SU1 cDNA probes that formed heteroduplexes with multiple genomic segments comprise codons 456 to 818 of the discernible ORF. This region of SU1 is similar in amino acid sequence to *Pseudomonas* isoamylase (27% identity over 338 aligned residues), but not to as great an extent as the other portions of the maize protein.

The Su1 gene produces a mRNA transcript of approximately 2.8 kb in kernels. Amino acid sequence comparisons indicate that regions of SU1 are similar in primary structure to specific portions of several types of enzyme known to hydrolyze glucose homopolymers. These include bacterial debranching enzymes such as isoamylases and pullulanases, enzymes that hydrolyze α-(1→4) glycosidic linkages such as α-amylases and cyclomaltodextrinase, and both prokaryotic and eucaryotic branching enzymes.

Figure 3A:
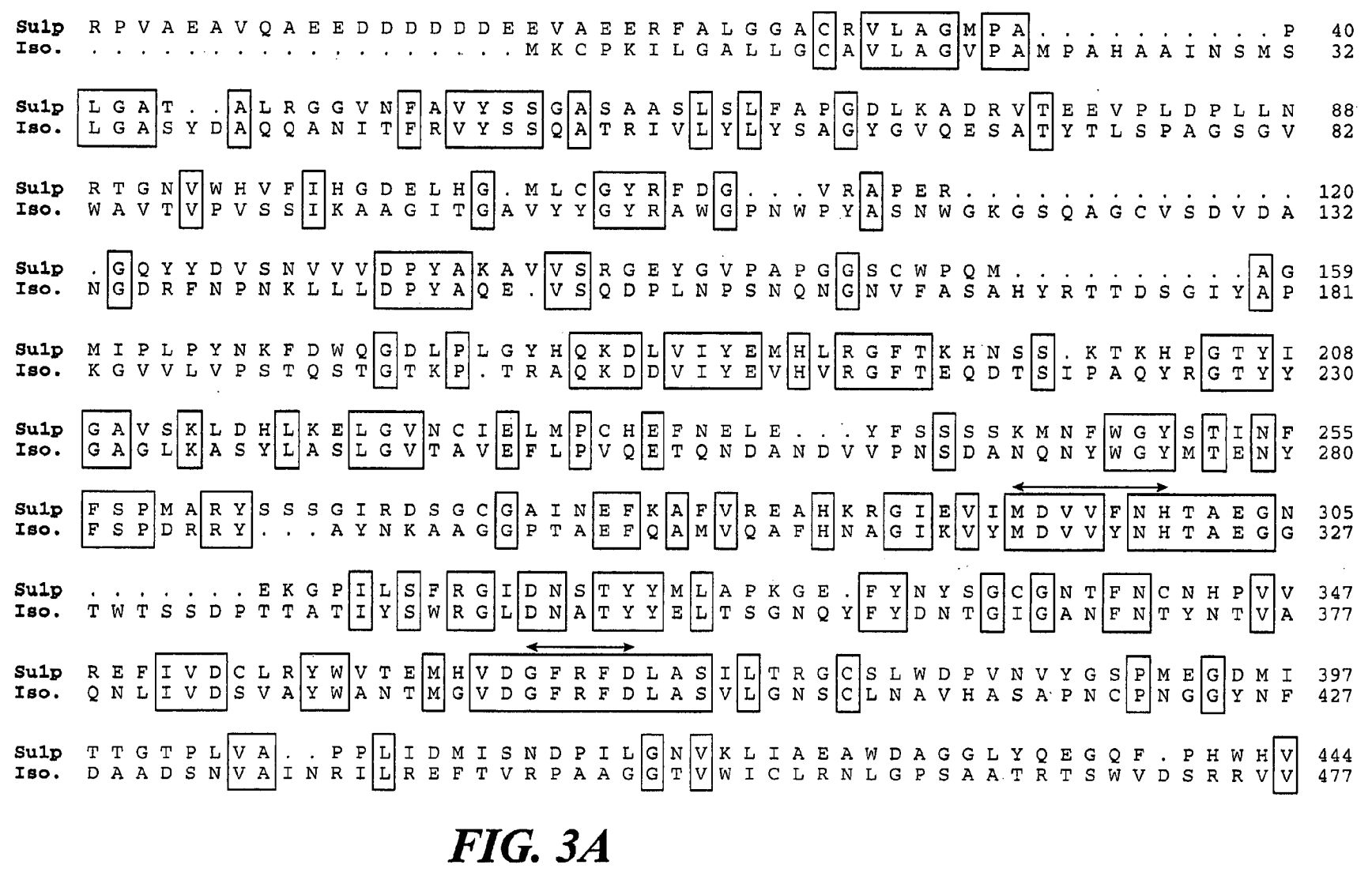
Figure 3B:
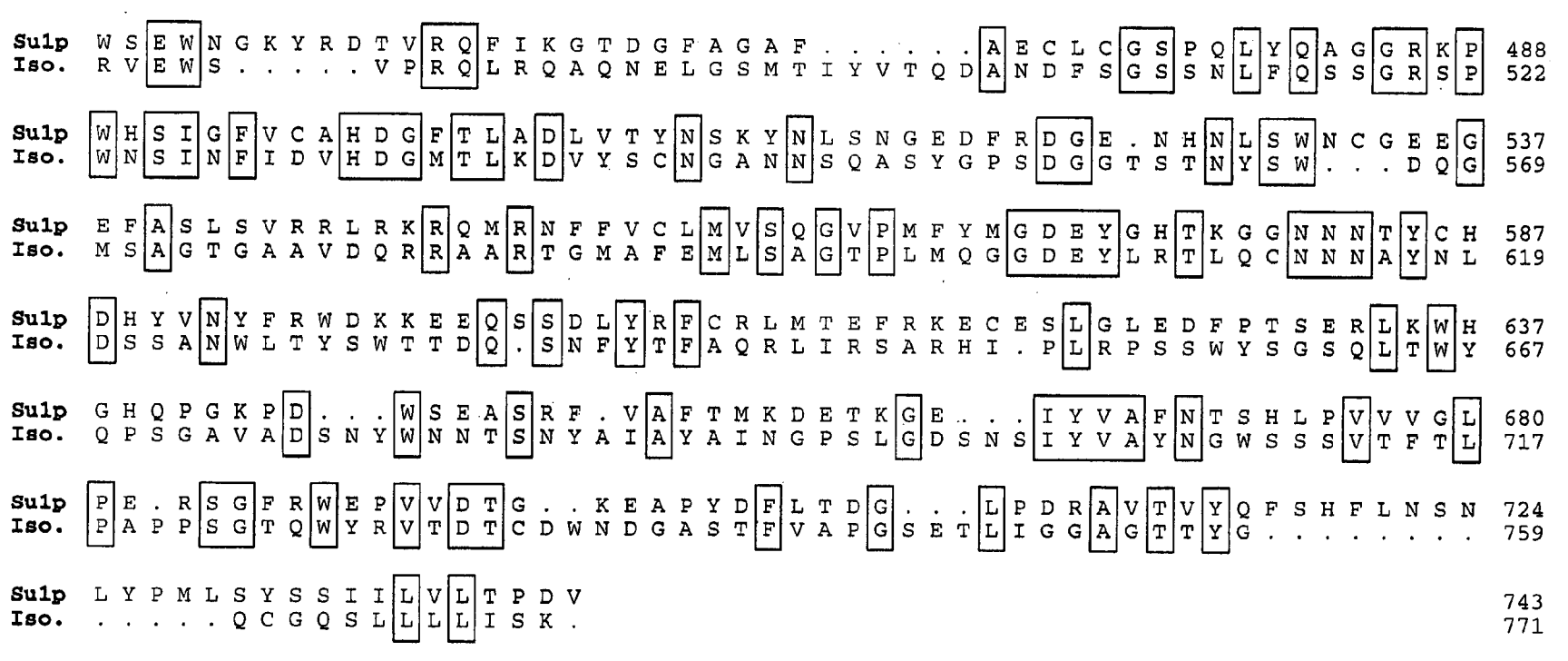

FIGS. 3A–3B show the deduced amino acid sequence of SU1 (from SEQ ID NO:2) aligned with that of isoamylase from *P. amyloderamosa* (SEQ ID NO:39). Of the 695 aligned residues, 32% are identical in the two polypeptides. Localized regions show an even higher degree of amino acid sequence identity. For example, of the 99 amino acids between positions 277 and 375 of SU1, 53% are identical to the residue found at that position in isoamylase. Other highly conserved regions of SU1 are residues 476 to 505, where 57% of the 30 amino acids are identical to those of isoamylase, and residues 180 to 222, where 53% of the 43 aligned amino are the same as in the bacterial protein. Two conserved sequence blocks observed previously in all known α-amylases, branching enzymes, and debranching enzymes (Svensson, 1988; MacGregor and Svensson, 1989; Jesperson et al., 1993) are found within SU1. Two additional conserved sequences found specifically in the α-amylases, however, are lacking in SU1.

Amino acid sequence similarity with isoamylase from *P. amyloderamosa* indicates that SU1 is a member of the α-amylase superfamily of starch hydrolytic enzymes. This family includes enzymes from bacteria, fungi, plants, and mammals (Svensson, 1988; MacGregor and Svensson, 1989). The sequence similarity between members of this superfamily is located primarily in two spatially conserved regions that are proposed to form catalytic and starch binding structures within the proteins (Matsuura et al., 1984; Nakajima et al., 1986; Jesperson et al., 1993). SU1 contains both of these conserved regions, and in addition displays extensive primary sequence similarity with the debranching enzymes of the α-amylase superfamily. The characterized enzyme to which SU1 exhibits the highest degree of amino acid sequence identity, isoamylase from *Pseudomonas*, is known to completely hydrolyze the α-(1→6) linkages of amylopectin and glycogen (Yokobayashi et al., 1970; Amemura et al., 1988). Thus, the nucleotide sequence data indicate that SU1 is a starch debranching enzyme active in maize endosperm.

Figure 4B:
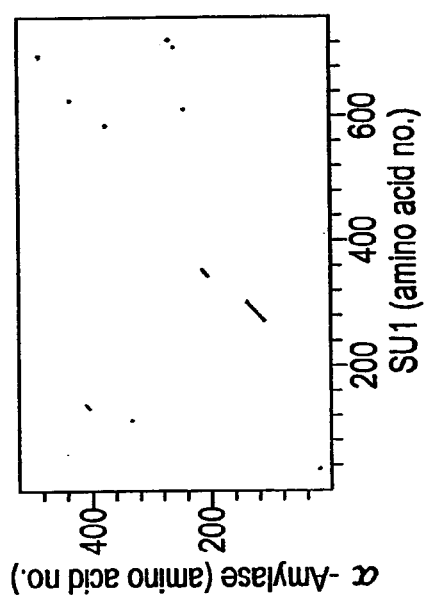
Figure 4C:
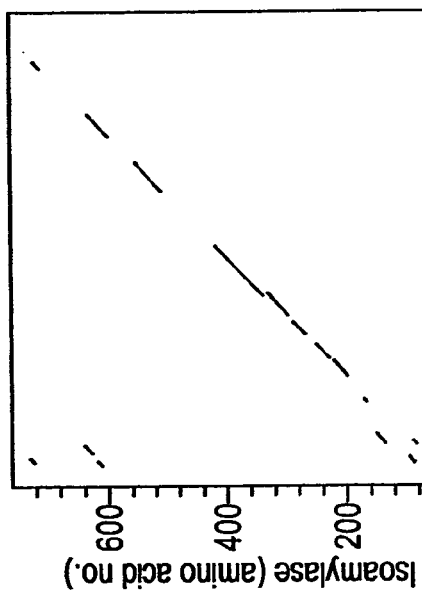

FIGS. 4A–4C illustrate the deduced amino acid sequence of SU1 compared to that of isoamylase from *P. amyloderamosa* (GenBank accession number P10342), branching enzyme from *B. stearothermophilus* (GenBank accession number P30538), or α-amylase from *B. megaterium* (GenBank accession number P20845), all from prokaryotic organisms. The sequence identity between SU1 and *Pseudomonas* isoamylase extends over almost the entire 742 known residues of the maize protein, whereas only short regions of sequence identity are observed between SU1 and the branching enzyme or α-amylase. Thus, among known starch hydrolytic enzymes, SU1 is most closely related to those that hydrolyze α-(1→6) linkages. Among these, the relationship of SU1 to isoamylase is greater than to pullulanase, although the similarity with pullulanase is significantly more extensive than that with branching enzyme or α-amylase. The most extensive amino acid sequence similarity detected is with the deduced product of the *E. coli* gene glgX, a gene of unknown function located in the operon that also codes for a glycogen branching enzyme (Romeo et al., 1988).

Microprojectile bombardment has demonstrated high success for generation of transgenic plants. Microprojectiles coated with a gene that regulates pigmentation have been successfully targeted to a variety of tissues (Ludwig et al., Science 247:449–450 (1990)). Microprojectile bombardment is a useful technique in which to form transgenic maize plants using the gene of the present invention. In one embodiment, microprojectile particles coated with a vector containing the cDNA of the gene coupled with appropriate promoter and termination sequences are inserted into the genome. A genetic marker is included in the vector to detect transformed cells. Using the transformation procedure and the appropriate promotor sequence (e.g., mutated SU1 promoter sequences, seed-specific promoters from other genes, or inducible promotor, such as a heat shock promotor), maize plants are generated in which the timing and/or level of expression of the Su1 gene locus is modified in endosperm tissue. Use of promoters that specify gene expression in plant tissues other than endosperm can be incorporated to express SU1 in tissues in which it is not normally expressed. Also, modifications of the coding region of SU1 allow for production of transgenic plants that have mutated SU1 enzyme activity (e.g., enhanced or reduced binding or catalytic activity) in endosperm.

The following examples are presented to illustrate the advantages of the present invention and to assist one of ordinary skill in making and using the same. These examples are not intended in any way to otherwise limit the scope of the disclosure.

EXAMPLE I

Isolation and Characterization of SU1 cDNA Clones

The Su1 gene locus can be isolated by transposon tagging methodology. Transposon tagging strategy is based on the assumption that insertion of a transposable element in a target gene will cause a mutation that can be identified by a specific phenotype. Two lines of evidence indicated that the cloned transposon-containing genomic DNA is within the SU1 locus. First, plants containing any of four independent SU1 mutations (SU1-R4582::Mu1, SU1-R2412, SU1-R7110, and SU1-R3162) displayed restriction fragment length polymorphisms (RFLP) in the same genomic interval, and these polymorphisms cosegregated with the sugary phenotype. The probability is very low that each of these rare genomic rearrangements would occur coincident with a SU1 mutation but not be causally related to SU1 function. Second, insertion of Mu1 within the cloned region occurred de novo within the same narrow developmental window in which SU1-R4582::Mu1 arose.

Figure 5:
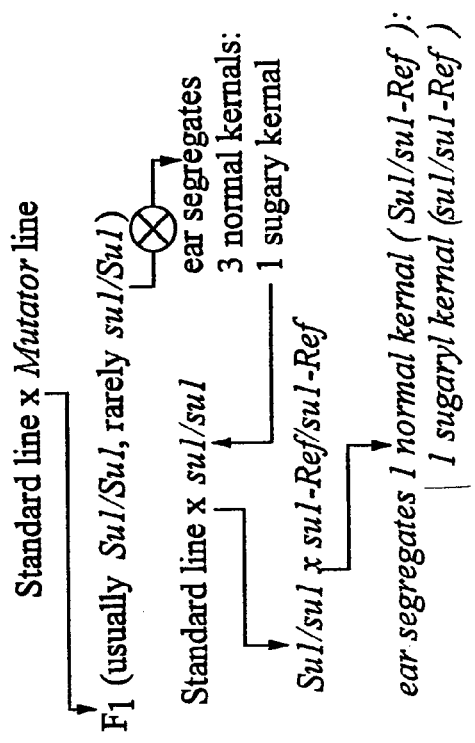
FIG. 5 shows the crossing strategy used in the invention.

The Mutator (Mu) transposable element system can be used to generate new mutations at the Su1 gene locus (Scanlon et al., 1994). Referring now to FIG. 5, mutations at the Su1 gene locus are generated by crossing active Mutator plants with standard lines homozygous for the non-mutant allele SU1. The F1 progeny are grown and self-pollinated, and the resulting F2 ears are examined for 3:1 segregation of normal and sugary kernels. Sugary kernels from individual F2 ears are planted, and the resultant plants are crossed to standard lines. Progeny from this cross (heterozygous for the putative SU1 mutation) are planted and crossed to tester plants homozygous for SU1-Ref. Allelism of the new mutation with SU1-Ref is indicated by 1:1 segregation of normal: sugary kernels on the resulting ears.

Figure 6A:
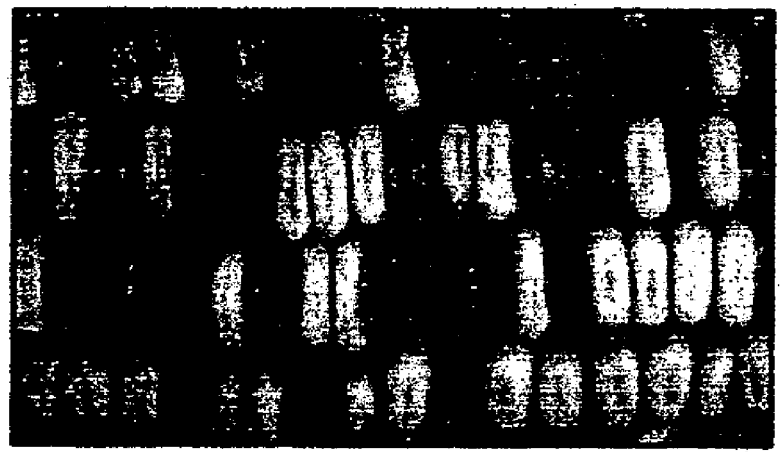
FIG. 6A shows an ear of corn resulting from the cross of FIG. 5.

FIG. 6A shows a typical ear resulting from this cross, which contained sugary and normal kernels at approximately equal frequencies. These data indicate the new mutation did not complement SU1-Ref, and thus most likely is allelic to mutations at the Su1 gene locus. The one-to-one segregation ratio also confirmed that the sugary phenotype of the original mutant kernel is a single gene trait. Five new SU1 mutations are identified in this way and are designated SU1-R4582::Mu1, SU1-R2412, SU1-R7110, SU1-R3162, and SU1-R8064.

Figure 6B:
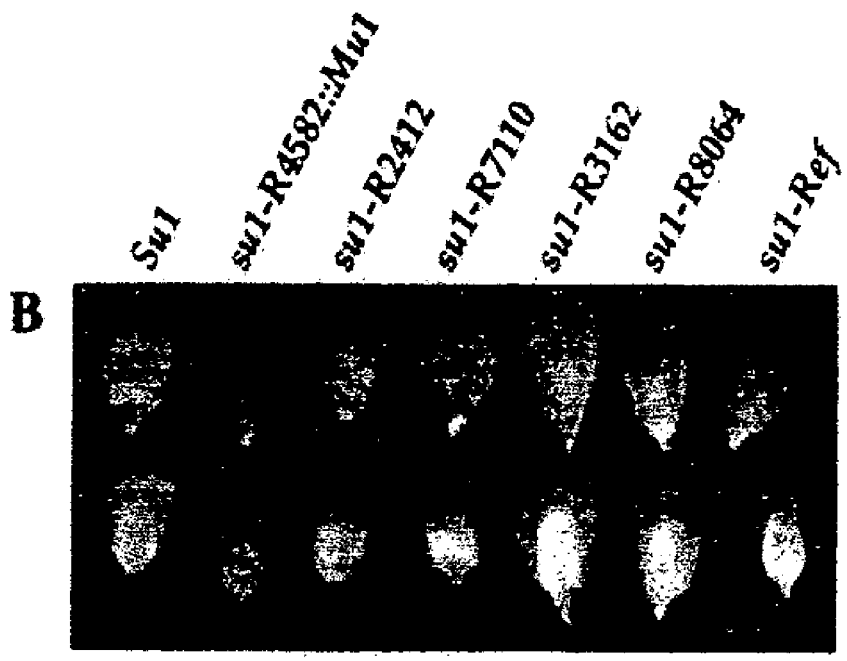
FIG. 6B shows kernel phenotypes in which the Su1 gene is present.

FIG. 6B shows the kernel phenotypes that result from each new SU1 mutation in the homozygous condition. The mutations SU1-R3162 and SU1-R8064 resulted in kernel phenotypes similar to that resulting from SU1-Ref. The mutation SU1-R2412 resulted in a less severe phenotype, with only a slight glassiness and wrinkling at the crown of the kernel. Kernels homozygous for SU1-R4582::Mu1 or SU1-R7110 generally appeared to be more severely shrunken than SU1-Ref homozygotes. These SU1 mutations together with SU1-Ref can be introgressed into a common inbred line to eliminate potential phenotypic variability resulting from genetic background effects.

Figure 7:
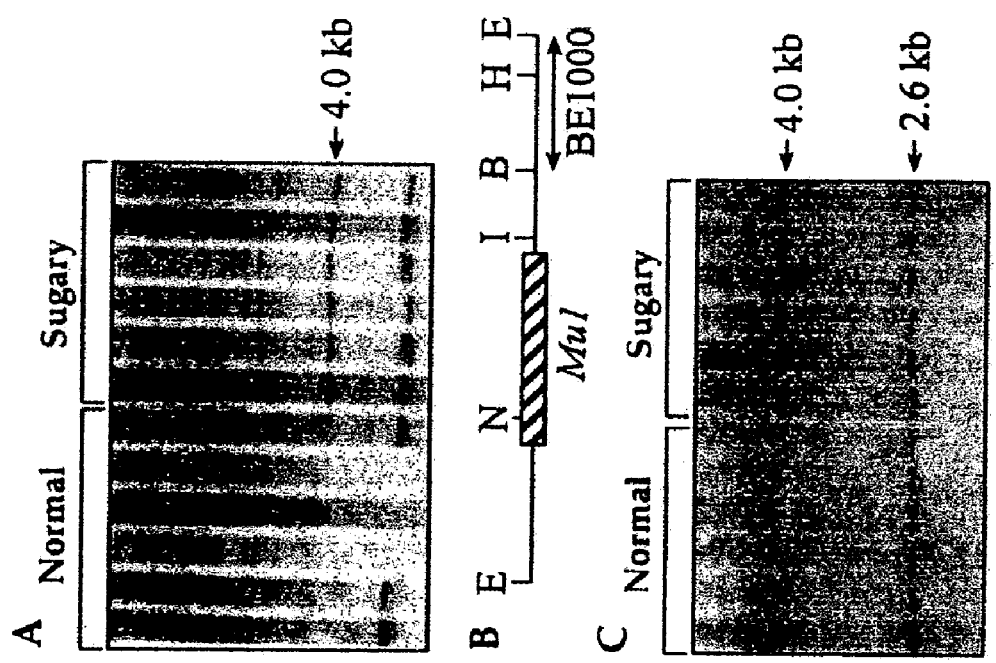
FIG. 7A shows part of a DNA gel blot analysis of DNAs isolated from maize seedlings.
FIG. 7B shows a physical map of the cloned fragment.
FIG. 7C shows a DNA gel blot analysis in which probe BE1000 is hybridized with genomic DNAs from seedlings in the population segregating for SU1-R4582::Mu1 and SU1.

Plants containing SU1-R4582::Mu1 and others lacking this allele are examined for the presence of a specific Mu transposon that cosegregated with the putative Mu-induced mutation. This analysis utilized the segregating population of sugary kernels (SU1-R4582::Mu1/SU1-Ref) and sibling normal kernels containing the non-mutant allele SU1 (SU1/SU1-Ref) indicated in FIG. 5. FIG. 7A shows part of a DNA gel blot analysis of DNAs isolated from maize seedlings. Genomic DNA from the resulting seedlings is digested with EcoRI and probed on DNA gel blots with the internal 960-bp MluI fragment of Mu1. The length of the fragment marked with the arrow is estimated based on the mobility in the same agarose gel of standards of known nucleotide sequence. These data identified a 4.0-kb EcoRI restriction fragment containing sequences homologous to the transposon Mu1 that cosegregated with SU1-R4582::Mu1. In total, the genomic DNAs of seedlings grown from 60 sugary kernels and 57 normal kernels are examined. This specific Mu1-homologous sequence, therefore, either is located within the Su1 gene locus or is tightly linked to that locus.

A 4.0-kb EcoRI restriction fragment containing Mu1 can be isolated from the genome of a SU1-R4582::Mu1/SU1-Ref plant. The fragment initially was identified in a library of size-selected genomic DNA fragments constructed in a bacteriophage λ vector, based on hybridization to a probe internal to Mu1. This recombinant phage is single-plaque purified, and the genomic DNA insert is subcloned as part of plasmid pMJ60. FIG. 7B shows a physical map of the cloned fragment. Restriction sites are indicated for EcoRI (E), NotI (N), HincII (I), HindIII (H), and BamHI (B). The position of restriction enzyme recognition sequences in pMJ60 indicated the transposon present is Mu1 and predicted the position and orientation of this 1.4-kb element within the 4.0-kb EcoRI fragment. The nucleotide sequence of both termini of the transposon matches the known sequence of Mu1 (Barker et al., 1984). A direct repeat sequence of 9 bp is observed in the genomic DNA immediately adjacent to the transposon at each of its termini, typical of Mu transposable elements. In this instance the particular repeated sequence is 5'-CGCGCTCCG-3'.

The region of DNA adjacent to the cloned Mu1 transposon cosegregates with SU1-R4582::Mu1, confirming that this sequence is derived from a genomic interval located within or nearby the Su1 gene locus. The 1.0-kb BamHI-EcoRI genomic fragment flanking Mu1 in the cloned DNA can be purified and used as a hybridization probe (termed BE1000). FIG. 7C shows sample results of a DNA gel blot analysis in which probe BE1000 is hybridized with genomic DNAs from seedlings in the population segregating for SU1-R4582::Mu1 and SU1. The lengths of the fragments marked with arrows are estimated based on the mobility in the same agarose gel of standards of known nucleotide sequence. This genomic probe detected a 4.0-kb EcoRI fragment that is present in all SU1-R4582::Mu1/SU1-Ref plants, but is missing from all SU1/SU1-Ref plants. Thus, the cloned Mu transposon is the same element that is within or tightly linked to the Su1 gene locus. Probe BE1000 identifies a second EcoRI fragment of 2.6 kb that is present in all plants examined, and presumably is representative of the non-mutant progenitor allele. This is the only fragment observed in the SU1/SU1-Ref plants, indicating the reference mutation is not associated with a discernible deletion or insertion.

Figure 8:
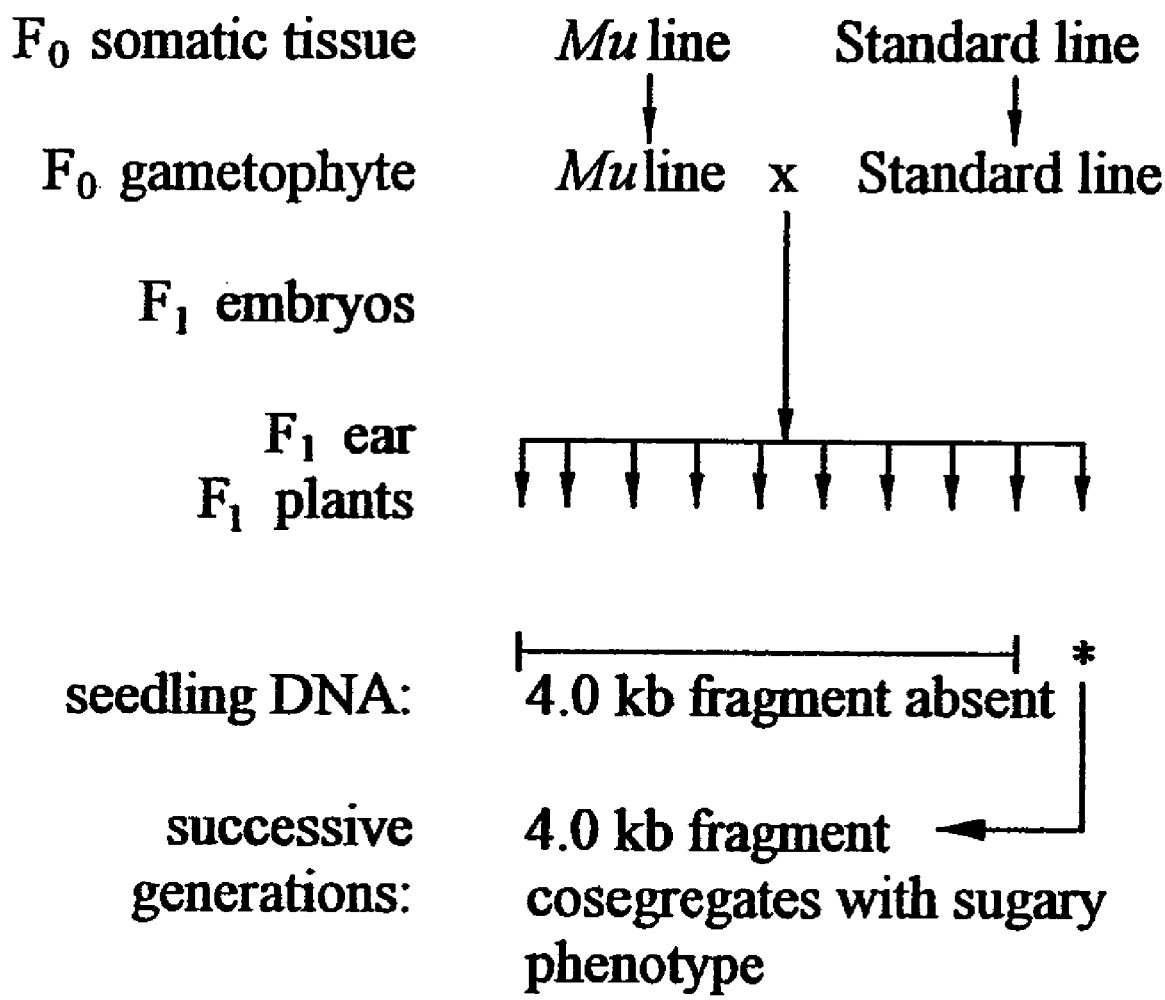
FIG. 8 shows a pedigree analysis of the generations that resulted in the mutation SU1-R4582::Mu1.

FIG. 8 illustrates a pedigree analysis of the generations that resulted in the mutation SU1-R4582::Mu1. A single F1 plant, indicated with an asterisk, produced sugary kernels on its self-pollinated ear. The self-pollinated ears of 69 additional F1 plants are completely wild type with respect to the sugary phenotype. Genomic DNA was isolated from nine other F1 plant seedlings and examined for the presence of a 4.0-kb EcoRI fragment homologous to genomic probe BE1000. As indicated, none of the F1 seedling DNAs contained a 4.0-kb EcoRI fragment homologous to probe BE1000.

The pedigree shown in FIG. 8 indicates that the cloned DNA is in fact from the SU1-R4582::Mu1 allele, as opposed to the alternative possibility that the isolated transposon is linked to the Su1 gene locus but is not the causative agent of the mutation. This conclusion is based on the observation that the 4.0-kb EcoRI fragment containing Mu1 arose in the same narrow developmental window as did the SU1-R4582::Mu1 mutation. F1 plants derived from 70 kernels of the F1 ear produced by crossing the F0 Mutator line to an F0 standard line are self-pollinated in the original screen for sugary mutants. Only one of these F1 plants produced sugary kernels on its self-pollinated ear. The SU1-R4582::Mu1 mutation, therefore, could not have been present in the somatic cells of either F0 parent but must have arisen during gametogenesis in one parent or early in development of the specific F1 embryo that eventually resulted in the sugary kernels. Consistent with this hypothesis, self-pollination of the Mutator F0 parent yielded an ear without sugary kernels. To determine whether the 4.0-kb, Mu1-containing fragment is present in the F0 progenitor plants, nine more kernels from the F1 ear are planted, and genomic DNA can be extracted from the resulting seedlings. In DNA gel blot analysis using probe BE1000 only the 2.6-kb EcoRI fragment is detected. If the 4.0-kb fragment existed in one of the F0 plants, then by Mendelian segregation the fragment would have been present in approximately one-half of the plants analyzed. Thus, the 4.0-kb, Mu1-containing fragment is not present prior to the generation in which SU1-R4582::Mu1 is formed.

Mutations of the Su1 gene locus other than SU1-R4582::Mu1 can be analyzed to determine whether they also cosegregate with physical alterations in the cloned region of the genome. Populations segregating for the non-mutant allele SU1 and either SU1-R2412, SU1-R7110, or SU1-R3162 can be established as shown in FIG. 5. For each allele genomic DNA from eight SU1/SU1-Ref plants and eight SU1/SU1-Ref plants is digested with EcoRI and probed in DNA gel blot analysis with genomic fragment BE1000.

Figure 9:
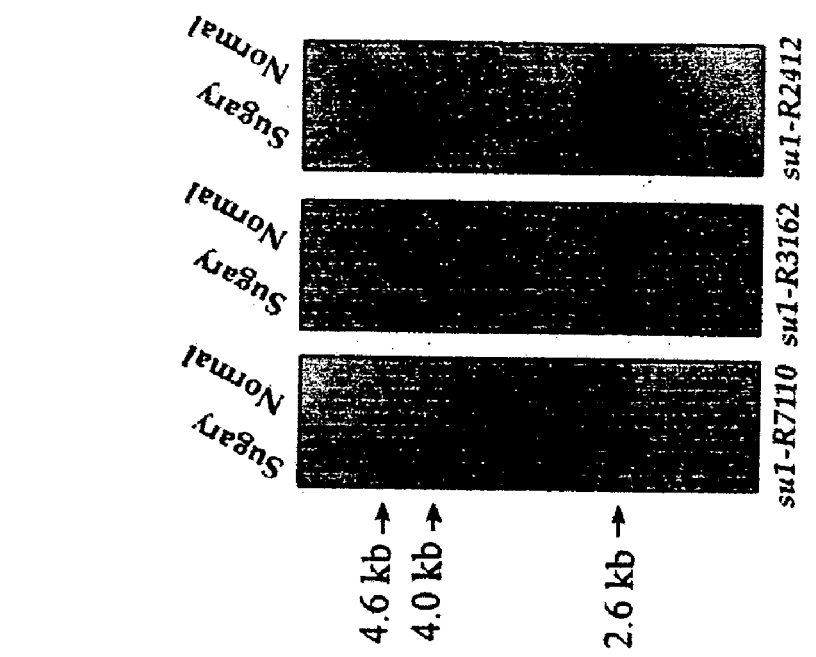
FIG. 9 shows a gel blot of seedling DNA digested with EcoRI and probed with a hybridization probe.

FIG. 9 illustrates that genomic insertions are linked to SU1-R2412, SU1-R7110, and SU1-R3162. Normal and sugary sibling kernels from populations segregating for the non-mutant allele SU1 and either SU1-R7110, SU1-R3162, or SU1-R2412 are germinated as shown in FIG. 5. Genomic DNA from the resulting seedlings is digested with EcoRI and probed on DNA gel blots with fragment BE1000 from the SU1-R4582::Mu1 genomic clone. The lengths of the fragments marked with arrows are estimated based on the mobility in the same agarose gel of standards of known nucleotide sequence.

As illustrated in FIG. 9, the 4.0-kb EcoRI fragment that in the SU1-R7110 and SU1-R3162 families is present in all the seedlings grown from sugary kernels but is not observed in any seedlings grown from non-mutant sibling kernels. A different EcoRI fragment, 4.6 kb in length, is found to cosegregate with SU1-R2412. As observed previously a 2.6-kb EcoRI fragment is detected by the probe in all plants examined. Because SU1-R7110 and SU1-R3162 arose in a Mu background, each resulted from the insertion of a 1.4-kb transposon, most likely Mu1, into the same 2.6-kb genomic interval that also is modified in plants containing SU1-R4582::Mu1. The mutation SU1-R2412 is likely to have occurred via an insertion of a 2.0-kb element into this same region. The broad band of approximately 2.6 kb observed in the SU1-R2412 and SU1-R3162 populations is resolved in other gels into two fragments of about 2.6 and 2.7 kb. Thus in these backgrounds the non-mutant allele SU1 associates with an EcoRI fragment of 2.7 kb, in contrast to the 2.6-kb fragment observed for this allele in the families segregating for SU1-R4582::Mu1 or SU1-R7110.

Figure 10:
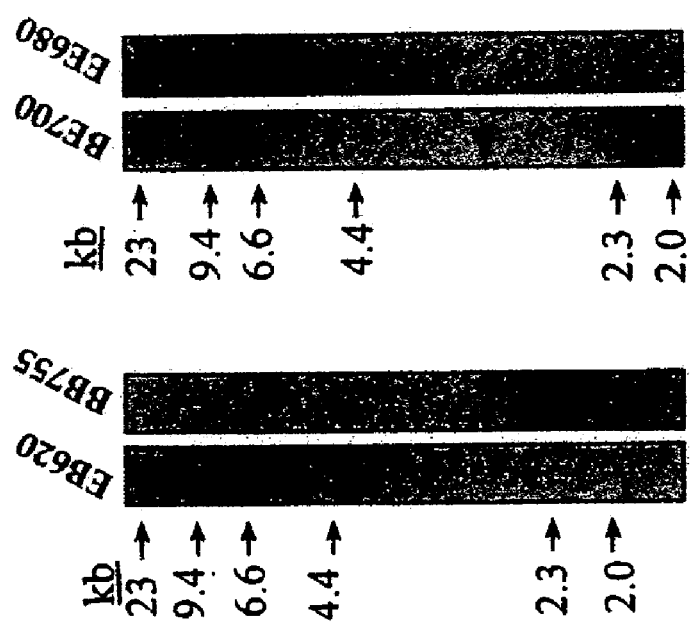
FIG. 10 shows DNA gel blot analysis using various segments of the SU1 cDNA as probes.

Referring now to FIG. 10, DNA gel blot analysis using various segments of the SU1 cDNA as probes is utilized to examine whether SU1 is a unique sequence within the maize genome. In FIG. 10, restriction fragments from the SU1 cDNA are used as probes. Maize genomic DNA is digested with BamHI and hybridized with the probes in DNA gel blots under high-stringency conditions. Arrows indicate the mobility in the same agarose gels of standards of known nucleotide sequence.

As illustrated in FIG. 10, a single BamHI fragment hybridizes strongly with cDNA probe EB620 or BB755. In contrast, probe EE680, located downstream of probe BB755, hybridizes with approximately equal efficiency with 14 different BamHI fragments. At most, two of these fragments could be explained by allelic diversity at the Su1 gene locus. Twelve other fragments, therefore, contain sequences that are sufficiently complementary in nucleotide sequence to probe EE680 to form heteroduplexes even under the high-stringency conditions used. Probe BE700, located immediately upstream of probe EE680 also detects multiple fragments in the genome. These DNA gel blot data are in agreement with the single hybridization signal obtained using genomic probe BE1000, because all the exons in this genomic interval are contained within cDNA probe BB755.

EXAMPLE II

SU1 Transcription and Analysis of an SU1 cDNA Clone

To characterize the product of the Su1 gene locus, SU1, a cDNA clone of the SU1 mRNA is obtained. The genomic fragment BE1000 is used as a probe in RNA gel blot analysis and detected a transcript of approximately 2.8 kb in total RNA isolated from wild-type kernels harvested 20 days after pollination. This transcript is more abundant in the polyadenylated RNA fraction than in total RNA, suggesting BE1000 detected the SU1 mRNA. A cDNA library constructed from maize endosperm mRNA in a bacteriophage λ vector is screened for hybridization with probe BE1000. In one embodiment, eight hybridizing clones are identified among approximately 200,000 recombinant phage examined. The longest cDNA insert in any of these clones is approximately 2.4-kb. After single plaque purification, the longest cDNA insert is excised from the recombinant bacteriophage and subcloned in phagemid vectors. An additional 280 bp at the 5' end of the cDNA are cloned by polymerase chain reaction (PCR) amplification of the 5' end of the SU1 mRNA. Thus the total length of the SU1 cDNA clone is approximately 2.7 kb, which, depending on the length of the poly(A) tail, comprises either the complete or nearly complete mRNA sequence.

Figure 11:
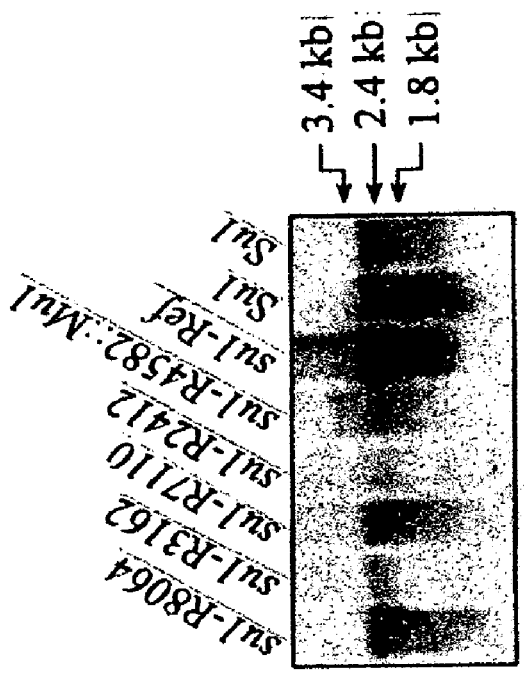
FIG. 11 shows detection of SU1 mRNA.

Transcription of the Su1 gene locus is examined in normal kernels and sugary kernels homozygous for various SU1 mutations, using as a probe a portion of the SU1 cDNA. FIG. 11 illustrates detection of SU1 mRNA. Total RNA isolated 20 days after pollination from kernels homozygous for the indicated mutation (10 mg per sample) is separated by electrophoresis and probed with fragment EE1780 from the SU1 cDNA. The SU1/SU1 kernels are from two different standard lines, F1 hybrid B77/B79 (right-most lane) and F1 hybrid Q66/Q67 (second lane from the right). Arrows indicate the mobility in the same agarose gel of standards of known nucleotide sequence.

As shown in FIG. 11, in RNA gel blot analysis the cDNA probe EE1780 detected a 2.8 kb mRNA in normal kernels harvested 20 days after pollination. The transcription pattern is identical to that detected by hybridization with the genomic probe BE1000. The 2.8-kb transcript is missing or severely reduced in concentration in kernels homozygous for SU1-R4582::Mu1, SU1-R2412, SU1-R7110, or SU1-R3162, whereas transcripts of about this length are present in kernels homozygous SU1-R8064 or SU1-Ref at seemingly normal levels.

EXAMPLE III

Preparation of Fusion Proteins

The glutathione S-transferase (GST) gene fusion system (Pharmacia Biotech) can be used for the expression and purification of portions of the protein (SU1) coded for by the maize gene sugary1 (SU1). The pGEX plasmids designed for this system enable inducible, high-level intracellular expression of genes or gene fragments as fusions with *Schistosoma japonicum* GST. These vectors carry a multiple cloning region to facilitate fusion of a gene fragment to the C-terminus of GST, a tac promoter inducible by the gratuitous lactose analog IPTG, and an internal lac Iq gene for use in any *E. coli* host. Because GST binds reversibly and with high affinity to glutathione, purification of a fusion protein can be accomplished by incubation with a glutathione-affinity matrix such as glutathione-agarose.

Two fragments of the SU1 cDNA are used to create fusion proteins. The first construct, termed pAR1, comprises an internal 1.8 kb region of the SU1 cDNA that when used as a probe in Southern gel blot analyses recognized multiple regions of maize genomic DNA. The second construct, termed pAR2, comprises a smaller 0.6 kb region of the same SU1 fragment used in pAR1. This smaller fragment represents a unique region of maize genomic DNA. The vector pGEX-4T-3 (4.97 kb) is chosen for each construct because it contained an EcoRI site in the multiple cloning region that would enable the SU1 cDNA to be transcribed in the proper frame.

A 1782 bp EcoRI fragment from the SU1 cDNA subclone pMJ67 (nt 289–nt 2071) was used to make pAR1. This fragment was cloned into the unique EcoRI site of vector pGEX-4T-3 to construct the 6.8 kb pAR1 plasmid. The fusion protein expressed by pAR1, designated GST-SU1-T1, is predicted to contain 594 amino acids of SU1 and to have a size of 93 kD, including the 27.5 kD GST protein. pAR2 was created by deleting all but 595 bp from the 5' end of the SU1 EcoRI fragment (nt 289–nt 864) that is used for the construction of pAR1. For this construct, the SU1 region downstream of nt 864 was removed by digestion of pAR1 with HindIII (at nt 864 in the SU1 cDNA) and SalI (a site within the multiple cloning region of the vector). Following removal of this fragment, the remaining portion of pAR1 which contained the vector and 595 bp of SU1 cDNA was purified, treated with the Klenow fragment of DNA polymerase to produce blunt ends, and self-ligated to produce pAR2 (5.6 kb). The fusion protein from pAR2, designated GST-SU1-T2, is predicted to contain 192 amino acids from SU1 and to have a size of 49 kD, including the 27.5 kD GST.

Recombinant plasmids pAR1 and pAR2 were grown in the E. coli host strain TG-1. For large scale preparation, a host colony containing either plasmid pAR1 or pAR2 is grown at 30° C. overnight in 100 ml 2XYT media containing 25 µg/ml ampicillin. This culture is used to inoculate 1 liter of the same medium, which is grown at 30° C. until the cells reached an $OD_{600}$ of approximately 1.0. Expression of the fusion protein is then induced by the addition of isopropyl-lthiogalactoside (IPTG) to a concentration of 0.1 mM and incubation at 30° C. for 2 hr. Proteins are harvested from crude bacterial lysates generated by enzymatic digestion with lysozyme. Fusion proteins GST-SU1-T1 and GST-SU1-T2 are purified by passage of the cell lysate over glutathione-agarose affinity columns. Proteins are analyzed by sodium dodecylsulfate polyacrylamide gel electrophoresis (SDS-PAGE) followed by staining with Coomassie blue, and by immunoblot analysis using an ECL chemiluminescent system (Amersham) with anti-GST antibody (Molecular Probes, Inc.) as the primary antibody and anti-rabbit IgG horseradish peroxidase conjugate (BioRad Laboratories) as the secondary antibody. Both GST-SU1-T1 and GST-SU1-T2 were detected by these means and each was of the predicted size.

EXAMPLE IV

Expression of Recombinant SU1 and Purification to Apparent Homogeneity

In an alternative embodiment, SU1 protein (SU1) can be expressed in E. coli using the pET Expression System (Novagen). This system utilizes the bacteriophage T7 promoter to drive expression of a recombinant protein and offers the means for efficient detection and purification of the protein. Expression of full-length or near full-length SU1 enables an in vitro analysis of the biochemical function of the protein, specifically its ability to hydrolyze branched polysaccharide.

Two constructs have been designed to express the recombinant SU1 protein. The first contains the near full-length cDNA, beginning at nt 289 of the SU1 cDNA (an EcoRI site in the adaptor of the lambda cDNA clone) and terminating at nt 2616 (an XhoI site). The second contains the full-length cDNA, beginning at nt 86 (an NcoI site that contains the putative translation start signal) and terminating at nt 2616 (XhoI site). The XhoI site is in the 3' region of the cDNA past the transnational stop codons. The vector pET-29b(+) is chosen for both constructs because the SU1 cDNA is transcribed in the correct reading frame when either EcoRI or NcoI is used as a cloning site. This vector contains the bacteriophage T7 promoter and terminator sequences, and a lac operator sequence. To aid in detection and purification, pET-29b(+) contains both a His-Tag sequence and an S-Tag sequence. The His-Tag sequence allows the recombinant protein to be purified by metal chelation chromatography, and the S-Tag sequence allows the protein to be affinity-purified with ribonuclease S-protein and quantified with a homogeneous assay.

Fusion proteins produced with the above assays are cleaved using a protease, such as thrombin, and the products purified by chromatography. The pET-29b(+) vector contains a thrombin cleavage site that can be used to remove the upstream S-Tag by digestion with the site-specific protease thrombin.

Cloning of either the 2327 bp EcoRI/XhoI region or the 2530 bp NcoI/XhoI region of the SU1 cDNA into pET-29b (+) requires some initial subcloning manipulations which are within the skills of the ordinary skilled practicioner. This is because a portion of the 5' end of the SU1 cDNA is obtained by RACE-PCR amplification, and exists as a separate clone. In addition, the SU1 cDNA contains an internal EcoRI site (at nt 2061).

The 2327 bp EcoRI/XhoI region can be united and cloned into pET-29b(+) by first digesting pAR1 with KpnI, which cuts at a unique site within the SU1 sequence, and XhoI, which cuts at a unique site within the multiple cloning region of the vector, to remove the 1315 bp KpnI-XhoI fragment. pMJ99, which contains a 2.9 kb KpnI insert from the lambda SU1 cDNA clone in pUC119, is digested with KpnI and XhoI to release the 1858 bp KpnI/XhoI 3' region of the SU1 cDNA. The 1858 bp KpnI-XhoI fragment excised from pMJ99 is ligated to the KpnI-, XhoI-digested pAR1. This last construct, designated pAR3, is partially digested with EcoRI and XhoI to release the 2327 bp EcoRI/XhoI fragment for ligation to EcoRI-, XhoI-digested pET-29b(+). This final clone is designated pAR4.

Cloning of the 2530 bp NcoI/XhoI region of SU1 cDNA into pET-29b(+) is achieved by first digesting pMJ125, which contains the SU1 5' RACE-PCR product as a 620 bp EcoRI/BamHI fragment in pUC119, with NcoI and PmlI to release and purify the 425 bp NcoI/PmlI fragment. The 425 bp fragment is cloned into NcoI-, PmlI-digested pAR4.

A near-full length version of SU1 (termed SU1r, for SU1 recombinant protein) was expressed in E. coli using the second construct described above. SU1r was produced initially as a fusion protein consisting of SU1 residues 68 through the carboxy terminus, plus a 33-residue N-terminal sequence which included an S-tag useful for affinity purification followed by a thrombin proteolytic cleavage site. The N-terminal region of SU1 missing in the fusion protein is not represented in bacterial isoamylase, and thus may comprise most of a transit peptide responsible for targeting the protein to the amyloplast. SU1r, therefore, is expected to be very close in structure to mature SU1 as it exists in maize endosperm, and to possess the catalytic activities of the native enzyme.

Figure 12A:
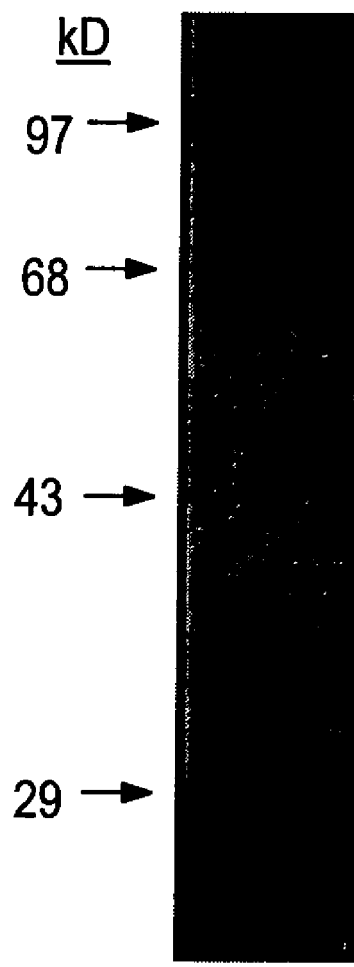
FIGS. 12A and 12B show SDS-PAGE analysis of purified SU1r by silver stain and immunoblot analysis with anti-SU1, respectively.
Figure 12B:
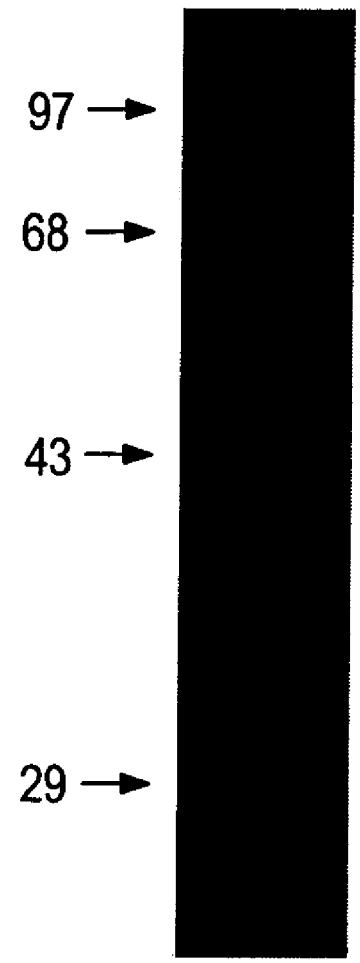

Inducible expression of a fusion protein of approximately 75 kD was detected in both the soluble and insoluble fractions of crude E. coli cell extracts by SDS-PAGE, and was identified specifically as SU1r by immunoblot analysis using anti-SU1 (see Example VIII). Equivalent protein fractions from uninduced E. coli cells and also from induced E. coli cells harboring the empty plasmid pET-29(b)+ served as negative controls. SU1r was purified from the total soluble extracts by means of the affinity of the fused S-tag region for S-protein derived from ribonuclease A (Novagen), and was released from the affinity matrix by cleavage with thrombin. As shown in FIGS. 12A and 12B, analysis of the purified material by SDS-PAGE revealed a single polypeptide of ~75 kD on a silver stained gel, and immunoblot analysis with anti-SU1 also identified a 75 kD protein. The expressed protein is approximately the size predicted by the SU1 cDNA sequence, and at this sensitive level of detection appears to be free of contaminating proteins.

EXAMPLE V

SU1r Cleaves α-(16) Branch Linkages

Recombinant SU1 protein was tested for the ability to hydrolyze various branched polysaccharide using assays to measure the release of glucose from dextrin and the release of various reducing sugars from amylopectin and/or glycogen (Fox et al., 1991). In addition, these tests were also used to determine the reducing value of pullulan, an ordered glucopolysaccharide.

Figure 13A:
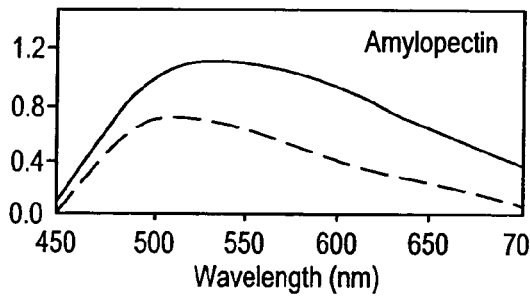
FIGS. 13A–13D show absorption spectra of glucan-iodine complexes, formed upon the incubation of SU1r with amylopectin, β-limit dextrin, glycogen and phytoglycogen, respectively. The indicated substrates were incubated with SU1r, and aliquots of the reaction mixtures were combined with $I_2$/KI stain. Spectra were recorded prior to addition of SU1r (dashed lines) and after 1 h incubation (solid lines)
Figure 13B:
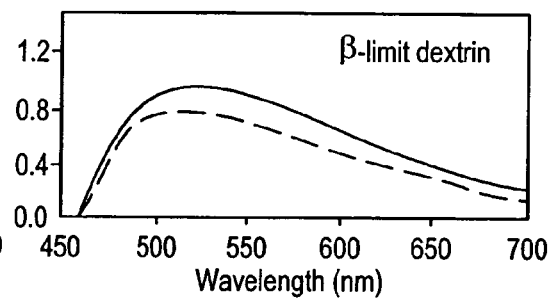
Figure 13C:
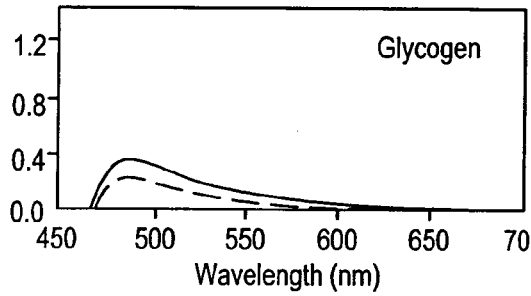
Figure 13D:
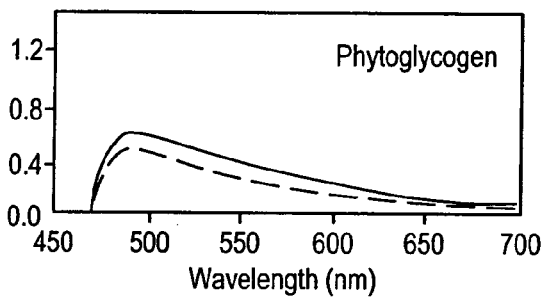

SU1r was found to possess debranching enzyme activity. As shown in FIGS. 13A–13D, purified SU1r cleaves, presumably by hydrolysis, the α-(1→6) branch linkages of amylopectin, the β-limit dextrin of amylopectin, oyster glycogen, and maize phytoglycogen, as measured by an increase in the maximal absorbance (blue-value) of the glucan-iodine complex after treatment with the enzyme. In the case of amylopectin, a shift also occurred in the wavelength at which the complex exhibited maximal absorbance ($\lambda$max). Increased blue-value reflects greater linearity of the polysaccharide, and a shift in the $\lambda$max normally indicates that the reaction product consists of longer unbranched chains (Banks et al., 1971). Incubation of amylopectin with SU1r for one hour resulted in an increase in blue-value of 0.5 absorbance units at 550 nm, as well as a shift in the $\lambda$max from 520 nm to 550 nm (FIG. 13A). Thus, SU1r was shown to hydrolyze branch linkages within amylopectin, producing linear molecules with longer effective chain lengths which complexed more readily with iodine. As can be seen in FIGS. 13B–13D, smaller increases in blue-value also resulted from a similar incubation of SU1r with the β-limit dextrin of amylopectin (0.15 units at 520 nm), and both oyster glycogen and maize phytoglycogen (0.15 units at 470 nm), although in each instance there was little or no shift in $\lambda$max. A constant $\lambda$max also is observed after debranching of glycogen with Ps. isoamylase, presumably due to the overall shorter and more uniform chain lengths in the glycogen molecule (Yokobayashi et al., 1970). Although changes in iodine staining capacity cannot be quantitatively related, these experiments indicate that β-limit dextrin, glycogen, and phytoglycogen are poorer substrates than amylopectin for SU1r debranching activity.

Figure 14:
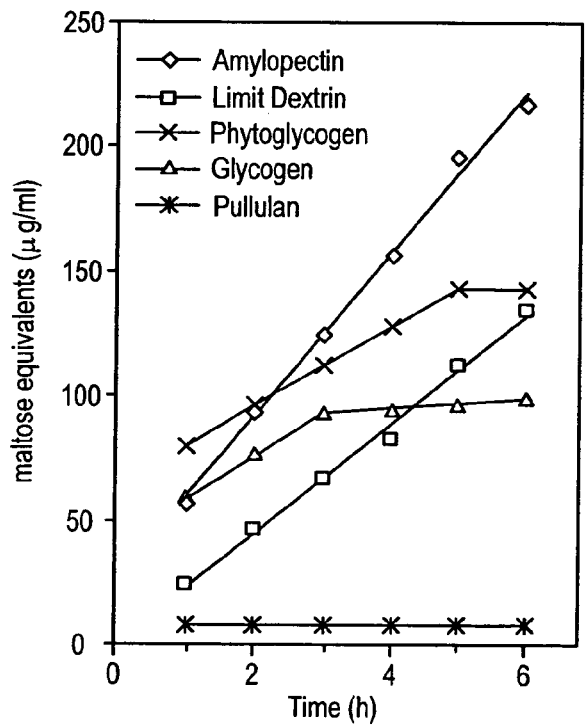
FIG. 14 is a graph showing hydrolytic activity of SU1r toward amylopectin, β-limit dextrin, phytoglycogen, glycogen and pullulan. The indicated polysaccharides were incubated with SU1r, and the concentration of reducing ends present in the reaction mixtures was determined in terms of μg maltose equivalents/mL.

The substrate preference of SU1r was confirmed by means of a quantitative colorimetric assay that measures increases in the reducing value of the reaction products relative to the substrate. The formation of new reducing ends was assessed hourly over the course of a six hour incubation period of various substrates with SU1r. Referring to FIG. 14, again, SU1r was shown to have the greatest activity towards amylopectin, with the number of reducing ends formed increasing linearly for the entire incubation period. Hydrolysis of β-limit dextrin proceeded in a similar manner but at a slower rate. Production of reducing ends during the incubation of phytoglycogen and glycogen with SU1r increased at a reduced rate relative to either amylopectin or its β-limit dextrin, and leveled off after five hours and three hours, respectively. There were no new reducing ends formed during the incubation of pullulan with SU1r, indicating that SU1r is unable to hydrolyze α-(1→6) glycoside bonds in this substrate. These results were supported by TLC analysis of the products of the pullulan/SU1r reaction, which indicated that no maltotriose was released. The specific activities of SU1r towards each of the substrates tested is provided in Table II, as well as a comparison of the activities relative to that for amylopectin. These calculations show that SU1r specific activity is 1.6-fold higher for amylopectin than for β-limit dextrin, and 4-fold higher than for either phytoglycogen or oyster glycogen. The finding that SU1r has DBE activity towards each of the substrates tested except pullulan classifies it as an isoamylase rather than a pullulanase type of DBE. The Su1 gene product, therefore, is referred to as SU1 isoamylase.

TABLE II

Substrate specificity of SU1r

| Substrate | Specific Activity[a] | Relative Activity (%)[b] |
|---|---|---|
| Amylopectin | 3.34 | 100 |
| β-limit dextrin | 2.04 | 61 |
| Phytoglycogen | 0.74 | 22 |
| Oyster glycogen | 0.74 | 22 |
| Pullulan | 0 | 0 |

[a]Specific activity units are $\mu$ mol maltose equivalents/min/mg protein
[b]Activity toward amylopectin is set at 100%

SU1r activity toward branched cyclodextrins containing either glucosyl or maltosyl side chains also was tested. Cycloheptaose (also termed β-Schardinger dextrin) to which a glucosyl or a maltosyl branch was attached by an α-(1→6) linkage (termed glucosyl-cycloheptaamylose, Glc-cGlc7, and maltosyl-cycloheptaamylose, Glc2-cGlc7, respectively) was incubated with SU1r, and the reducing value of the product was measured over time. No increase was seen in the number of reducing ends following the incubation of either Glc-cGlc7 or Glc2-cGlc7 with SU1r, indicating that SU1r is unable to hydrolyze the α-(1→6) linkage between the glucosyl or maltosyl side chain and the cyclodextrin. These results suggest that SU1 requires a chain length of greater than two glucose units as a minimal substrate for its presumed hydrolytic activity. This interpretation is supported by TLC analysis of the products of the β-limit dextrin/SU1r reaction, in which no maltose was released.

EXAMPLE VI

Properties of SU1r Isoamylase

The debranching activity of SU1r toward amylopectin, as measured by the changes in reducing value, occurred only within the narrow range of relatively neutral pH, from pH 5.5 to pH 8.0. SU1r was incubated with amylopectin in buffers adjusted to pH values from 3–10, and activity was determined at 30° C. As can be seen in FIG. 15A, maximal activity occurred at pH 6.0. At this optimal pH value, as can be seen in FIG. 15B, SU1r hydrolyzed branch linkages in amylopectin at temperatures between 15° C. and 40° C., with maximal activity occurring at approximately 30° C. SU1r was completely inactive at 50° C. and above. Thermal stability of SU1r was tested by a 10 minute pre-incubation of the enzyme at temperatures ranging from 30° C. to 60° C., followed by assessment of its activity toward amylopectin at 30° C. As shown in FIG. 15C, the results mirrored those of the thermal activity tests, indicating that enzyme stability declined until it was lost at 50° C.

Neither divalent cations nor sulfhydryl agents were required for the activity of SU1r. Although SU1r enzymatic reactions were conducted routinely in buffers devoid of divalent cations, the addition of either 10 mM $Ca^{2+}$ or 10 mM $Mg^{2+}$ to the buffer did not alter SU1r activity. SU1r activity was not dependent on residual $Ca^{2+}$, because addition of 10 mM EDTA to the reaction buffer did not alter the reaction rate. Maintenance of enzyme stability did require the addition of 5 mM DTT to the storage buffer.

EXAMPLE VII

Products of SU1r Hydrolysis

The debranching activity of SU1r was characterized further by analysis of the linear chains released from amylopectin following digestion with the recombinant enzyme. The chain length profile obtained after treatment of amylopectin from wx-mutant maize with SU1r for 1 h, as determined by HPAEC-ENZ-PAD, is shown in FIG. 16. This pattern is very similar to that obtained after an analogous treatment of the same substrate with isoamylase from *Pseudomonas*, and to that reported by others for the complete debranching of amylopectin by Ps. isoamylase (Wong and Jane, 1995; Wong and Jane, 1997). These results lend further support to the identification of SU1 as an isoamylase.

Figure 17:
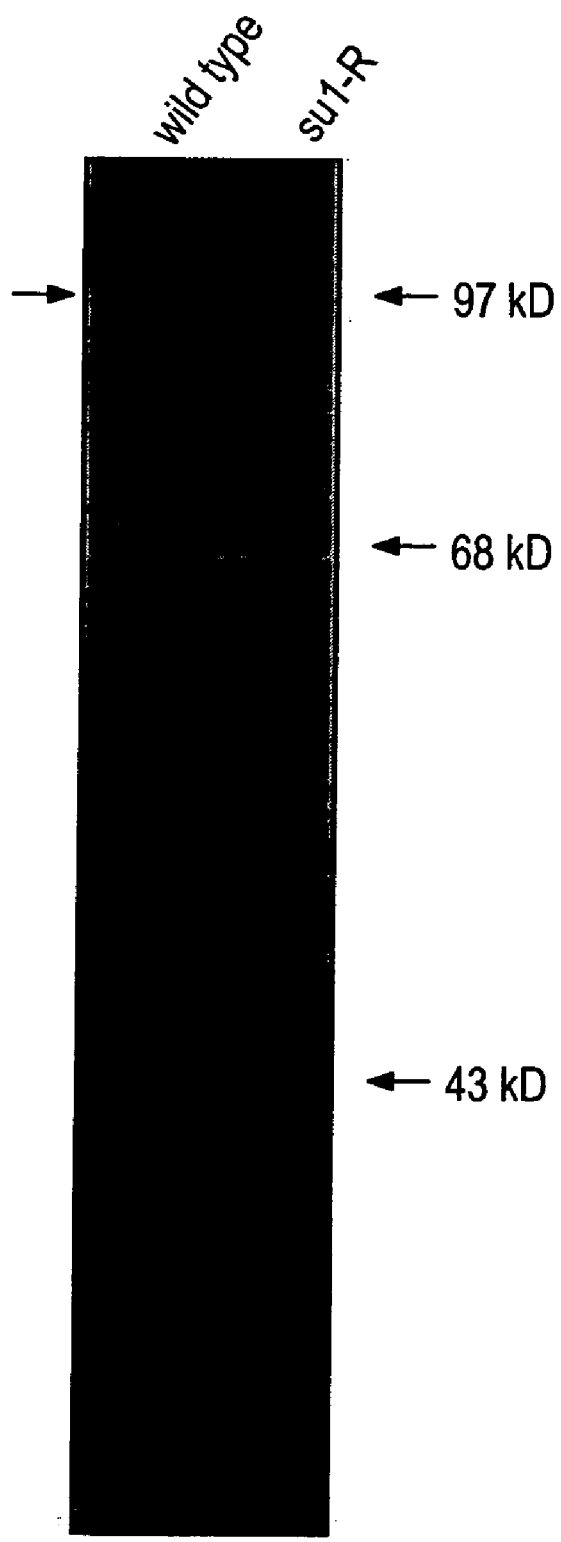
FIG. 17 shows immunoblot analysis with rice R-enzyme antibody of total protein extracts from wild type and homozygous SU1-R mutant kernels.

The enzymatic properties of SU1r are distinct from those of the pullulanase that is deficient in SU1-mutant endosperm. Specifically, SU1r fails to hydrolyze pullulan whereas the activity characterized previously was defined using pullulan as the substrate (Pan and Nelson, 1984). To investigate this apparent discrepancy, endosperm extracts were examined for the presence of a pullulanase whose expression might be dependent on SU1 function. An antiserum raised against purified R-enzyme from rice endosperm (Nakamura et al., 1996a) was used to detect antigenically related proteins in extracts from wild type maize endosperm harvested 20 DAP. As shown in FIG. 17, this antiserum identified four polypeptides in immunoblot analysis, one of which was approximately 100 kD in size and thus coincided with the 105 kD molecular weight known for the native R-enzyme in rice (Nakamura et al., 1996a; Toguri, 1991). A similar analysis of extracts from homozygous SU1-R kernels revealed that the 100 kD protein is deficient specifically in the mutant, although some smaller-sized polypeptides were detected in both the wild type and mutant extracts. These data indicate that a pullulanase structurally related to the rice R enzyme exists in maize and that accumulation of this pullulanase is specifically affected, either directly or indirectly, by Su1-mutations. Investigation of the physical association of the maize pullulanase with starch granules by immunoblot analysis revealed that, like SU1 isoamylase, it is a soluble endosperm protein. Further support for the conclusion that a rice R-enzyme homolog exists in maize was gained by isolating a full length cDNA clone for the pullulanase from a maize endosperm cDNA library. This cDNA is extremely similar in nucleotide sequence to the rice R-enzyme cDNA of Nakamura et al. (Nakamura et al., 1996a), and maps independent of SU1 to chromosome 2.

EXAMPLE VIII

Preparation of Polyclonal Antibodies and Immunological Identification of Native SU1

To prepare polycolonal antibodies reactive with SU1, host animals, such as New Zealand White rabbits, are inoculated with SU1 fusion protein, such as GST-SU1-T1 or GST-SU1-T2, which has been purified from *E. coli* lysates by affinity chromatography with glutathione-agarose. An initial intramuscular injection of 300 µg protein emulsified in Freund's complete adjuvant is followed by two to three booster injections with 200 µg protein emulsified in Freund's incomplete adjuvant. Sera from sample test bleeds harvested after one week each boost is tested for SU1 specificity by immunoblot analysis The sera is used as primary antibody to detect, e.g., purified GST-SU1-T1 and GST-SU1-T2 proteins as well as total proteins extracted from maize endosperms harvested 20 days after pollination (DAP). This is a tissue and time period when the Su1 gene is known to be transcribed, according to Northern gel blot analysis.

In practice, polyclonal antibodies were raised against the fusion protein GST-SU1-T2, described in Example III. As shown in FIG. 18A, the presence of high-titer antibodies in the crude antiserum that specifically recognized SU1 was demonstrated by immunoblot analysis of soluble extracts from *E. coli* cells expressing the GST-SU1 fusion protein. Antibodies specific for SU1 were purified from the crude serum by means of their affinity for near full-length recombinant SU1 immobilized on nitrocellulose filters. The resultant antibody fraction was termed anti-SU1.

Referring to FIG. 18B, anti-SU1 identified a protein of approximately 79 kD in immunoblot analysis of total soluble extracts from maize kernels collected 20 days after pollination (DAP). This protein was not detected in extracts of kernels homozygous for either of two independent SU1-mutations, the reference allele SU1-Ref (Correns, 1901) or the transposon insertion allele SU1-R4582::Mu1 (James et al., 1995). These data, together with previous characterizations of the cloned Su1 gene (James et al., 1995), indicate that the 79 kD protein is, in fact, native SU1. The 79 kD size of the protein is approximately that predicted for native SU1 based on the length of the SU1 cDNA, considering the likely removal of an amyloplast targeting peptide.

Investigation of the physical association of SU1 with starch granules revealed that it is exclusively a soluble endosperm protein. Proteins from maize endosperm cells collected 20 DAP were separated into those bound to starch granules and those in the post-granule fraction (pellet). As shown in FIG. 18C, immunoblot analysis indicated that SU1 is present solely in the post-granule fraction. These results suggest that SU1 acts at the surface of the granule or within the amyloplast stroma, rather than within the granule interior or tightly bound to a substrate that is integral to the granule.

The expression pattern of SU1 during the course of endosperm development was determined by RNA gel blot analysis and also by immunoblot analysis using anti-SU1. Referring to FIG. 19B, anti-SU1 detected the 79 kD protein in extracts from kernels harvested 10–30 DAP; this protein was present in nearly constant abundance throughout this time period. However, the 79 kD protein was not detected in extracts from 6 DAP kernels. These results were supported by an analysis of SU1 transcript accumulation in kernels harvested soon after pollination. As can be seen in FIG. 19A, gel blots of RNAs isolated from kernels 8–20 DAP showed that the SU1 transcript was present at a relatively constant level during this period. Thus, SU1 is present in the endosperm coincident with the initiation of starch biosynthesis, and persists at a high level throughout the time period of starch accumulation.

EXAMPLE IX

Preparation of Monoclonal Antibodies

Monoclonal antibodies reactive with SU1 can be prepared by according to methods known in the art (e.g., Milstein, Sci. Amer. 243:66–64 (1980); Kohler, Science 233:1281–1286 (1986); Milstein, Science 231:1261–1268 (1986)). Briefly, a mouse can be immunized with SU1 protein or a fragment thereof, and its spleen removed several weeks later. A mixture of lymphocytes and plasma cells from this spleen can be fused in in vitro with myeloma cells by exposing them to polyethylene glycol, a polymer that induces cell fusion. A mutant myeloma cell line lacking hypoxanthine-guanosine phosphoribosyl transferase (HG-PRT) can be used to enable hybrids to be easily selected. The cells can be grown in a medium containing hypoxanthine, aminopterin (methotrexate), and thymine (HAT medium) to kill unfused myeloma cells. The hybridoma cells so produced and their progeny indefinitely produce large amounts of the homogeneous antibody specified by the parent cell from the spleen and can be grown in wells in tissue culture plates. Supernatants from these wells can be screened for the presence of antibody molecules specific for the antigen of interest. The cells in positive wells are cloned and screened again to obtain hybridomas of a single type which produce the antibody of interest.

EXAMPLE X

Purification of Native SU1 from Maize Endosperm

A crude maize endosperm extract was prepared form maize kernels harvested 20 days after pollination. The protein fraction was precipitated with 40% ammonium sulfate, dialyzed and then subjected to anion exchange chromatography on a Q Sepharose Fast Flow column (Pharmacia).

Figure 20A:
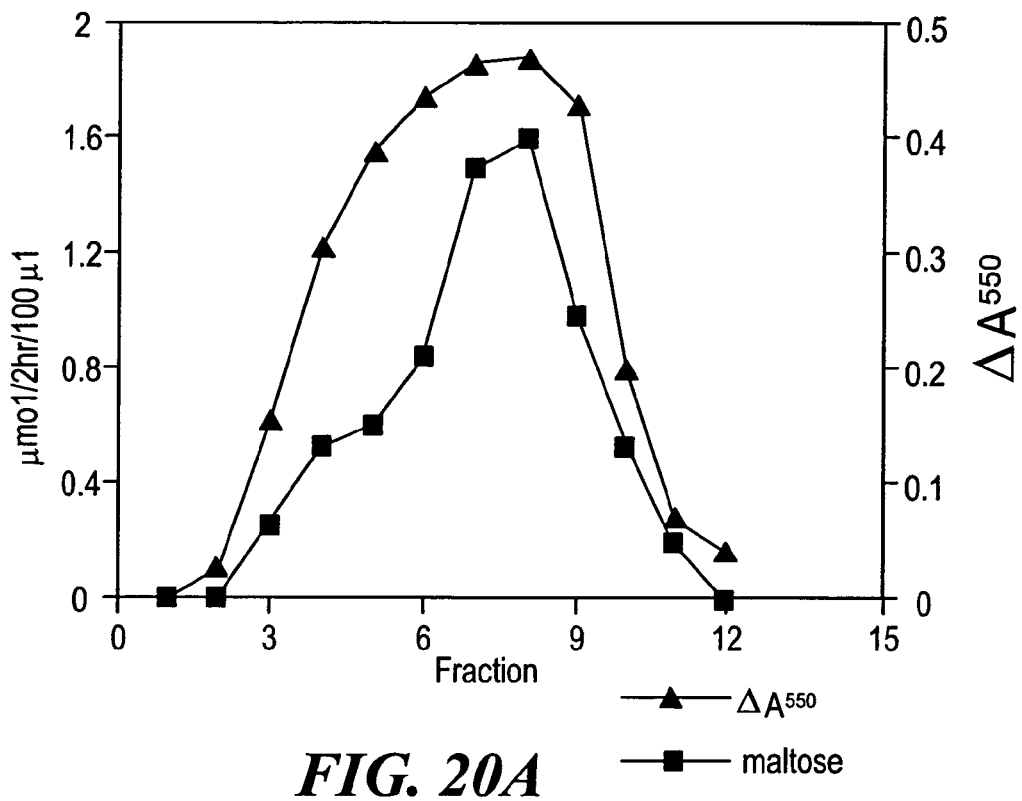
FIGS. 20A and 20B show purification of SU1 by gel filtration chromatography.
Figure 20B:
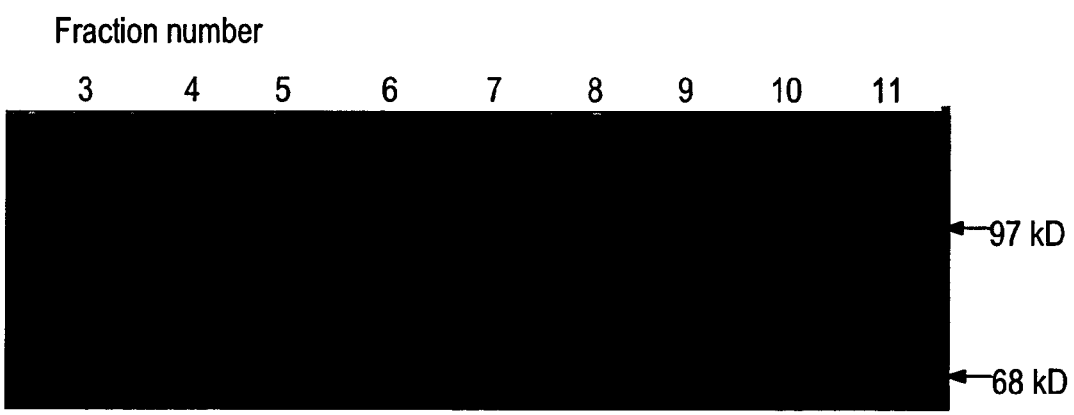

Two protocols were then used for further isolation of SU1, referred to as purifications A and B. In purification A, Q Sepharose fractions containing SU1 activity were pooled, and the proteins therein were fractionated further by gel permeation chromatography on Sepharcryl S-200. Eluted fractions were assayed for the ability to hydrolyze amylopectin and to change the blue value of the glucan-iodine complex obtained after amylopectin digestion. As shown in FIG. 20A, a single peak of DBE activity was obtained, which eluted in the void volume prior to the 670,000 kD molecular weight marker. The fractions were next subjected to immunoblot analysis with anti-SU1. As shown in FIG. 20B, fractions that contained DBE activity also contained an anti-SU1-reactive protein, and no immunoblot signal was detected in any fraction lacking this enzyme activity.

Figure 21A:
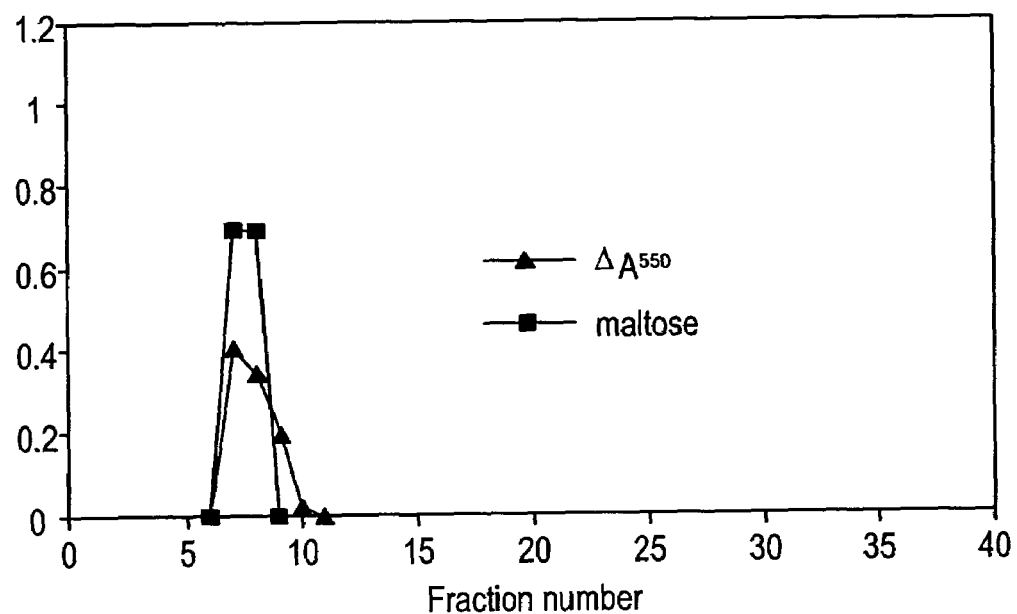
FIGS. 21A and 21B show purification of the pooled SU1 fraction by Mono Q column chromatography.
Figure 21B:
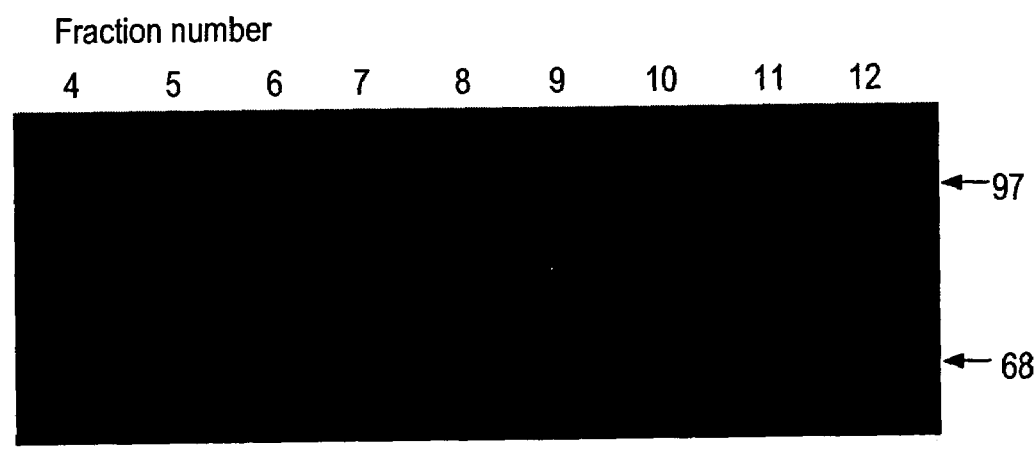

Proteins in the pooled Sephacryl fractions containing DBE activity were subjected to another anion exchange chromatography separation, using the matrix Mono Q. Again, the DBE activity cofractionated precisely with a protein bound by anti-SU1 antibodies in immunoblot analysis, as shown in FIGS. 21A and 21B. SDS-PAGE and Comassie blue staining of the DBE-containing fractions revealed several bands, among which the most prevalent was a 81 kD protein that migrated at the same rate as the anti-SU1-reactive polypeptide. The results of purification A are summarized in Table III. The DBE activity was 32-fold purified with a specific activity of 2.89 units.

TABLE III

Purification of SU1

| Steps | Total Protein | Total Activity ($\mu$mol min$^{-1}$) | Specific Activity ($\mu$mol min$^{-1}$ mg$^{-1}$) | Purification (Fold) | Recovery (%) |
|---|---|---|---|---|---|
| Crude Extract | 328 | 29.52 | 0.09 | ND[a] | ND[a] |
| Ammonium Sulphate | 146 | 12.41 | 0.085 | 1 | 100 |
| Q Sepharose | 8 | 6.16 | 0.77 | 9.10 | 50 |
| Gel filtration | 2.80 | 3.78 | 1.35 | 15.90 | 30 |
| Mono Q | .36 | 1 | 2.89 | 34.00 | 8 |

[a]Not determined

Figure 22A:
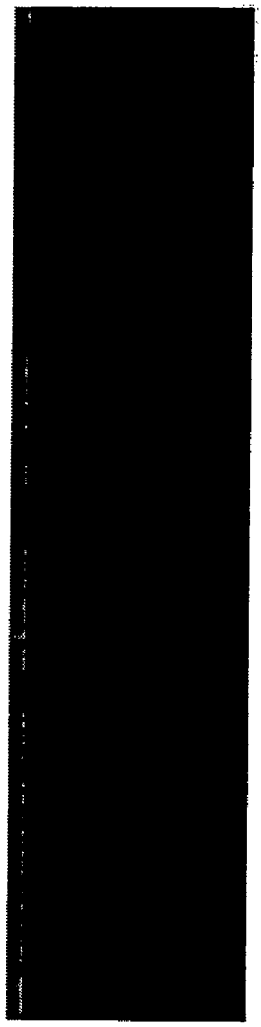
FIGS. 22A and 22B shows silver staining and anti-SU1 immunoblot analysis of affinity purified native SU1 following SDS-PAGE.
Figure 22B:
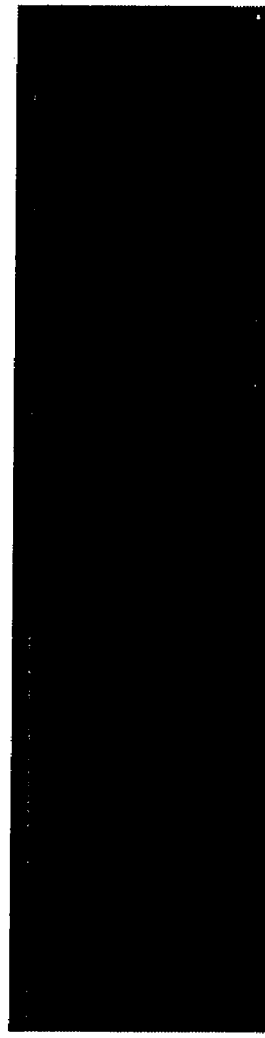

In purification B the pooled Q Sepharose fractions were applied to a soluble starch affinity matrix and bound proteins were eluted with free maltotriose. As can be seen in FIGS. 22A and 22B, only a single protein was evident when the eluted fractions containing DBE activity were analyzed by SDS-PAGE and silver staining. This protein reacted with anti-SU1 in immunoblot analysis.

EXAMPLE XI

N-Terminal Sequencing of Purified Native SU1

A portion of the most pure SU1 peak fractions eluted from the Mono Q column were separated by SDS-PAGE and blotted onto a PVDF membrane (Bio-Rad). The band corresponding in size to the anti-SU1-reactive protein was excised from the membrane and subjected to N-terminal peptide sequencing. The N-terminal sequence of this protein was found to be VAEAVQAEED. The underlined residues indicate that most abundant amino acid detected in each sequencing cycle. The sequence of the underlined residues corresponds precisely to the region of SU1 isoamylase spanning positions 50–59. the other residues in this region of the peptide were detected as minor components in the sequencing data. These results provide a direct demonstration that the purified isoamlyase-type DBE is SU1 isoamylase. Furthermore, mature SU1 isoamylase is formed by proteolytic cleavage between residues 49 and 50, presumably during transport into the amyloplast where this DBE is known to be located (Yu et al., 1998), indicating an N-terminal transit peptide of 49 amino acids. The molecular mass of mature SU1 isoamylase calculated from the deduced amino acid sequence and the known mature N terminus is 81 kD, which matches closely with that observed when this DBE was detected by immunoblot analysis in total endosperm extracts.

EXAMPLE XII

Analysis of the Multimeric Structure of SU1

SU1 is predicted to be a multimeric enzyme, because the molecular mass of the enzyme is greater than 670,000 kD, whereas that of the monomer polypeptide is 81 kD. Furthermore, the purified enzyme contains only a single polypeptide, indicative of a homomultimeric quaternary structure. These considerations suggest that SU1 polypeptides are able to bind directly to each other and form a stable complex. This prediction was tested using the yeast two-hybrid system.

Figure 23:
FIG. 23 shows Sugary1 two-hybrid constructs.
Figure 24:
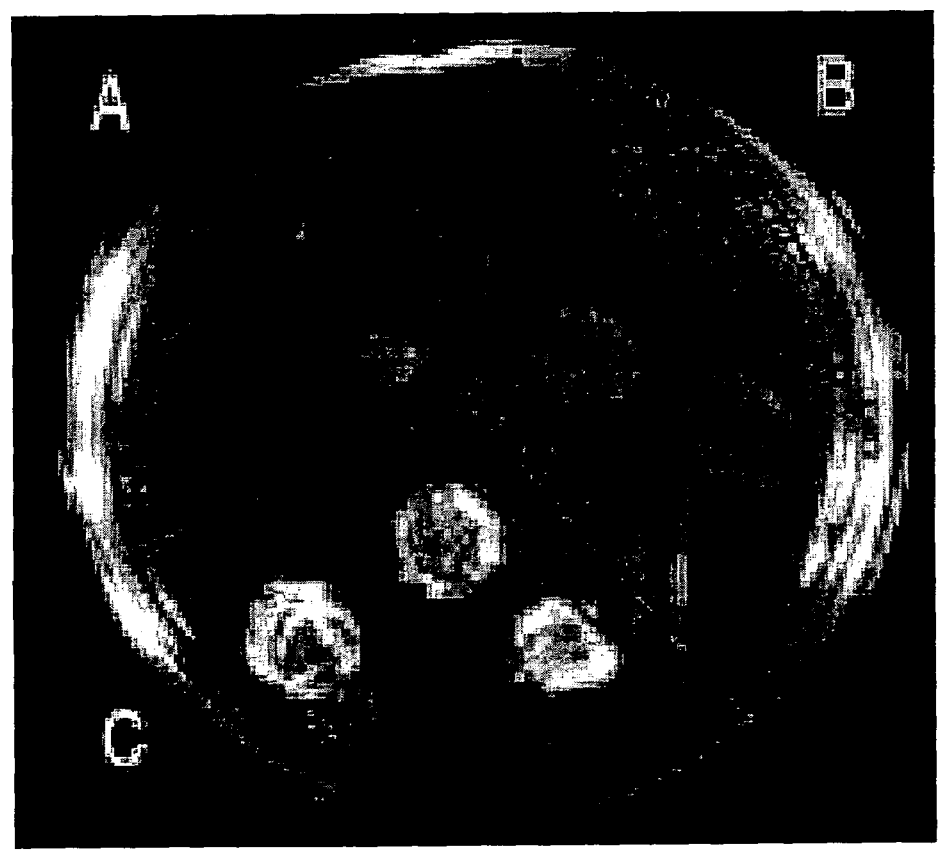
FIG. 24 shows two-hybrid analysis of SU1:SU1 physical interaction. Cotransformation of yeast strain PJ69-4A with plasmid constructs in which SU1 was fused to the Gal4 binding domain and the Gla4 activation domain, respectively, resulted in growth on selective Ade, -Met media (A). In control transformations, either plasmid by itself failed to activate the reporters (B and C).

As illustrated in FIG. 23, the portion of SU1 from residue 69 of the primary translation product to C-terminal residue 789 was fused to the C-terminus of either the transcriptional activation domain or DNA binding domain of the yeast transcription factor GAL4. These fusion proteins, therefore, contain all of the mature SU1 amino acid sequence except for the N-terminal residues. As shown in FIG. 24, introduction of the two different hybrid proteins into the same yeast cells activated transcription of the resident GLA4-dependent reporter genes. In contrast, either the binding domain plasmid or the activation domain plasmid alone failed to induce reporter transcription. These data indicate that separate SU1 polypeptides are capable of binding to each other and forming multisubunit complex.

EXAMPLE XIII

Development of Transgenic Plants with Modified Expression of SU1

Plasmid vectors were constructed that utilized the maize zein promoter to drive the expression of the SU1 cDNA in the maize kernel specifically during the developmental time period during which starch is synthesized. These vectors also included the maize Adh1 intron to enhance gene expression and the nos 3' region from *Agrobacterium tumefaciens* to ensure proper transcription termination. The entire SU1 cDNA was cloned into these vectors in either the sense or antisense orientation. The first 147 nucleotides of the cDNA code for a transit peptide predicted to target the SU1 protein to the amyloplast, the subcellular compartment in which starch is synthesized. Control plasmids lacking SU1 were also constructed. Additionally, plasmids were designed to constitutively express the *Streptomyces* bar gene as a selectable marker.

The SU1 and bar expression plasmids were co-delivered to maize embryogenic calli from the High II line (a hybrid of A188 and B73) by microprojectile bombardment. Transformed calli were selected, regenerated to seedlings, and the $R_0$ seedlings were transferred to the greenhouse for propagation, crossing, and analysis.

Figure 25:
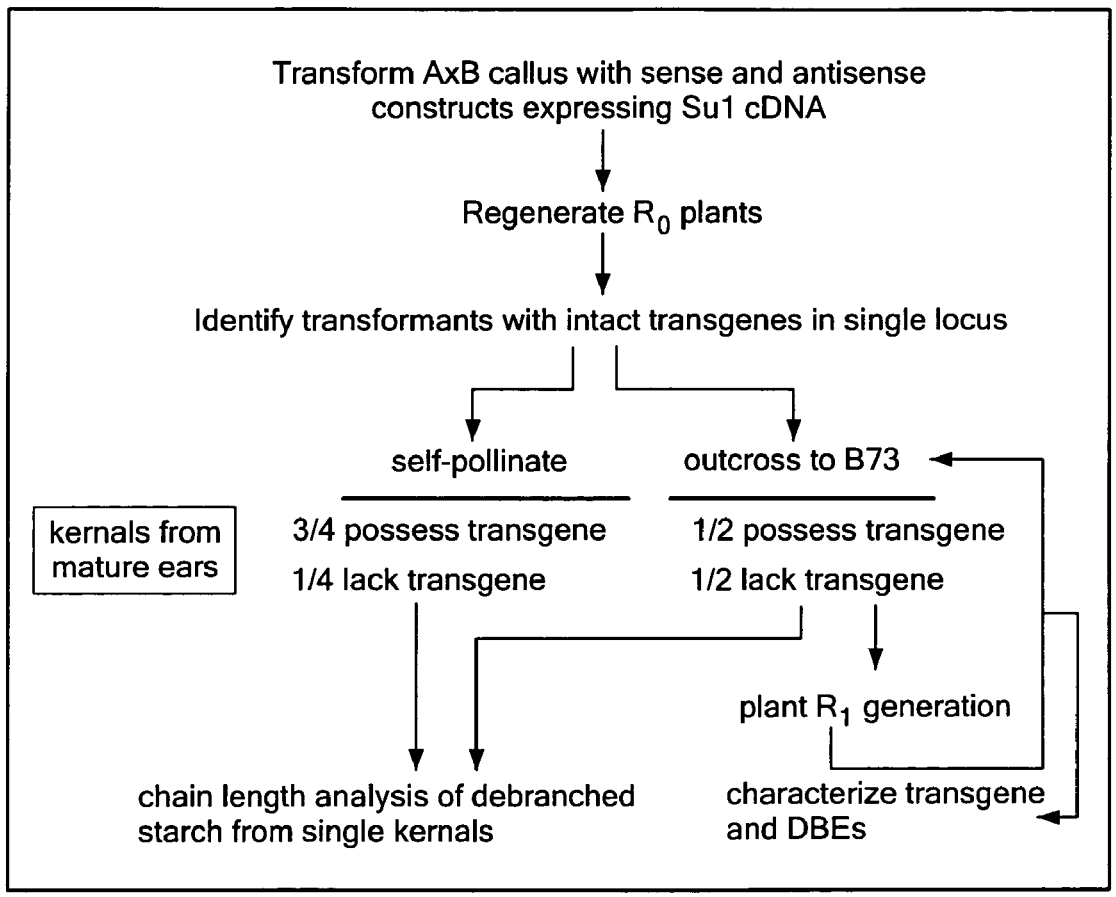
FIG. 25 is a diagram showing an inbreeding scheme to construct transgenic plants according to the invention.

$R_0$ plants were grown in the greenhouse or in the field. These plants were self-pollinated or crossed to B73 plants, or both, depending on ear and pollen development. Some progeny $R_1$ seeds were harvested at 20 days after pollination (DAP) for molecular analysis. The remaining seeds were planted in winter in the greenhouse, or in summer in the field. These $R_1$ plants were self-pollinated or crossed to B73, or both. The crosses to B73 were designed to move all of the plants into a common inbred background. Transgenic plants were characterized at the molecular level by PCR amplification of the transgene, gel blot analysis of genomic DNAs and/or kernel RNAs, and analysis of chain length distributions of the kernel glucans. This scheme is described in FIG. 25.

Transformation of maize with a plasmid construct designed to express SU1 in the sense orientation (pMO5) resulted in 17 independent transformation events, of which six had an intact copy of the transgene. Transformation with constructs that expressed SU1 in the antisense orientation (pMO6 and pMO7, essentially the same, except that pMO6 contains the Adh1 intron and pMO7 does not) resulted in 28 independent transformation events, of which 12 had intact transgene copies (Table IV). Southern hybridization analysis and standard PCR procedures were used to estimate the copy number of intact transgenes present in each line.

TABLE IV

Independent maize transformants with intact transgenes resulting from the introduction of SU1 in the sense or antisense orientation

| | Copy number | Transgene expression | Kernel phenotype | Altered glucans |
|---|---|---|---|---|
| Sense pMO5 | | | | |
| P2P25-14 | 1 | | | |
| P2P25-20 | 31 | | yes | yes |
| P2P25-21 | 7 | yes | | ? |
| P2P25-28 | 13 | | | |
| P2P25-36 | 6 | yes | | |
| P2P25-52 | 10 | yes | | |
| Antisense pMO6 | | | | |
| P2P26-3 | 3 | | yes | yes |
| P2P26-4 | 1 | | yes | yes |
| P2P26-6 | 10 | | | |
| P2P26-10 | 10 | | | yes |

In R1 and R2 plants, the transgene was predicted to segregate 3:1 (transgene: wild type) upon self-pollination, and 1:1 upon out-crossing. These segregation ratios were confirmed by PCR amplification of genomic DNAs for all lines listed in Table 1, and selected examples of this segregation analysis are shown in FIG. 26.

RNA gel blot data demonstrated that the transgenes are expressed at the level of mRNA accumulation in at least some of the sense lines (FIG. 27). The strains shown were bred from lines containing multiple copies of the sense transgene. In several antisense lines, reduced accumulation of endogenous SU1 transcript, presumably as a result of antisense Su1 gene expression, was observed by RNA gel blot analysis using a labeled RNA probe of the sense strand of SU1.

Figure 28:
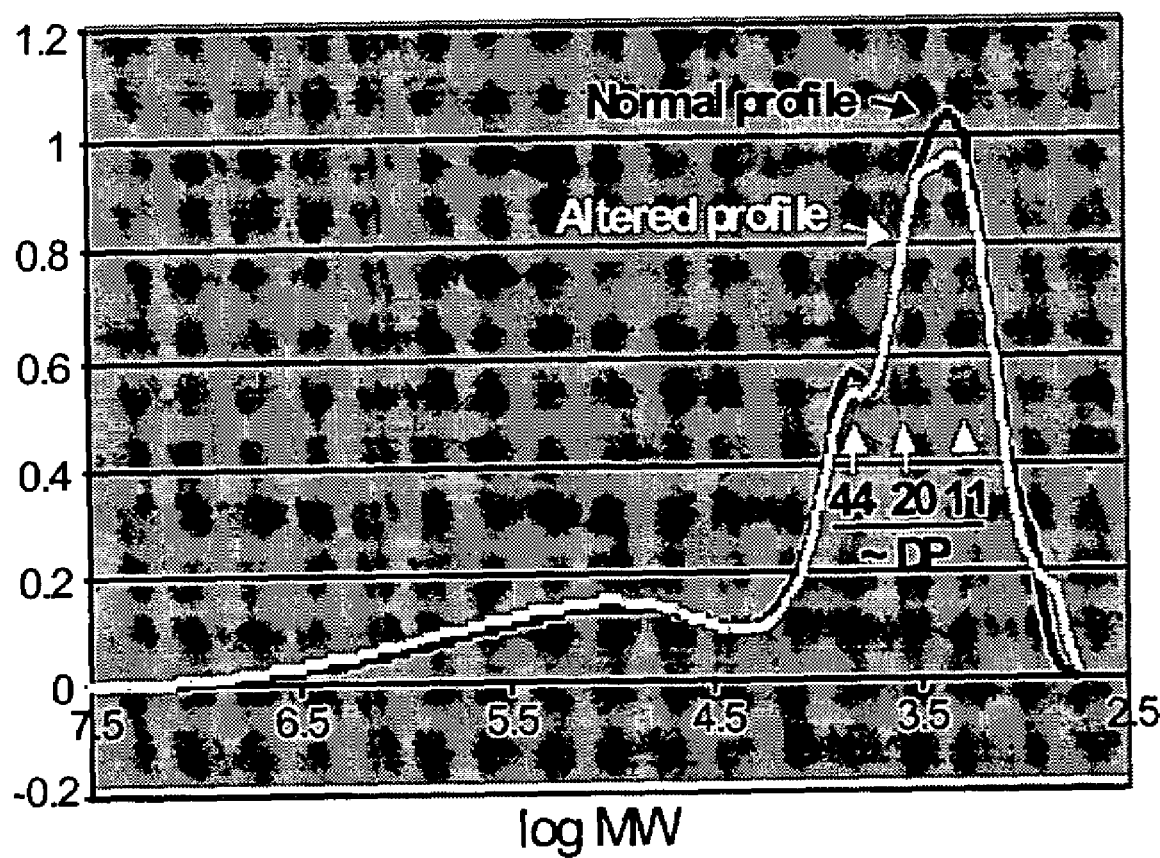
FIG. 28 is a graph showing gel permentation chromotography analysis of debranched whole starch.

Altered carbohydrate structures were observed specifically in certain transgenic lines, and this "chemotype" segregated at the same ratios expected for segregation of the transgene. Thus, the preliminary data are consistent with the proposition that transgenic modification of SU1 activity has effectively resulted in altered starch structures. Analyses of the structures of insoluble glucans produced in mature kernels of $R_1$ transgenic plants were performed by means gel permeation chromatography (GPC), which separated debranched glucan chains according to their molecular mass. A critical feature of the analysis is that glucans are obtained from individual kernels, thus allowing chemotypic classification of individual progeny. Altered amylopectin molecules were observed in segregating populations of kernels on ears that also segregated for the presence of a SU1 transgene (FIG. 28). In 17 instances, self-pollinated ears that segregated 3:1 for a SU1 transgene, and out-cross ears that segregated 1:1, exhibited corresponding segregation ratios for glucan alterations. These represent separate transformation events in two sense lines and 11 antisense lines (Table IV). In both the sense and antisense transformants with the observed chemotype, alterations are observed in the relative abundance of linear chains of approximately 40–45 units, and of the chains 10–20 units in length. The fact that the altered chain length profiles were similar in the sense and antisense lines suggests that alterations in the sense lines were due to a reduction in SU1 expression, most likely as a result of gene silencing.

EXPERIMENTAL PROCEDURES

Maize Stocks, Genetic Crosses, and Allele Nomenclature

Mutations at the sugaryl (SU1) gene locus are generated by crossing active Mutator (Mu) plants (Robertson, 1978) with standard lines as shown in FIG. 5. Standard lines are the F1 hybrids B77/B79 or Q66/Q67. These four inbred lines have no history of Mutator activity. Mutant alleles SU1-R4582::Mu1, SU1-R2412, SU1-R7110 and SU1-R3162 are identified following the self-pollinations of the F1 plants #82–83-4582-43, #87-2412-24, #79-7110-2, and #83-3162-15, respectively. Allele SU1-R8064 is identified following the open pollination of F1 plant #88-8064-1, derived from the cross of a Mutator plant with a plant homozygous for colored aleuronel shrunken1 bronze1 waxy1. These plant numbers are the laboratory designations used to identify each allele; inclusion of the term "Mu1" indicates the particular mutation is known to have resulted from insertion of a Mu1 transposon. Stock number 413B, from the Maize Genetics Cooperation Stock Center, is used for tests of allelism between each of the five new SU1 mutations and the reference allele SU1-Ref.

DNA and RNA Gel Blot Analyses

Standard procedures are used for DNA and RNA gel blot analyses (Ausubel et al., 1989; Sambrook et al., 1989). Maize DNA is isolated from seedling tissue by the method of Dellaporta (1983). Approximately 10 mg of genomic DNA is digested with 30 units of restriction enzyme, separated by electrophoresis in 0.8% agarose gels, and transferred to a nylon membrane (Magnacharge, Micron Separations Inc., Westboro, Mass.). Membranes are hybridized to DNA probes at 65° C. in 6× SSC (1× SSC is 0.15 M NaCl, 0.015 M sodium citrate), 1% sarkosyl, 50 mg/mL denatured salmon sperm DNA (Sigma Chemical Co., St. Louis, Mo.); the probes are radioactively labeled by the random primer method. The membranes then are washed twice in 2×SSC, 0.1% SDS for 30 min at 65° C., twice in 0.2× SSC, 0.1% SDS for 20 min at 65° C., and once in 5 mM Tris-HCl, pH 8.0, for 5 to 10 min at 65° C., and are exposed to x-ray film for 1 to 4 days.

Total RNA is isolated as described (Cone et al., 1986) from maize kernels harvested 20 days after pollination and stored at −80° C. During this procedure water-soluble polysaccharide is removed from the nucleic acid fractions prepared from SU1 mutant kernels by centrifugation at 100,000× g for 1 hr in a Beckman model TL-100 centrifuge. Under these conditions the water-soluble polysaccharide is separated as a gelatinous pellet from the aqueous phase that contains the RNA. Approximately 5 mg total RNA is denatured and separated by electrophoresis in the presence of formaldehyde and then transferred to nylon membranes (Ausubel et al., 1989). Membranes are hybridized at 42° C. to radioactively labeled DNA probes in 50% formamide, 1 M NaCl, 1% SDS, 10% dextran sulfate, 50 mg/mL denatured salmon sperm DNA. After hybridization the membranes are ished as described above for DNA gel blot analysis. Radioactivity remaining on the membranes is detected using the Phosphorimager (Molecular Dynamics).

Genomic and cDNA Cloning Procedures

Approximately 200 mg of genomic DNA isolated and pooled from three SU1-Ref/SU1-R4582::Mu1 seedlings is digested with EcoRI and separated by electrophoresis. DNA is eluted and purified from gel fractions containing fragments approximately 3 to 5 kb in length and ligated to the bacteriophage λ vector NM1149 (Scalenghe et al., 1981). The genomic library is used to infect *Escherichia coli* C600hflA cells (Sambrook et al., 1989), and approximately 200,000 plaques are screened with the Mu1-specific probe MM960. Seven hybridizing clones are single-plaque purified and the genomic 4.0-kb EcoRI fragment present in one recombinant λ clone (H-4) is subcloned into the phagemid vector pBluescript KS+ (Stratagene), producing pMJ60.

A portion of the SU1 cDNA is isolated as follows. A maize endosperm cDNA library in the bacteriophage vector λgt11 is produced using methods known in the art. EcoRI adapters are ligated to cDNA molecules during preparation of this library. Approximately 200,000 plaques from this library are screened with genomic probe BE1000. DNA from eight different hybridizing clones is digested with EcoRI. The largest cDNA insert present is 2.4 kb in length, and comprised two EcoRI fragments of 1.8 and 0.6 kb. These two fragments are subcloned in pBluescript KS+ to produce pMJ67 and pMJ68, respectively.

Size-fractioned genomic libraries comprising EcoRI fragments of approximately 12 kb in lambda DASH EcoRI fragments of approximately 4 kb in lambda ZapExpressII, and BamHI fragments of approximately 10 kb in lambda ZapExpress II (vectors from Stratagene) are analyzed. Three over-lapping clones are identified by screening the genomic libraries with a 755 bp BamHI fragment of the SU1 cDNA, or with 5' or 3' fragments from the transposon-tagged partial genomic clone (James et al., 1995). Genomic sequences are subcloned into plasmids pBluescriptKS+ or pUC119. Nucleotide sequence is obtained by automated dye- terminated cycle sequencing (ABI P*rism*) of both DNA strands from nt 417 to nt 10,596, and of one DNA strand from nt 1 to nt 416, and from nt 10,597 to nt 11,779.

Amplification of 5' cDNA

To obtain the 5' end of the SU1 cDNA, a modification of the rapid amplification of cDNA ends (RACE) protocol (Frohman et al., 1988) is used. Polyadenylated RNA from maize kernels (2 mg) is reverse transcribed using the SU1-specific primer 5'-GTATGTACTATTATCTATCCC-3[1] (10 pmol) (nucleotides 1191-1171) (SEQ ID NO:40). Unincorporated nucleotides and excess primer is removed using Centricon 100 filters (Amicon, Beverly, Mass.). Poly(A)-tailed cDNA is amplified by polymerase chain reaction (PCR) using the SU1-specific primer 5'-GGGATCATAC-CAGCCATTTGA-3' (25 pmol) (nucleotides 713–693) (SEQ ID NO:41), RACE (dT)17 adapter (10 pmol), and RACE amplification primer (25 pmol) (Frohman et al., 1988). The amplified products are digested with BamHI and EcoRI and cloned in phagemid vector pUC119. The resulting plasmid, pMJ125, is characterized by nucleotide sequence analysis and found to extend beyond the 5' terminus of the cDNA clone present in pMJ67.

Nucleic Acid Hybridization Probes

The 960-bp MluI fragment MM960, contained within Mu1, is excised from plasmid pMJ9 (Barker et al., 1984) and used to detect genomic and cloned copies of this transposon. Probe BE1000, a 1.0-kb BamHI-EcoRI fragment comprising part of the Su1 gene locus, is excised from plasmid pMJ60. SU1 cDNA probes are the 755-bp BamHI fragment BB755, the 700-bp BamHI-EcoRI fragment BE700, and the 1780-bp EcoRI fragment EE1780 (all excised from plasmid pMJ67), the 680-bp EcoRI fragment EE680 (excised from plasmid pMJ68), and the 620-bp EcoRI-BamHI fragment EB620 (excised from plasmid pMJ125).

Nucleotide Sequence Analysis

Nucleotide sequence is determined by the chain termination method (Sanger et al., 1977) using Sequenase Version 2.0 (U.S. Biochemical Corp.). To determine the sequence of the maize genomic DNA adjacent to the Mu1 termini in SU1-R4582::Mu1, two EcoRI-NotI fragments from the insert in pMJ60 are subcloned in phagemid vectors. Each of these two fragments contained one of the Mu1 termini. Sequence is determined using oligonucleotide primers from within each terminus and extending in the 3' direction towards the end of the transposon (5'-GGCTGTCGCGT-GCGT-3' (SEQ ID NO: 42), and 5'-GCG-TACGTCTCTAAA-3' (SEQ ID NO:43)). Portions of pMJ60 and all of pMJ67, pMJ68, and pMJ125 are analyzed using various oligonucleotide primers; the original plasmids and various subclones derived from them are used as templates. To sequence across the EcoRI site internal to the cDNA insert in phage λ clone H-4, the 2.9-kb KpnI fragment from this phage is subcloned in pBluescript KS+ to form pMJ99. This fragment extends from the KpnI site in the cDNA to the KpnI site of λgt11. Of the 2712-bp cDNA sequence, approximately 2300 bp are analyzed on both strands, and all restriction sites used for subcloning are crossed.

The GCG sequence analysis software package (Genetics Computer Group, Madison, Wis.) is used for database searches and amino acid sequence alignments. The GenBank accession number for the SU1 cDNA sequence is U18908.

Vector Construction, Protein Expression and Purification

Plasmid pAR4 was constructed to express biochemically active SU1 in *E. coli*. pAR4 contains the near-full length SU1 cDNA (nucleotides 202–2529) as an in-frame fusion with the 3' end of the S-tag sequence (a 15 amino acid peptide derived from RNaseA) in the expression vector pET-29b(+) (Novagen) (FIG. 1C'). pAR4 was constructed by first replacing the 1.3 kb KpnI-XhoI fragment of SU1 cDNA in pAR1 with the longer 1.8 kb KpnI-XhoI cDNA fragment from pMJ99 (James et al., 1995). The resultant plasmid was linearized with XhoI and partially digested with EcoRI to excise a 2327 bp fragment comprising the near-full length SU1 cDNA. This fragment was cloned into pET-29b (+) to create pAR4.

GST-SU1 expression from pAR2 was induced in *E. coli* strain TG-1 by addition of 10 mM IPTG and incubation for 2 h at 30° C. Cells were lysed and separated into soluble and insoluble fractions as described (Koerner et al., 1990). Soluble GST-SU1 fusion protein was purified using glutathione-agarose beads (Sigma) and eluted with 10 mM glutathione according to the manufacturer's protocol (Pharmacia).

The recombinant protein SU1r was expressed from pAR4 in *E. coli* strain BL21(DE3)pLysS (Novagen) and purified as follows. A pure clone was grown overnight at 30° C. in LB medium containing 30 μg/mL kanamycin and 34 μg/mL chloramphenicol, diluted 1:20 with fresh medium, and grown at 30° C. until the A600 reached 0.8–1.2. Cultures were cooled to room temperature, and expression was induced by the addition of 1 mM IPTG and growth at room temperature for 16–20 h. Cells from 100 mL induced culture were harvested by centrifugation, suspended in 10 mL of 20 mM Tris-HCl, pH 7.5, 150 mM NaCl, 5 mM DTT, 0.1% Triton X-100, 1 mM PMSF (Gibco-BRL), and 0.01 mM E64 (Sigma), and lysed by treatment with lysozyme (100 μg/mL) and sonication. Lysates were centrifuged at 39,000 g for 20 min. SU1r was affinity-purified according to the manufacturer's protocol (Novagen) by incubating the total soluble extracts with S-Protein agarose beads, followed by cleavage between the S-tag sequence and SU1r with biotinylated thrombin. Residual biotinylated thrombin was removed from the purified protein by treatment with streptavidin-agarose.

Preparation of Polyclonal Antibodies

Antibodies reactive with SU1 were produced in a New Zealand White rabbit using an animal use protocol approved by the Laboratory Animal Resource Facility, Iowa State University. Purified GST-SU1 fusion protein (300 μg in 1 mL PBS) was emulsified in an equal volume of Freunds complete adjuvant (Gibco-BRL) and administered by injection. Subsequent booster inoculations of 200 μg GST-SU1 emulsified in Freunds incomplete adjuvant were administered three times at three week intervals, and serum was harvested three weeks after the final injection. Pre-immune serum was collected prior to the initial injection to serve as a negative control. Anti-SU1 antibody was purified from the crude antiserum by means of its affinity to SU1r immobilized on nitrocellulose filters (Harlow and Lane, 1988).

Isolation of Proteins from Maize Kernels

Ears were harvested 18–22 days after pollination (DAP) from wild type and SU1-R plants in the W64A or Oh43 background, and from SU1 R4582::Mu1 plants in a mixed genetic background (James et al., 1995). Kernels stripped from the cob were quick-frozen in liquid nitrogen and stored at −80° C. Total protein was extracted from frozen kernels according to Ou-Lee and Setter (1985) with the following modifications: 10 g of maize kernels were homogenized in liquid nitrogen, stirred in extraction buffer (50 mM Hepes-NaOH, pH 7.5, 5 mM $MgCl_2$, 5 mM DTT, 1 mM PMSF, 0.01 mM E64) at 4° C. for 3–4 h, then filtered through four layers of cheese cloth. Soluble extracts were separated from insoluble material in the filtrate by centrifugation at 39,000 g for 20 min at 4° C. Granule-associated proteins and post-granule soluble extracts were isolated from frozen kernels as described by Mu-Forster et al. (1996).

Fractionation of Debranching Enzyme Activities from Maize Endosperms

Kernels were harvested 20 days after pollination (DAP). Endosperm tissues were separated from pericarp and embryos, quickly frozen in liquid nitrogen, and stored at −80° C. Approximately, 25 g of frozen endosperm tissues were pulverized in liquid nitrogen, then stirred overnight at 4° C. in 50 ml extraction buffer (50 mM Hepes-NaOH, pH 7.5, 10 mM EDTA, 5 mM DTT, 1 mM PMSF, 0.5 ml per g tissue protease inhibitor cocktail [Sigma no. 2714]). The suspension was centrifuged at 39,000× g for 20 min. The debris was extracted once more with 10 ml extraction buffer, and centrifuged at 39,000× g for 20 min. The pooled supernatant was filtered through four layers of Miracloth and centrifuged again under the same conditions. The supernatant was then passed through a 0.45 μm syringe filter to yield the crude endosperm extract. This solution was made up to 40% ammonium sulfate and stirred for 1 hr. at 4° C. Precipitated proteins were collected by centrifugation at 16,000× g for 20 min., suspended in 30 ml of buffer A (50 mM Hepes-NaOH, pH 7.5, 10 mM EDTA, 5 mM DTT, 5% glycerol), and dialyzed overnight at 4° C. in 1 liter of the same buffer.

The dialyzed protein solution was centrifuged at 10,000× g for 15 min., and the supernatant was passed through a 0.45 αm syringe filter. The solution was then applied to a pre-equilibrated Q Sepharose Fast Flow column (Pharmacia; 1.5 cm×46 cm column, 80 ml bed volume; approximately 1.3 mg of protein loaded ml$^{-1}$ bed volume). After the column had been washed with 700 ml of buffer A, bound proteins were eluted with a linear 800 ml gradient of 0 to 1M NaCl in buffer A. Fractions (8 ml) were assayed for debranching enzyme activities as described later. Fractions containing debranching enzyme activities were concentrated approximately 80 fold using an Ultrafree-4 centrifugal filter unit concentrator (Millipore, NMW, 10k), pooled, made up to 50% in glycerol, quickly frozen in liquid nitrogen, and stored at −80° C.

Isolation of SU1 from Maize Endosperm

The pooled SU1 fractions from the Q Sepharose column were next applied to a Sephacryl S-200 superfine gel permeation column (Pharmacia; 2.5 cm×90 cm column, 440 ml bed volume and eluted with the equilibration buffer (10 mM Hepes-NaOH, pH 7.5, 5 mM DTT, 5 mM MgCl$_2$) at a flow rate of 0.5 ml min$^{-1}$. Fractions (7.5 ml) with SU1 activities were concentrated as above and then pooled.

The pooled SU1 fractions from the gel filtration column were diluted to 7 ml with buffer A and then loaded onto a pre-equilibrated Mono Q column (Pharmacia, 1 ml resin bed volume, and 5 mg of protein was loaded). The column was washed with 25 ml of buffer A and was eluted with a linear, 80 ml gradient of 0 to 1 M NaCl in buffer A.

The affinity matrix, soluble starch-Sepharose was prepared by conjugating soluble starch from potato (Sigma) to epoxy-activated Sepharose 6B (Sigma), according to the method of Vretblad (1974). For affinity purification of SU1, ~0.5 mg of protein was mixed with ~1 ml of soluble starch-Sepharose (pre-equilibrated with 50 mM MES, pH 6.0, 5 mM DTT) on an aliquot shaker for 2 hrs. at 4° C. After unbound proteins were removed by washing the matrix with the equilibration buffer, SU1 was eluted with 1 mg/ml maltotriose in the same buffer.

SDS-PAGE and Immunoblot Analysis

SDS-PAGE in 10% polyacrylamide gels, silver-staining, and blotting to nitrocellulose membranes were performed according to standard procedures (Sambrook et al., 1989). Immunodetection was modified from the ECL protocol (Amersham Life Sciences) as follows: blots were blocked in 3% BSA (Fraction V, Sigma), 0.02% NaN3 in 1× PBS for 1 h, then incubated overnight at room temperature with affinity-purified anti-SU1 diluted 1:200 in blocking solution, or with a 1:10,000 dilution of the rice anti-R-enzyme antibody (Nakamura et al., 1996a). Secondary antibody was goat anti-rabbit IgG conjugated with horseradish peroxidase (Santa Cruz Biotechnology). For immunoblot analysis of soluble protein extracts approximately 30 μg protein was loaded in each lane. Granule-associated proteins extracted from 5 mg of purified starch granules were loaded in each lane for immunoblot analysis.

Enzyme Assays

DBE activity was measured by increased blue value of glucan-iodine complexes according to Doehlert and Knutson (1991), modified as follows. Reactions incubated at 30° C. included 1 μg purified SU1r and 1 mg polysaccharide substrate in 50 mM citrate, 100 mM sodium phosphate, pH 6, 0.02% NaN$_3$, in a total volume of 1 mL. Immediately after addition of SU1r, and after 1 h incubation, 100 μL aliquots were combined with 900 μL of I$_2$/KI stain. Substrates tested were: maize amylopectin (Sigma); β-limit dextrin of maize amylopectin prepared according to Doehlert and Knutson (1991); oyster glycogen (Sigma); and phytoglycogen prepared according to Sumner and Somers (1944).

Quantitative determination of reducing end formation was performed according to Fox and Robyt (1991). Assay conditions were the same as for blue value assays, except that all substrate concentrations were increased to 5 mg/mL. Pullulan (Sigma) was included as an additional potential substrate. SU1r was present at 0.5 μg/mL for assays of its activity toward amylopectin and β-limit dextrin, and at 1 μg/mL for other substrates. Products were assayed over a time course of 1–6 h; aliquots of 100 μL were removed after each hour, followed by inactivation of the enzyme with 50 μL 1M Na$_2$CO$_3$. Maltose was used as the standard for reducing value.

Enzyme activity as a function of pH was determined from the reducing activity measured after incubating 5 mg amylopectin with 0.5 μg SU1r in 50 mM sodium citrate, 100 mM sodium phosphate buffers varying from pH 3–pH 7; or 100 mM sodium phosphate, pH 8; or in 50 mM glycine-NaOH buffers at pH 9 or pH 10. Formation of reducing ends was assessed hourly over a 6 h time course and specific activities were calculated. In a similar time course, the thermal optimum for SU1r activity towards amylopectin was measured at reaction temperatures varying from 15° C. to 60° C. at pH 6. Thermal stability of SU1r was determined by preincubating the enzyme at temperatures from 30° C. to 60° C. for 10 min, then assessing enzymatic activity at pH 6 at 30° C. Effect of divalent cations on SU1r activity towards amylopectin was determined by adding 10 mM CaCl$_2$ or 10 mM MgCl$_2$ or 10 mM EDTA to the pH 6 reaction buffer, then measuring activity according to the reducing sugar assay.

Analysis of SU1r Reaction Products

The chain lengths of the products formed after incubation of waxy maize amylopectin (Cerestar) with SU1r were analyzed by high-performance anion-exchange chromatography with pulsed amperometric detection (HPAEC-PAD) (Dionex) according to the quantitative methods of Wong and Jane (1995; 1997) with modification of the separation gradient. Eluent A was 100 mM NaOH and eluent B was 100 mM NaOH, 300 mM NaNO3 for the following gradient: 0–5 min, 99% A, 1% B; 5–10 min, linear gradient to 5% B; 10–30 min, linear gradient to 8% B; 30–150 min, linear gradient to 30% B; 150–200 min, linear gradient to 45% B. Debranching reactions included 20 μg SU1r and 5 mg wx amylopectin in 50 mM MES, pH 6, in 1 mL total volume. After incubation at 30° C. for 1 h an aliquot of 25 μL was removed for HPAEC-ENZ-PAD analysis. A similar analysis of wx maize amylopectin debranched by Ps. isoamylase (300 U) (Hayashibara Biochemical Laboratories) was carried out for comparison with SU1r, except that the reaction buffer was 50 mM sodium acetate, pH 3.5, and incubation was for 24 h.

Sequencing of the N-Terminus of SU1

A portion of the pooled SU1 peak fractions from the Mono Q column was separated on a 6% SDS-polyacrylamide preparative gel and blotted onto a PVDF membrane (Bio-Rad) according to the manufacturer's protocol. The blot was stained with Coomassie brilliant blue and destained with 50 percent methanol solution. The band corresponding to SU1 was cut out and subjected to N-terminal sequencing.

Construction of Two-Hybrid Vectors

Plasmids pGAD-C2-SU1 and pGBD-C2-SU1 were constructed to analyze the multimeric structure of SU1, as shown in FIG. 23. These plasmids contain the nearly full-length SU1 cDNA (nucleotides 202–2529) as in-frame fusions with the 3' ends of the activation and binding domains of the transcription factor Gal4, respectively. Plasmids pAR7 and pAR8 were constructed by first cleaving the plasmids pGAD-C2 and pGBD-C2 (James et al., 1996) with SalI, ligating NcoI linkers to the blunt ends produced, and then subcloning the NcoI-SalI fragment from the plasmid pAR4 (Rahman et al., 1998a).

Determination of Relative Molecular Mass of SU1

Molecular mass ($M_r$) of SU1 was determined from a 1×60 cm analytical Sephacryl S-200 HR column equilibrated and eluted with the chromatography buffer (10 mM Hepes NaOH, pH 7, 5 mM $MgCl_2$ and 5 mM DTT). Elution of SU1 was followed by measuring activity in the column fractions using the 12-staining assay. Standard proteins used to calibrate the column were bovine thyroglobulin (670,000), bovine gamma globulin (158,000) chicken ovalbumin (44,000), horse myoglobin (17,000) and vitamin B-12 (1,350) (Bio-Rad).

USE

Corn starch is the primary carbohydrate source for producing fuel ethanol, high fructose corn syrup, and other products. Fungal glucoamylases that are currently used in corn starch processing hydrolyze α-(1,6) glucosidic linkages at approximately ⅕₀th the rate of α-1,4 linkages. The debranching step is the rate limiting step and lengthens the starch refining process up to 75 hours. The use of isolated SU1, appropriately modified for commercial conditions, as a replacement for the bacterial and fungal enzymes currently used in the starch processing industry can significantly increase the efficiency of corn starch processing and thus reduce both time and cost requirements. In addition, the SU1 protein should be capable of acting on starch derivatives that are convertible to biodegradable products.

Use of the SU1 cDNA will make possible the isolation of active portions of SU1 protein and, thus, the development of highly active, chimeric enzyme preparations for corn starch processing. In addition, the availability of SU1 cDNA facilitates direct examination of the putative maize endosperm debranching enzyme SU1 for the ability to hydrolyze a-(1→6) glycosidic linkages. The substrate specificities of bacterial isoamylases and pullulanases have been characterized (Gunja-Smith et al., 1970; Yokobayashi et al., 1970; Lee and Whelan, 1971; Harada et al., 1972; Kainuma et al., 1978), and this information suggests specific biochemical functions of SU1. Isoamylase has strong hydrolytic activity towards both amylopectin and glycogen, and the hydrolysis rate of α-(1→6) linkages in the polysaccharide is about 10-fold greater than in small oligosaccharides. Pullulanase is moderately active in the hydrolysis of amylopectin and is unable to hydrolyze glycogen; its preferred substrate is the ordered glucopolysaccharide pullulan. Neither debranching enzyme releases single glucosyl residues from α-(1→6) linkages. Pullulanase will release maltosyl groups, whereas isoamylase only releases maltotriosyl groups and larger oligosaccharides from branched molecules. Another activity specific to isoamylase is the ability to hydrolyze linkages between α-maltosaccharides and a tyrosine residue of the mammalian protein glycogenin, the putative primer for glycogen biosynthesis (Lomako et al., 1992). If this activity is conserved in SU1, then it is possible that the maize debranching enzyme could affect starch biosynthesis in the endosperm by regulating initiation of polysaccharide chain growth.

Although the invention has been shown and described with respect to illustrative embodiments thereof, it should be appreciated that the foregoing and various other changes, omissions and additions in the form and detail thereof may be made without departing from the spirit and scope of the invention as delineated in the claims.

REFERENCES

Alonso, M. D., Lomako, J., Lomako, W. M., Whelan, W. J. (1995) A new look at the biogenesis of glycogen. FASEB J 9: 1126–1137

Amemura, A., Chakraborty, R., Fujita, M., Noumi, T. and Futai, M. (1988) Cloning and nucleotide sequence of the isoamylase gene from Pseudomonas amyloderamosa SB-15. J. Biol. Chem. 263, 9271–9275.

Ausubel, F. M., Brent, R., Kingston, E. E., Moore, D. D., Seidman, J. G., and Struhl, K. (1989). Current protocols in molecular biology. (New York: John Wiley and Sons).

Baba, T., Nishihara, M., Mizuno, K., Kawasaki, T., Shimada, H., Kobayashi, E., Ohnishi, S., Tanaka, K., and Arai, Y. (1993). Identification, cDNA cloning, and gene expression of soluble starch synthase in rice (Oryza sativa L.) immature seeds. Plant Physiol 103: 565–573.

Ball, S., Guan H—P, James, M., Myers, A., Keeling, P., Mouille, G., Buleon, A., Colonna, P., Preiss, J. (1996) From glycogen to amylopectin: A model for the biogenesis of the plant starch granule. Cell 86: 349–352

Banks, W., Greenwood Conn., Khan KM (1971) The interaction of linear, amylose oligomers with iodine. Carbohydrate Res 17: 25–33

Barker, R. F., Thompson, D. V., Talbot, D. R., Swanson, J., and Bennetzen, J. L. (1984) Nucleotide sequence of the maize transposable element Mu1. Nucleic Acids Research 12, 5955–5967.

Beatty, M., Myers, A. M., James, M. G. (1997) Genomic nucleotide sequence of a full-length wild type allele of the maize sugaryl (SU1) gene (Accession No. AF030882). Plant Physiol in press.

Black, R. C., Loerch, J. D., McArdle, F. J., and Creech, R. G. (1966) Genetic interactions affecting maize phytoglycogen and the phytoglycogen-forming branching enzyme. Genetics 53, 661–668.

Cone, K. C., Burr, F. A., and Burr, B. (1986) Molecular analysis of the maize anthocyanin regulatory locus C1. Proc. Natl. Acad. Sci. USA 83, 9631–9635.

Correns, C. (1901) Bastarde zwischen maisrassen, mit besonder Berucksichtung der Xenien. Bibliotheca Bot 53: 1–161

Dellaporta, S. L., Wood, J., and Hicks, J. B. (1983) A plant version of DNA minipreparation: Version II. Plant Mol. Biol. Rep. 1, 19–21.

Doehlert, D. C., Knutson, C. A. (1991) Two classes of starch debranching enzymes from developing maize kernels. J Plant Physiol 138: 566–572

Erlander, S. (1958) Proposed mechanism for the synthesis of starch by glycogen. Enzymologia 19, 273–283.

Evensen, K. B., and Boyer, C. D. (1986) Carbohydrate composition and sensory quality of fresh and stored sweet corn. J. Amer. Soc. Hort. Sci. 111, 734–738.

Fox, J. D., Robyt, J. F. (1991) Miniaturization of three carbohydrate analyses using a microsample plate reader. Analytical Biochemistry 195: 93–96

French, D. (1984) Organization of the starch granule. In R. L. Whistler, J. M. BeMiller, E. F. Paschall, eds, Starch: Chemistry and technology, Academic Press, Orlando, pp 183–248

Frohman, M., Dush, M., and Marlin, G. (1988) Rapid amplification of full-length cDNAs from rare transcripts:

Amplification using a single gene-specific oligonucleotide primer. Proceedings of the National Academy of Sciences 85, 8998–9002.

Gallie, D. R. (1993) Posttranscriptional regulation of gene expression in plants. Annu Rev Plant Physiol Plant Mol Biol 44: 77–105.

Garwood, D. L., and Creech, R. G. (1972). Kernel phenotype of Zea mays L. genotypes possessing one to four mutated gene. Agron Abstr 7: 119–121.

Gunja-Smith, Z., Marshall, J. J., Smith, E. E. and Whelan, W. J. (1970) A glycogen debranching enzyme from Cytophaga. FEBS Lett. 12, 96–100.

Gunja-Smith, Z., Marshall, J. J., Mercier, C., Smith, E. E., Whelan, W. J. (1970) A revision of the Meyer-Bernfeld model of glycogen and amylopectin. FEBS Lett 12: 101–104

Hannah, L. C., Giroux, M., Boyer, C. (1993) Biotechnological modification of carbohydrates for sweet corn and maize improvement. Scientia Horticulturae 55: 177–197

Harada, T., Misaki, A., Akai, H., Yokobayashi, K. and Sugimoto, K. (1972) Characterization of Pseudomonas isoamylase by its actions on amylopectin and glycogen: Comparison with Aerobacter pullulanase. BBA 268, 497–505.

Harlow, E., Lane, D. (1988) Antibodies: A laboratory manual. Cold Spring Harbor Laboratory, Ishizaki, Y., Taniguchi, H., Maruyama, Y., and Nakamura, M. (1983). Debranching enzymes of potato tubers (Solanum tuberosum L.) I. Purification and some properties of potatoe isoamylase. J Biol Chem 47: 771–779.

James, M. G., Robertson, D. S., Myers, A. M. (1995) Characterization of the maize gene sugaryl, a determinant of starch composition in kernels. Plant Cell 7: 417–429

James, P., Halladay, J., and Craig, E. A. (1996). Genomic libraries and a host strain designed for highly efficient two-hybrid selection in yeast. Genetics 144: 1425–1436.

Jenkins, P. J., Cameron, R. E., Donald, A. M. (1993) A universal feature in the starch granules from different botanical sources. Starke 45: 417–420

Jesperson, H. M., MacGregor, E. A., Henrissat, B., Sierks, M. R. and Svensson, B. (1993) Starch- and glycogen-debranching and branching enzymes: Prediction of structural features of the catalytic (b/a)8-barrel domain and evolutionary relationship to other amylolytic enzymes. J. Protein Chem. 12, 791–805.

Joshi, C. P. (1987) An inspection of the domain between putative TATA box and translation start site in 79 plant genes. Nucleic Acids Res 15: 6643–6653.

Kainuma, K., Kobayashi, S. and Harada, T. (1978) Action of Pseudomonas isoamylase on various branched oligo- and polysaccharide. Carbohydrate Research 61, 345–357.

Knight, M. E., Harn, C., Lilley, C. E. R., Guan, H., Singletary, G. W., Mu-Forster, C., Wasserman, B. P., and Keeling, P. L. (1998). Molecular cloning of starch synthase I from maize (W64) endosperm and expression in Escherichia coli. The Plant J 14: 613–622.

Koerner, T. J., Hill, J. E., Myers, A. M., Tzagoloff, A. (1990) High-expression vectors with multiple cloning sites for construction of trpE-fusion genes: pATH vectors. Methods Enzymol 194: 477–490

Kohler, G. (1986) Derivation and diversification of monoclonal antibodies. Science 233, 1281–6.

Lee, E. Y. C., Whelan, W. J. (1971) Glycogen and starch debranching enzymes. In P Boyer, eds, The Enzymes, 3. Academic Press, New York, pp 191–234

Lomako, J., Lomako, W. M. and Whelan, W. J. (1992) The substrate specificity of isoamylase and the preparation of apo-glycogenin. Carbohydrate Research 227, 331–338.

Ludwig, S. R., Bowen, B., Beach, L. and Wessler, S. R. (1990) A regulatory gene as a novel visible marker for maize transformation. Science 247, 449–450.

MacGregor, E. A. and Svensson, B. (1989) Super-secondary structure predicted to be common to several a-1,4-D-glucan-cleaving enzymes. Biochem. J. 259, 145–152.

Manners, D. J. (1985) Starch. In Biochemistry of storage carbohydrated in green plants, (P. M. Dey, Dixon, R. A.). London; Academic Press, 149–204.

Manners, D. J. (1971) Nature New Biol 234: 150 Academic Press, 191–234.

Manners, D. J. (1989) Recent developments in our understanding of amylopectin structure. Carbohyd Polymers 11: 87–112

Manners, D. J., Rowe, K. L. (1969) Studies on carbohydrate-metabolizing enzymes. XX. Sweet corn debranching enzyme. Carbohydr Res 9: 107–121

Martin, C., Smith, A. M. (1995) Starch biosynthesis. Plant Cell 7: 971–985

Matsuura, E. T., Chigusa, S. I. and Niki, Y. (1989) Induction of mitochondrial DNA heteroplasmy by intra- and interspecific transplantation of germ plasm in Drosophila. Genetics 122, 663–667.

Matsuura, Y., Kusunoki, M., Harada, W. and Kakudo, M. (1984) Structure and possible catalytic residues of Taka-amylase A. J. Biochem. 95, 697–702.

Milstein, C. (1980) Monoclonal antibodies. Sci Am 243, 66–74. Milstein, C. (1986) From antibody structure to immunological diversification of immune response. Science 231, 1261–8.

Mouille, G., Colleoni, C., Maddelein, M., Libessart, N., Decq, A., Delrue, B., Ball, S., (1996a) Glucan trimming: A novel mechanism that explains the asymmetric distribution of a-1,6 branches in amylopectin. Y Nakamura, ed, 5th NIAR/COE International Symposium, Tsukuba, Japan, National Institute of Agrobiological Resources, pp 27–32

Mouille, G., Maddelein, M. L., Libessart, N., Talaga, P., Decq, A., Delrue, B., Ball, S. (1996b) Preamylopectin processing: A mandatory step for starch biosynthesis in plants. Plant Cell 8: 1353–1366

Mu-Forster, C., Huang, R., Powers, J. R., Harriman, R. W., Knight, M., Singletary, G. W., Keeling, P. L., Wasserman, B. P. (1996) Physical association of starch biosynthetic enzymes with starch granules of maize endosperm. Plant Physiol 111: 821–829

Nakajima, R., Imanaka, T. and Aiba, S. (1986) Comparison of amino acid sequences of eleven different a-amylases. J. Bacteriol. 173, 6147–6152.

Nakajima-Shimada, J., Iida, H., Tsuji, F. I. and Anraku, Y. (1991) Monitoring of intracellular calcium in Saccharomyces cerevisiae with an apoaequorin cDNA expression system. Proceedings of the National Academy of Sciences 88, 6878–6882.

Nakamura, Y., Umemoto, T., Ogata, N., Kuboki, Y., Yano, M., Sasaki, T. (1996a) Starch debranching enzyme (R-enzyme or pullulanase) from developing rice endosperm: purification, cDNA and chromosomal location of the gene. Planta 199: 209–218

Nakamura, Y., Umemoto, T., Takahata, Y., Komae, K., Amano, E., Satoh, H. (1996b) Changes in structure of starch and enzyme activities affected by sugary mutations in developing rice endosperm: possible role of starch debranching enzyme (R-enzyme) in amylopectin biosynthesis. Physiol Plant 97: 491–498

Nelson, O., Pan, D. (1995) Starch synthesis in maize endosperms. Annu Rev Plant Physiol Plant Mol Bio 46: 475–496

Ou-Lee, T., Setter, T. L. (1985) Effect of increased temperature in apical regions of maize ears on starch-synthesis enzymes and accumulation of sugars and starch. Plant Physiol 79: 852–855

Pan, D. and Nelson, O. E. (1984) A debranching enzyme deficiency in endosperms of the sugary-1 mutants of maize. Plant Physiol. 74, 324–328.

Preiss, J. (1991) Biology and molecular biology of starch synthesis and its regulation. Oxford surveys of plant molecular and cell biology 7: 59–114

Preiss, J., Sivak, M. N. (1996) Starch synthesis in sinks and sources. In E Samski, Schaffer, A. A., eds, Photoassimilate distribution in plants and crops, Marcell Dekker, Inc., New York, pp 63–96

Rahman, A., Wong K-S, Jane J-L, Myers, A. M., and James, M. G. (1998a). Characterization of SU1 isoamylase, a determinant of storage starch structure in maize. Plant Physiol. 117: 425–435.

Rahman, A., Beatty, M. K., Cao, H., Woodman, W., Lee, M., Myers, A. M., and James, M. G. (1998b). Genetic and biochemical characterization of ZPU1, a pullulanase-type starch debranching enzyme from maize. Plant Physiol (submitted).

Rohman, S., Kosar-Hashemi, B., Samuel, M. S., Hill, A., Abbot, D. C., Preiss, J., Appels, R., and Morell, M. K. (1995). The major proteins of wheat starch granules. Aust J Plant Physiol 22: 793–803.

Robertson, D. S. (1978) Characterization of a mutator system in maize. Mutat. Res. 51, 21–28.

Romeo, T., Kumar, A. and Preiss, J. (1988) Analysis of the *Escherichia coli* glycogen gene cluster suggests that catabolic enzymes are encoded among the biosynthetic genes. Gene 70, 363–376.

Sambrook, J., Fritsch, E. F., Maniatis, T. (1989) Molecular cloning. A laboratory manual. Cold Spring Harbor Laboratory, Cold Spring Harbor, N.Y.

Sanger, F., Nicklen, S. and Coulson, A. R. (1977) DNA sequencing with chain-terminating inhibitors. Proceedings of the National Academy of Sciences 74, 5463–5467.

Scanlon, M. J., Stinard, P. S., James, M. G., Myers, A. M. and Robertson, D. S. (1994) Genetic analysis of sixty three mutations affecting maize kernel development isolated from Robertson' mutator stocks. Genetics submitted, 1993.

Schulze-Lefert, P., Dangl, J. L., Becker-Andre, M., Hahlbrock, K., Schulz, W. (1989) Inducible in vivo DNA footprints define sequences necessary for UV light activation of the parsley chalcone synthase gene. EMBO J. 8: 651–656.

Singer, M., Berg, P. (1991) Genes and Genomes. University Science Books, Mill Valley, Calif.

Smith, A. M., Denyer, K., Martin, C. (1996) The synthesis of the starch granule. Annu Rev Plant Physiol 48: 67–87

Sumner, J. B. and Somers, G. F. (1944) The water soluble polysaccharide of sweet corn. Arch. Biochem. 4, 4–7.

Svensson, B. (1988) Regional distant sequence homology between amylases, a-glucosidases and transglucanosylases. FEBS Letters 230, 72–76.

Toguri, T. (1991) Changes of a rice debranching enzyme during seed formation and germination. J Plant Physiol 137: 541–546

Vanderslice, S. F., and Garwood, D. (1978). Carbohydrate composition of alleles at the sugary locus in *Zea mays*. Agron. Abstr. 66: 1978.

van der Steege, G., Swaving, J., Tempelaar, M. J. (1992) Potato granule-bound starch synthase promoter-controlled GUS expression: Regulation of expression after transient and stable transformation. Plant Mol Biol 20: 19–30.

Vretblad, P. (1974). Immobilization of ligands for biospecific affinity chromatography via their hydroxyl groups. The cyclohexa-amylose-b-amylose system. FEBS Lett 47: 86–89.

Wong, K-S, Jane, J. (1995) Effects of pushing agents on the separation and detection of branched amylopectin by high performance anion exchange chromatography with pulsed amperometric detection. Journal of Liquid Chromatography 18: 63

Wong, K-S., Jane, J-L (1997) Quantitative analysis of debranched amylopectin by HPAEC-PAD with postcolumn enzyme reactor. J Liquid Chromotography 20: 297–310

Yokobayashi, I., Akai, H., Sugimoto, T., Hirao, K., Sugimoto, K., Harada, T. (1973) Comparison of the kinetic parameters of *Pseudomonas* isoamylase and Aerobacter pullulanase. Biochim Biophys Acta 293: 197–202

Yokobayashi, K., Misaka, A. and Harada, T. (1970) Purification and properties of *Pseudomonas* isoamylase. BBA 212, 458–469.

Yu, Y., Mu, H,H., Mu-Foster, C., and Wasserman, B. P. (1998). Polypepteides of the maize amyloplast stroma. Plant Physiol 116: 1451–1460.

Yun, S., Matheson, N. K. (1993) Structures of the amylopectins of waxy, normal, amylose-extender, and wx:ae genotypes and of the phytoglycogen of maize. Carbohyd Res 243: 307–321

What is claimed is:

1. A transgenic plant comprising a genome including a foreign DNA sequence that hybridizes under stringent conditions to the complement of a sequence encoding the SU1 protein having the amino acid sequence shown in FIG. 1 (SEQ ID NO:2).

2. A transgenic plant comprising a genome including a foreign DNA sequence comprising a nucleotide sequence selected from the group consisting of nucleotide 1884 to nucleotide 2333, nucleotide 2578 to nucleotide 2763, nucleotide 2887 to nucleotide 2980, nucleotide 3315 to nucleotide 3467, nucleotide 3924 to nucleotide 4000, nucleotide 4248 to nucleotide 4389, nucleotide 4481 to nucleotide 4588, nucleotide 4707 to nucleotide 4792, nucleotide 5063 to nucleotide 5333, nucleotide 7042 to nucleotide 7128, nucleotide 7903 to 8895, nucleotide 9317 to nucleotide 9397, nucleotide 9490 to nucleotide 9572, nucleotide 9700 to nucleotide 9817, and nucleotide 9938 to nucleotide 10438 of SEQ ID NO:3.

3. A nucleic acid isolate that hybridizes under stringent conditions to a sequence encoding the SU1 protein having the amino acid sequence shown in FIG. 1 (SEQ ID NO:2).

4. A nucleic acid isolate comprising the complement of a nucleotide sequence selected from the group consisting of nucleotide 1884 to nucleotide 2333, nucleotide 2578 to nucleotide 2763, nucleotide 2887 to nucleotide 2980, nucleotide 3315 to nucleotide 3467, nucleotide 3924 to nucleotide 4000, nucleotide 4248 to nucleotide 4389, nucleotide 4481 to nucleotide 4588, nucleotide 4707 to nucleotide 4792, nucleotide 5063 to nucleotide 5333, nucleotide 7042 to nucleotide 7128, nucleotide 7903 to 8895, nucleotide 9317 to nucleotide 9397, nucleotide 9490 to nucleotide 9572, nucleotide 9700 to nucleotide 9817, and nucleotide 9938 to nucleotide 10438 of SEQ ID NO:3.

5. A recombinant expression vector comprising the nucleic acid isolate of claim 3.

6. A composition comprising a cell transformed with the recombinant expression vector of claim 5.

7. A recombinant expression vector comprising the nucleic acid isolate of claim 4.

8. A composition comprising a cell transformed with the recombinant expression vector of claim 7.

9. A nucleic acid isolate comprising a nucleotide sequence selected from the group consisting of nucleotide 1884 to nucleotide 2333, nucleotide 2578 to nucleotide 2763, nucleotide 2887 to nucleotide 2980, nucleotide 3315 to nucleotide 3467, nucleotide 3924 to nucleotide 4000, nucleotide 4248 to nucleotide 4389, nucleotide 4481 to nucleotide 4588, nucleotide 4707 to nucleotide 4792, nucleotide 5063 to nucleotide 5333, nucleotide 7042 to nucleotide 7128, nucleotide 7903 to 8895, nucleotide 9317 to nucleotide 9397, nucleotide 9490 to nucleotide 9572, nucleotide 9700 to nucleotide 9817, and nucleotide 9938 to nucleotide 10438 of SEQ ID NO:3.

10. A recombinant expression vector comprising the nucleic acid isolate of claim 9.

11. A composition comprising a cell transformed with the recombinant expression vector of claim 10.

* * * * *

UNITED STATES PATENT AND TRADEMARK OFFICE
CERTIFICATE OF CORRECTION

PATENT NO. : 6,995,300 B2
DATED : February 7, 2006
INVENTOR(S) : Alan M. Myers et al.

It is certified that error appears in the above-identified patent and that said Letters Patent is hereby corrected as shown below:

Column 1,
Lines 19-20, "Grant No. 95-34340-1605." should read -- Grant Nos. 93-37301-8671 and 2001-35318-10003. --;

Column 11,
Line 5, "that in" should read -- that is in --;

Column 15,
Line 9, "(16)" should read -- (1→6) --;

Column 19,
Line 22, "form" should read -- from --;

Column 21,
Line 9, "GLA4-dependent" should read -- GAL4-dependent --;

Column 23,
Line 58, "ished" should read -- processed --;

Column 24,
Line 40, "5'GTATGTACTATTATCTATCCC-3[1]" should read -- 5'GTATGTACTATTATCTATCCC-3' --.

Column 26,
Line 66, "αm" should read -- μm --; and

UNITED STATES PATENT AND TRADEMARK OFFICE
CERTIFICATE OF CORRECTION

PATENT NO. : 6,995,300 B2
DATED : February 7, 2006
INVENTOR(S) : Alan M. Myers et al.

It is certified that error appears in the above-identified patent and that said Letters Patent is hereby corrected as shown below:

Column 29,
Line 13, "12-staining" should read -- $I_2$-staining --.

Signed and Sealed this

Eighteenth Day of April, 2006

JON W. DUDAS
*Director of the United States Patent and Trademark Office*

SEQUENCE LISTING

<160> NUMBER OF SEQ ID NOS: 43

<210> SEQ ID NO 1
<211> LENGTH: 2715
<212> TYPE: DNA
<213> ORGANISM: Zea mays
<220> FEATURE:
<221> NAME/KEY: CDS
<222> LOCATION: (88)...(2454)

-continued

<400> SEQUENCE: 1

```
cgtctcgtca cacactccac tcgaacgcac tacttgatcg gccaaagcca aacgaactgg      60
gctccctccc ctccacttcc tctcccc atg gcg cag agc agc tcc cct gcg tct     114
                               Met Ala Gln Ser Ser Ser Pro Ala Ser
                                 1               5 cgt cgc cgc gcc cgc tgc tcg ccg tgc ccg cgg gcc ggt ggc gcg ccg       162
Arg Arg Arg Ala Arg Cys Ser Pro Cys Pro Arg Ala Gly Gly Ala Pro
 10              15                  20                  25 gcg tgc ggg gcc ggc cca atg tgg cgg gac tgg ggc ggg ggt tgt           210
Ala Cys Gly Ala Gly Pro Met Trp Arg Asp Trp Gly Gly Gly Cys
             30                  35                  40 ctc tcc acg ccg ccg ccg cgc ggc ccg tgg ccg agg cgg tgc agg cgg       258
Leu Ser Thr Pro Pro Pro Arg Gly Pro Trp Pro Arg Arg Cys Arg Arg
             45                  50                  55 agg agg acg acg acg acg acg agg agg tgg ccg agg gag agg ttc           306
Arg Arg Thr Thr Thr Thr Thr Arg Arg Trp Pro Arg Glu Arg Phe
             60                  65                  70 gcg ctg ggc ggc gcg tgc cgg gtg ctc gcg gga atg ccc gcg ccg ctc       354
Ala Leu Gly Gly Ala Cys Arg Val Leu Ala Gly Met Pro Ala Pro Leu
 75                  80                  85 ggc gcc acc gcg ctc cgc ggc ggt gtc aac ttc gcc gtc tac tcc agc       402
Gly Ala Thr Ala Leu Arg Gly Gly Val Asn Phe Ala Val Tyr Ser Ser
 90                  95                 100                 105 ggt gcc tcc gcc gcg tcg ctg agc ctc ttc gct ccc ggc gac ctc aag       450
Gly Ala Ser Ala Ala Ser Leu Ser Leu Phe Ala Pro Gly Asp Leu Lys
                110                 115                 120 gcg gat agg gtg acc gag gag gtg ccc ctc gat ccc ctg ctc aac cga       498
Ala Asp Arg Val Thr Glu Glu Val Pro Leu Asp Pro Leu Leu Asn Arg
                125                 130                 135 acg gga aac gtg tgg cac gtg ttc atc cac ggg gac gag ctg cac ggc       546
Thr Gly Asn Val Trp His Val Phe Ile His Gly Asp Glu Leu His Gly
                140                 145                 150 atg ctc tgc gga tac agg ttc gat ggc gtg ttc gcc cct gag cgc gga       594
Met Leu Cys Gly Tyr Arg Phe Asp Gly Val Phe Ala Pro Glu Arg Gly
 155                 160                 165 cag tac tac gat gtg tcc aac gtt gtg gtg gat cca tac gct aag gca       642
Gln Tyr Tyr Asp Val Ser Asn Val Val Val Asp Pro Tyr Ala Lys Ala
170                 175                 180                 185 gtg gta agc cga ggt gaa tat ggt gtg cct gcg cct ggt ggt agt tgt       690
Val Val Ser Arg Gly Glu Tyr Gly Val Pro Ala Pro Gly Gly Ser Cys
                190                 195                 200 tgg cct caa atg gct ggt atg atc cct ctt ccc tat aat aag ttt gat       738
Trp Pro Gln Met Ala Gly Met Ile Pro Leu Pro Tyr Asn Lys Phe Asp
                205                 210                 215 tgg caa ggt gac cta ccc ctt ggg tac cat cag aag gac ctt gtc ata       786
Trp Gln Gly Asp Leu Pro Leu Gly Tyr His Gln Lys Asp Leu Val Ile
                220                 225                 230 tat gaa atg cat ttg cgt gga ttc aca aag cac aac tca agc aag aca       834
Tyr Glu Met His Leu Arg Gly Phe Thr Lys His Asn Ser Ser Lys Thr
 235                 240                 245 aaa cac cca gga act tac att ggt gct gtg tca aag ctt gac cat cta       882
Lys His Pro Gly Thr Tyr Ile Gly Ala Val Ser Lys Leu Asp His Leu
250                 255                 260                 265 aag gaa ctt gga gtg aac tgt ata gag cta atg ccc tgc cat gag ttc       930
Lys Glu Leu Gly Val Asn Cys Ile Glu Leu Met Pro Cys His Glu Phe
                270                 275                 280 aat gag cta gag tac ttc agc tcc tct tcg aag atg aac ttc tgg gga       978
Asn Glu Leu Glu Tyr Phe Ser Ser Ser Ser Lys Met Asn Phe Trp Gly
                285                 290                 295
```

```
                                                        -continued
tat tcc aca ata aat ttt ttc tca cca atg gca aga tat tct tca agt       1026
Tyr Ser Thr Ile Asn Phe Phe Ser Pro Met Ala Arg Tyr Ser Ser Ser
        300                 305                 310 ggc ata aga gac tct gga tgt ggt gcc ata aat gaa ttt aaa gct ttt       1074
Gly Ile Arg Asp Ser Gly Cys Gly Ala Ile Asn Glu Phe Lys Ala Phe
315                 320                 325 gta agg gag gcc cac aaa cgg gga att gag gtg atc atg gat gtt gtc       1122
Val Arg Glu Ala His Lys Arg Gly Ile Glu Val Ile Met Asp Val Val
330                 335                 340                 345 ttc aat cat aca gct gaa ggt aat gag aaa ggc cca ata tta tcc ttt       1170
Phe Asn His Thr Ala Glu Gly Asn Glu Lys Gly Pro Ile Leu Ser Phe
                350                 355                 360 agg ggg ata gat aat agt aca tac tac atg ctt gca cct aag gga gag       1218
Arg Gly Ile Asp Asn Ser Thr Tyr Tyr Met Leu Ala Pro Lys Gly Glu
            365                 370                 375 ttt tat aat tat tct ggt tgt gga aat acc ttc aat tgt aat cat cct       1266
Phe Tyr Asn Tyr Ser Gly Cys Gly Asn Thr Phe Asn Cys Asn His Pro
        380                 385                 390 gta gtc cgt gaa ttt ata gtg gat tgc ttg aga tac tgg gta aca gaa       1314
Val Val Arg Glu Phe Ile Val Asp Cys Leu Arg Tyr Trp Val Thr Glu
395                 400                 405 atg cat gtt gat ggt ttt cgt ttt gac ctt gca tct ata ctg acc aga       1362
Met His Val Asp Gly Phe Arg Phe Asp Leu Ala Ser Ile Leu Thr Arg
410                 415                 420                 425 gga tgc agt cta tgg gat cca gtt aat gtg tat gga agt cca atg gaa       1410
Gly Cys Ser Leu Trp Asp Pro Val Asn Val Tyr Gly Ser Pro Met Glu
                430                 435                 440 ggt gac atg att acg aca ggg aca cct ctt gtt gcc cca cca ctt att       1458
Gly Asp Met Ile Thr Thr Gly Thr Pro Leu Val Ala Pro Pro Leu Ile
            445                 450                 455 gac atg att agc aat gac cca att ctt gga aat gtc aag ctc att gct       1506
Asp Met Ile Ser Asn Asp Pro Ile Leu Gly Asn Val Lys Leu Ile Ala
        460                 465                 470 gaa gca tgg gat gca gga ggt ctc tat caa gaa ggt cag ttt cct cac       1554
Glu Ala Trp Asp Ala Gly Gly Leu Tyr Gln Glu Gly Gln Phe Pro His
475                 480                 485 tgg aac gtt tgg tca gag tgg aat gga aag tat cgc gat acc gtg cgt       1602
Trp Asn Val Trp Ser Glu Trp Asn Gly Lys Tyr Arg Asp Thr Val Arg
490                 495                 500                 505 cag ttc atc aaa ggc aca gat gga ttt gct ggt gct ttt gct gaa tgc       1650
Gln Phe Ile Lys Gly Thr Asp Gly Phe Ala Gly Ala Phe Ala Glu Cys
                510                 515                 520 cta tgt gga agt cca cag tta tac cag gca ggg ggg agg aag cct tgg       1698
Leu Cys Gly Ser Pro Gln Leu Tyr Gln Ala Gly Gly Arg Lys Pro Trp
            525                 530                 535 cac agt atc ggc ttt gta tgt gca cac gat gga ttt aca ctg gct gat       1746
His Ser Ile Gly Phe Val Cys Ala His Asp Gly Phe Thr Leu Ala Asp
        540                 545                 550 ttg gtc aca tac aat agc aag tac aac ttg tca aat ggt gag gac ttc       1794
Leu Val Thr Tyr Asn Ser Lys Tyr Asn Leu Ser Asn Gly Glu Asp Phe
555                 560                 565 aga gat ggg gaa aat cat aat ctt agc tgg aat tgt ggg gag gaa gga       1842
Arg Asp Gly Glu Asn His Asn Leu Ser Trp Asn Cys Gly Glu Glu Gly
570                 575                 580                 585 gaa ttt gca agt ctg tca gtc cga aga tta agg aag agg caa atg cgc       1890
Glu Phe Ala Ser Leu Ser Val Arg Arg Leu Arg Lys Arg Gln Met Arg
                590                 595                 600 aat ttc ttt gtt tgt ctt atg gtt tct cag gga gtt cca atg ttc tac       1938
Asn Phe Phe Val Cys Leu Met Val Ser Gln Gly Val Pro Met Phe Tyr
            605                 610                 615
```

```
atg ggc gat gaa tat ggt cac aca aag gga ggg aac aac aat acg tac       1986
Met Gly Asp Glu Tyr Gly His Thr Lys Gly Gly Asn Asn Asn Thr Tyr
    620                 625                 630 tgc cat gac cat tat gtc aat tat ttc cgt tgg gat aag aag gaa gaa       2034
Cys His Asp His Tyr Val Asn Tyr Phe Arg Trp Asp Lys Lys Glu Glu
635                 640                 645 caa tcc tct gat ttg tac aga ttc tgc cgt ctc atg acc gaa ttc cgc       2082
Gln Ser Ser Asp Leu Tyr Arg Phe Cys Arg Leu Met Thr Glu Phe Arg
650                 655                 660                 665 aaa gaa tgt gaa tct ctt ggc ctt gag gac ttc ccg act tca gaa cgg       2130
Lys Glu Cys Glu Ser Leu Gly Leu Glu Asp Phe Pro Thr Ser Glu Arg
                670                 675                 680 ttg aaa tgg cac ggt cat cag ccc ggg aag cct gac tgg tca gag gca       2178
Leu Lys Trp His Gly His Gln Pro Gly Lys Pro Asp Trp Ser Glu Ala
            685                 690                 695 agc cga ttc gtt gcc ttc acc atg aag gac gaa acc aaa ggc gag atc       2226
Ser Arg Phe Val Ala Phe Thr Met Lys Asp Glu Thr Lys Gly Glu Ile
        700                 705                 710 tac gtg gcc ttc aac acc agt cac ctt ccg gtg gtt gtt ggg ctt cca       2274
Tyr Val Ala Phe Asn Thr Ser His Leu Pro Val Val Val Gly Leu Pro
    715                 720                 725 gag cgc tct ggg ttc cga tgg gag ccg gtg gtg gac acc ggc aag gag       2322
Glu Arg Ser Gly Phe Arg Trp Glu Pro Val Val Asp Thr Gly Lys Glu
730                 735                 740                 745 gca cca tat gac ttc ctc acc gat ggc ctg cca gat cgt gct gtc acc       2370
Ala Pro Tyr Asp Phe Leu Thr Asp Gly Leu Pro Asp Arg Ala Val Thr
                750                 755                 760 gtc tac cag ttc tct cat ttc ctc aac tcc aat ctc tat cct atg ctc       2418
Val Tyr Gln Phe Ser His Phe Leu Asn Ser Asn Leu Tyr Pro Met Leu
            765                 770                 775 agc tac tcc tcc atc atc ctt gta ttg cgc cct gat gtctgaaaga           2464
Ser Tyr Ser Ser Ile Ile Leu Val Leu Arg Pro Asp
        780                 785 agcagataca atagagtata ctatagcggt tgttctctag gctgtagcat gcagtggaaa     2524
ctggaaaatg ttggggttgc tctgttgtcg gtagtttaca tgcgcatgtc ggtatgtgta     2584
cataaagctg gtggatctca gttctcagat cggactcgag acggcaaaac cattgccagt     2644
tggctggttc tctgaagttt tgtttggtgt aaagaaatgg tggtccatca tctactcttt     2704
tttttttttt t                                                          2715

<210> SEQ ID NO 2
<211> LENGTH: 789
<212> TYPE: PRT
<213> ORGANISM: Zea mays

<400> SEQUENCE: 2

Met Ala Gln Ser Ser Ser Pro Ala Ser Arg Arg Ala Arg Cys Ser
1               5                   10                  15

Pro Cys Pro Arg Ala Gly Gly Ala Pro Ala Cys Gly Ala Gly Pro Met
                20                  25                  30

Trp Arg Asp Trp Gly Gly Gly Cys Leu Ser Thr Pro Pro Arg
            35                  40                  45

Gly Pro Trp Pro Arg Arg Cys Arg Arg Arg Thr Thr Thr Thr
        50                  55                  60

Thr Arg Arg Trp Pro Arg Glu Arg Phe Ala Leu Gly Gly Ala Cys Arg
65                  70                  75                  80

Val Leu Ala Gly Met Pro Ala Pro Leu Gly Ala Thr Ala Leu Arg Gly
                85                  90                  95
```

-continued

Gly Val Asn Phe Ala Val Tyr Ser Ser Gly Ala Ser Ala Ser Leu
             100                 105                 110

Ser Leu Phe Ala Pro Gly Asp Leu Lys Ala Asp Arg Val Thr Glu Glu
         115                 120                 125

Val Pro Leu Asp Pro Leu Leu Asn Arg Thr Gly Asn Val Trp His Val
    130                 135                 140

Phe Ile His Gly Asp Glu Leu His Gly Met Leu Cys Gly Tyr Arg Phe
145                 150                 155                 160

Asp Gly Val Phe Ala Pro Glu Arg Gly Gln Tyr Tyr Asp Val Ser Asn
             165                 170                 175

Val Val Val Asp Pro Tyr Ala Lys Ala Val Val Ser Arg Gly Glu Tyr
             180                 185                 190

Gly Val Pro Ala Pro Gly Gly Ser Cys Trp Pro Gln Met Ala Gly Met
             195                 200                 205

Ile Pro Leu Pro Tyr Asn Lys Phe Asp Trp Gln Gly Asp Leu Pro Leu
    210                 215                 220

Gly Tyr His Gln Lys Asp Leu Val Ile Tyr Glu Met His Leu Arg Gly
225                 230                 235                 240

Phe Thr Lys His Asn Ser Ser Lys Thr Lys His Pro Gly Thr Tyr Ile
             245                 250                 255

Gly Ala Val Ser Lys Leu Asp His Leu Lys Glu Leu Gly Val Asn Cys
             260                 265                 270

Ile Glu Leu Met Pro Cys His Glu Phe Asn Glu Leu Glu Tyr Phe Ser
    275                 280                 285

Ser Ser Ser Lys Met Asn Phe Trp Gly Tyr Ser Thr Ile Asn Phe Phe
    290                 295                 300

Ser Pro Met Ala Arg Tyr Ser Ser Gly Ile Arg Asp Ser Gly Cys
305                 310                 315                 320

Gly Ala Ile Asn Glu Phe Lys Ala Phe Val Arg Glu Ala His Lys Arg
             325                 330                 335

Gly Ile Glu Val Ile Met Asp Val Val Phe Asn His Thr Ala Glu Gly
             340                 345                 350

Asn Glu Lys Gly Pro Ile Leu Ser Phe Arg Gly Ile Asp Asn Ser Thr
             355                 360                 365

Tyr Tyr Met Leu Ala Pro Lys Gly Glu Phe Tyr Asn Tyr Ser Gly Cys
    370                 375                 380

Gly Asn Thr Phe Asn Cys Asn His Pro Val Val Arg Glu Phe Ile Val
385                 390                 395                 400

Asp Cys Leu Arg Tyr Trp Val Thr Glu Met His Val Asp Gly Phe Arg
             405                 410                 415

Phe Asp Leu Ala Ser Ile Leu Thr Arg Gly Cys Ser Leu Trp Asp Pro
             420                 425                 430

Val Asn Val Tyr Gly Ser Pro Met Glu Gly Asp Met Ile Thr Thr Gly
             435                 440                 445

Thr Pro Leu Val Ala Pro Pro Leu Ile Asp Met Ile Ser Asn Asp Pro
    450                 455                 460

Ile Leu Gly Asn Val Lys Leu Ile Ala Glu Ala Trp Asp Ala Gly Gly
465                 470                 475                 480

Leu Tyr Gln Glu Gly Gln Phe Pro His Trp Asn Val Trp Ser Glu Trp
             485                 490                 495

Asn Gly Lys Tyr Arg Asp Thr Val Arg Gln Phe Ile Lys Gly Thr Asp
             500                 505                 510

```
Gly Phe Ala Gly Ala Phe Ala Glu Cys Leu Cys Gly Ser Pro Gln Leu
        515                 520                 525

Tyr Gln Ala Gly Gly Arg Lys Pro Trp His Ser Ile Gly Phe Val Cys
530                 535                 540

Ala His Asp Gly Phe Thr Leu Ala Asp Leu Val Thr Tyr Asn Ser Lys
545                 550                 555                 560

Tyr Asn Leu Ser Asn Gly Glu Asp Phe Arg Asp Gly Glu Asn His Asn
                565                 570                 575

Leu Ser Trp Asn Cys Gly Glu Gly Glu Phe Ala Ser Leu Ser Val
            580                 585                 590

Arg Arg Leu Arg Lys Arg Gln Met Arg Asn Phe Phe Val Cys Leu Met
        595                 600                 605

Val Ser Gln Gly Val Pro Met Phe Tyr Met Gly Asp Glu Tyr Gly His
610                 615                 620

Thr Lys Gly Gly Asn Asn Asn Thr Tyr Cys His Asp His Tyr Val Asn
625                 630                 635                 640

Tyr Phe Arg Trp Asp Lys Lys Glu Glu Gln Ser Ser Asp Leu Tyr Arg
                645                 650                 655

Phe Cys Arg Leu Met Thr Glu Phe Arg Lys Glu Cys Glu Ser Leu Gly
            660                 665                 670

Leu Glu Asp Phe Pro Thr Ser Glu Arg Leu Lys Trp His Gly His Gln
        675                 680                 685

Pro Gly Lys Pro Asp Trp Ser Glu Ala Ser Arg Phe Val Ala Phe Thr
690                 695                 700

Met Lys Asp Glu Thr Lys Gly Glu Ile Tyr Val Ala Phe Asn Thr Ser
705                 710                 715                 720

His Leu Pro Val Val Gly Leu Pro Glu Arg Ser Gly Phe Arg Trp
                725                 730                 735

Glu Pro Val Val Asp Thr Gly Lys Glu Ala Pro Tyr Asp Phe Leu Thr
            740                 745                 750

Asp Gly Leu Pro Asp Arg Ala Val Thr Val Tyr Gln Phe Ser His Phe
        755                 760                 765

Leu Asn Ser Asn Leu Tyr Pro Met Leu Ser Tyr Ser Ser Ile Ile Leu
770                 775                 780

Val Leu Arg Pro Asp
785

<210> SEQ ID NO 3
<211> LENGTH: 11779
<212> TYPE: DNA
<213> ORGANISM: Zea mays

<400> SEQUENCE: 3
caccgaacta tcatatatat aggtctgcat gatattgatg gttgcaatgt agtggtaaaa      60
caggtagatt aaaataacaa aatgtatatg tatagcccag gatcaccaat gaattacaaa    120
atcttttttc ataacaatat aacacattta tataagtt atcatgatat taatatgttc      180
ccattgcaac gcacgggaac taacctagta attaattaat ttattacctc ctttcgacga    240
accagccggc accaaaagat ggatcaccgt gcacggagcg tgcgtccgtt gcgggaaacg    300
acggggatct aggcgacgcc gtgacggtga tgctcccgtt cacgtttcgc ggctttcgct    360
gcaccccttt gattcacggt ggccccacag aaaagcccat gtccacgggg cccactcccg    420
ggtccggaca cgcgccgagg gagagggggct cccagatttt ctagggactg ctaccttctt    480
tttttagata aataatagac caaaatccgg ttttagggca tgtttggttc cctacctaac    540
```

```
ttgccacact ttgcctaact tttctgccta aggttagttc ttcaatttga acgactaacc    600
ttaggcaaag tgtggcgtat ttagccacga accaaacagg cccttactat ttcgagggta    660
agcgcaaatt cacataactt aaaaaaaaat ctaaaacatc tcacaaaaca taacaaaatt    720
ataagtctag aagacttaat aactcccctc ctcatcagcg actcaaactc actttaaaaa    780
acggctcatt acaactcaat cctatttaaa aacctccaac cctgataagc aaaaaactgc    840
gtggccacca acttcagata acgacagact ttaattaaaa gatcagctgc ttcttcactt    900
ttctgtagct gcgtctagag tctgagccaa tgagttcctc caaataaaac ctgcaaataa    960
gtcaacatat gtactttgtt aaatattaat tcatttctac ttattcaaat agcacagcac   1020
atgctgagac accataataa tcaaattctt agtatttaga tccatctcat caaccaactc   1080
caaagatatg tttgacagtt cttagtattt agggactgct gccgagtacg ttccttcaga   1140
tcctctttgg ttcttccttt tctattttat ttatattgtc actttactag accatagtaa   1200
gagagaattc tcttttgagt taattaacca cccacaccgt acaaattgag caagcctttg   1260
ttatctccac atacatgtat attaatataa gatacatata tctcgttttt taaagaaata   1320
tcgcattggg tttattatta ttttaagact agtttgtaaa ctctattttt ctgagaaatt   1380 cctattttc aagagaaaat aaactaattt atttgaaaaa atgtaaaact tttgataaaa    1440
taggattgtc aaactagacc ttattatatg tatatgtata tgtataaagt atcactgtga   1500
aaagtatgaa aaaagtttag ttcttttctt ttggtgaata taagagtata aataataaaa   1560
agtggaatag tatagtgcct gaaaagcggc aactagatcg tgtttgccag tacgcgggcc   1620
ccacagaaaa agcccacgtc cgcctcccgc tgcgaaaaaa cgacacgggc cgagtggacg   1680
acggtggccg gacgcagacg cagacgcttc cggctgtgaa aaaacgcacg ctccgacccc   1740
gccgtccgcc gatccgaggc tccggcccca ctctgtcagc gtcactgcgt gagcgagcgg   1800
gcgggtgcgt gatccggacc cgcccctcct cacaccgtcg cgcacgggag ccaagacgac   1860
gccgcgctcc gtcgcatcca cctcgtctcg tcacacactc cactcgaacg cactacttga   1920
tcggccaaag ccaaacgaac tgggctccct ccctccact tcctctcccc atggcgcagc    1980
agctcccctg cgtctcgtcg ccgcgcccgc tgctcgccgt gcccgcgggc cggtggcgcg   2040
ccggcgtgcg gggccggccc aatgtggcgg gactggggcg ggggcggctg tctctccacg   2100
ccgccgccgc gcggcccgtg gccgaggcgg tgcaggcgga ggaggacgac gacgacgacg   2160
acgaggaggt ggccgaggag aggttcgcgc tgggcggcgc gtgccgggtg ctcgcgggaa   2220
tgcccgcgcc gctcggcgcc accgcgctcc gcggcggtgt caacttcgcc gtctactcca   2280
gcggtgcctc cgccgcgtcg ctgtgcctct tcgctcccgg cgacctcaag gcggtgagca   2340
tcccccaccc ctagtctttg atgaatgcaa tttctgcaac cggtgctcgg atccttctgt   2400
gtcgttcttc ttctcttttg gaatttgaat ggaagggaag tcggcttact aacttactcc   2460
tctatttctc tctctctcga ataacttgct tctcgatgct gtacgctaat tgttggcttc   2520
atacgatacg ccggtgctga aatggactga gttctctgta ttcctggtat gatgcaggat   2580
agggtgaccg aggaggtgcc cctcgatccc ctgctcaacc gaacgggaaa cgtgtggcac   2640
gtgttcatcc acgggaccag gctgcacggc atgctctacg atacaggtt cgatggcgtg    2700 ttcgcccctg agcgcggaca gtactacgat gtgtccaacg ttgtggtgga tccatacgct   2760
aaggtgacgg gctgttgtct ttactttggc tatgcgtgtg agctgtgaca cactcagaaa   2820
ctgattgctg ggtgcttgct catgttttag ttgtttactt cttcttgttg ttgttttctc   2880
taggcaggca gtggtaagcc gaggtgaata tggtgtgcct gcgcctggtg gtagttgttg   2940
```

```
gcctcaaatg gctggtatga tccctcttcc ctataataag gtaagccaga actactctcg   3000
ctcacactac cttcctgttt gctttcatgc tgtatccttc tcttccagtt ttatgatctc   3060
cccatgtctg actcactcac gattaaacaa taaaaagaaa ccaccgcata tatttggctc   3120
attgatgcat ttgaaaagct ccgcatgaac taactgaaca aagcgcctag atatcaactg   3180
taggttagga ctcattggct tctgcttact tagtttctgc tttgccaggt tcaaatggag   3240
tcgaagttat atttcacgtg ctattcatgt tgtcttgtta tttcatttcg tatgataagg   3300
ttttgcattt gcagtttgat tggcaaggtg acctacccct tgggtaccat cagaaggacc   3360
ttgtcatata tgaaatgcat ttgcgtggat tcacaaagca caactcaagc aagacaaaac   3420
acccaggaac ttacattggt gctgtgtcaa agcttgacca tctaaaggta ctgttacgaa   3480
cagactagct ataagtctgc gaaagtgtcc tcatgcattt gtttaggttt tgcaactatg   3540
ccaagtaatg ctgccctagt ctattagttc ataggcataa acacagattt tactttgtgc   3600
ttacataaat gtttttgctc agtaaacttg tcagtggtat tggtcgtctt agacttttg    3660 gcatgtgttt gttgttggaa tataatataa gtgaattgtc aaccttctcc tatcagctta   3720
agcttttgga tagaaagaat tggttggtgc atgtaactta atatggtatt aaagacagag   3780
gtcatgaatt cgaatcctga ctagcacaat taaataaaac ccaaaagctt aagcttatag   3840
gaagagatgg ataattcact tatattatat tctaacattt atgactaaac tctttgtttg   3900
acctgcataa actcccttca caggaacttg gagtgaactg tatagagcta atgccctgcc   3960
atgagttcaa tgagctagag tacttcagct cctcttcgaa gtatgtggat ttggattaca   4020
gtatatagat gccatcagtt ttataggact ctggaactga tatcttttg tttcattgag    4080 catgatcgta tatgaccttt tcgttctatt ttccatgata tttcccccat ttccagattt   4140
gctagtgtga tctccaattt tgtgccttac ccttatagct tgatcacaac tgacttatat   4200
tcatatattg acacattatt tcatataatt gttcatcctt gtgccaggat gaacttctgg   4260
ggatattcca caataaattt tttctcacca atggcaagat attcttcaag tggcataaga   4320
gactctggat gtggtgccat aaatgaattt aaagcttttg taagggaggc ccacaaacgg   4380
ggaattgagg taaccaagcc aatttaagtt aatggctgaa tgctaaccga aataagagct   4440
tccttatatc atttttgaca tggagatatg tcactattag gtgatcatgg atgttgtctt   4500
caatcataca gctgaaggta atgagaaagg cccaatatta tcctttaggg ggatagataa   4560
tagtacatac tacatgcttg cacctaaggt gagatacatt attcatcttg taatcgttct   4620
ttcatggacc acaaagtatt tatgtattcc atttcataga ttcacgtcta tataacaagc   4680
tatttgaaga gcatttattt gtgcagggag agttttataa ttattctggt tgtggaaata   4740
ccttcaattg taatcatcct gtagtccgtg aatttatagt ggattgcttg aggtacaaat   4800
ctgtatataa cttctgttaa attgctccta atttccttct gccgcttgtc attctattgg   4860
atgatgcaag ttttttgaggg atggatagca atgtttatgc tttgctgcct gaatatataa   4920 gcatttttaaa tttctagtat tcaaacaaaa caaagaaaca gttttctttt aattgatatt   4980
tcgtcattga ctatcagtgt ttaagctata tatttgttaa gataaattgt ttatgcacta   5040
atatttgagt ttgatgttgc agatactggg taacagaaat gcatgttgat ggttttcgtt   5100
ttgaccttgc atctatactg accagaggat gcagtaaaa tgttattctt atttctcct    5160 tattttgtct ttttaggcat tcttaagcca accttttcctt taccagtcta tgggatccag   5220
ttaatgtgta tggaagtcca atggaaggtg acatgattac gacagggaca cctcttgttg   5280
ccccaccact tattgacatg attagcaatg acccaattct tggaaatgtc aaggtagctg   5340
```

-continued

```
ttatatttta tacttatgtt ttattttttt tctccaaaag cgcaggagaa ctgcgccccg    5400
ttatatatta agaaaagaga aacaaaggtc tatagaagac ccagatacaa gactctcctt    5460
acggaggcca gaaacaagca tacaaaaaac tgtccataaa gacactaacc ctcccaacat    5520
ctgcccctaa gcattaggaa gcggagccaa ctacattcgg ggccctagcc aggtctagtg    5580
agcctagatt tttagctcca gccataaccc aacatacaag ttcatctaag aagcttctct    5640
gtagtcttgc tagtgaagga gattccacat tgaagattac tttgttgcgg tgaagccata    5700
cacaccacgc ccccagaatg atgacactgt tgagcccccct ttttcctact tttgtgccct    5760
ctaataacca gacgtctcca ccactccgcg aaagaggttc atcaacagca ggagtaaggt    5820
ggcccaagct gaaaggagat aaaatactga accaaaattg acgggtaaag atgcatgagg    5880
ttaggaggta ctgaattgtt tccagttgtt gatcacataa ggagcaagca tctgatgtg    5940 gcaaacctct cttttctaac ctgtcagcgg tccaacacct attcctcata gccaaccaca    6000
ggaagaattt gcatttcgga ggagcccatg tcttccaaag ccttttccat ggctcaaagg    6060
tggttgaacc tgagaataag attttttcaac aagatttaga cgagaaattc cctgagatct    6120
cattcctcca cctgtgctga tcaggaactt gggataattc aaccccctca ctgaatccca    6180
taacagcagg tactgctgca gcccagccag cgagagaggt gctttaatat ccctaaccca    6240
ctgccaattt tcaagggctc gagccacagt tcttgaatat agaaatcttt tgcccacctt    6300
agctaccacc tcagggcaa atccctgat cgcagcccca tttagccatc tatcagtcca    6360
gaaaagagtg ctggtgccat tcccaaccat agaaatcaga gaatctgaaa acagattctt    6420
gacatgctgc tgtataggaa gcttcagtcc ctgccaaggc ctgtttgggt ccattttttt    6480
ccaaccataa ccattttgat tgaaaagccc agctcatgaa ttgcagatta gggatttccc    6540
aagcccccca agatcaatag gccttgtaac aatatctcaa gaaaccagac agctgcctcc    6600
attagcctct ttccttctct tccaaataaa ccccttcta attttgtcta tagctttaat    6660
catccaattg gatattcatt gcaataagaa gatagactgg gatagccgaa ggcacatatc    6720
gcacaagagc tattctacca gcaaggttaa gaagatgtgc tttccaattt gcaataagaa    6780
ggttatttgg ttgattatga ttcttaatac ttatgttta tcatctgcac taactgaaga    6840
ttcaaagcca ttttgtggtt ttggatacgt gtacacatgc tatgtaacta atctcagtta    6900
ccatgtgctt gatgcttttg ggtaatatat gaacctgatt ggctgttaaa tatgcagaac    6960
agtatatata ataatcgact gtatcaacat attgtagttt cttggttttt gttctcacta    7020
cttcctccat tgtatttata gctcattgct gaagcatggg atgcaggagg tctctatcaa    7080
gttggtcagt ttcctcactg gaacgtttgg tcagagtgga atggaaaggt aagatacttt    7140
cagagacttc aaagtctttt tgctacttgg tactttctaa ataacaaatg aagccttgtc    7200
aaatacagaa tgtaagtttc aacagatata tttaaataga tgagtgcttc tatctacctg    7260
tgaattgttg cagggatcta aaactgttta aaattctaat gttagtttct tctagaggca    7320
aatcggtaat ttggtctggt aagtggatac agtttggaat aatggatgga accagaatct    7380
acgttcaggc ccaactatca aacagactca gggctgtttg ggggcaagtt ccagttccag    7440
ttttcaagct tctgaagaag ctggctccaa ggaacctgag cctaggatac ttggatctca    7500
tcattatgtt ttttgttcta gagaagctgg gttcagaaag gccaacactt aggacttccc    7560
agcccaactg tttttatgtg ggttgagcag agaagcccag ctagacagaa aacacaaata    7620
actgcatttg ttggacttat agaatttta aattataaac acaagaatga ttttgagat    7680 atacttcaca ggccaacact taggagtatg tttcaaacaa tagcctcact gacaacatta    7740
```

```
ggtaagtgca tctttgatct ttatcagagc atgatgctga tgaagttttg ataattacca   7800
tatgatcttt tgcatccttc ttcagctaaa ccaacagctt ccaactttt gttctctata    7860
gttgtttcac caaagtacta acttgcttag ttgttttctc agtatcgcga taccgtgcgt   7920
cagttcatca aaggcacaga tggatttgct ggtgcttttg ctgaatgcct atgtggaagt   7980
ccacagttat accaggtaat gtagcataag tacccatcaa tgagcacggt gctacatgac   8040
ctgaacagaa acttttgaag gaactgggtg atagtgttac agataaacag aaataacata   8100
atatgacaat ctagcatata tttcagccta gaagtttaac acaagttcca ttctatgtag   8160
tagtataacc tttaggatcc atctgcaagt gagagatcac attcttttct ttgagtgtct   8220
aatggacctc ttcaagccat tgaaaactcc tactatatat gtattttgtt ggatgagaag   8280
ccgcatgaat aaatactatc ttctgtgaac tgatgaaagc attaacaatg aattgccgaa   8340
tactccatgt attgtatgca attaggtgga ttagtgttta tctacaaata atagtttggt   8400
attgataagt acatgccttt tattatcagg caggggggag gaagccttgg cacagtatca   8460
actttgtatg tgcacacgat ggatttacac tggctgattt ggtcacatac aatagcaagt   8520
acaacttgtc aaatggtgag gacaacagag atggggaaaa tcataatctt agctggaatt   8580
gtggggaggt aatttgaaat ctcatgcttt tatctcttgt aggcttttta tgttagtcaa   8640
atgtctgtca aatgacttgt catagttttc tagccatgag taccaaactg gtttcaccta   8700
aacaggctat atagtttgta cacgtgcatt ccagctaaa tttatgtggc aagtatatac    8760
agatcatctc tatagtgtag cgcactttag agtttcattt gaataatgca ggaaggagaa   8820
tttgcaagtc tgtcagtccg aagattaagg aagaggcaaa tgcgcaattt ctttgtttgt   8880
cttatggttt ctcaggtaag aattagtatc tgatgtttta agtttttat ggattgtgct    8940
ttcaggtccc tgtttgttca gggtagaact caaggttgca tttgcagtca gtggtatgct   9000
ggaatatgca tcattggttc agtccttgag tttagtcact tgatgagggt tactacttgc   9060
taagttgtgt tgaggatctg tgttttccaa aagattatgc catgttgcat tgaatatcca   9120
actagctgta tttgtacctg aagaaacata tttatttaaa caaaaattac tgtaaacatc   9180
atttatttga caaggtttca gtctttccat gcatcctaat ataggggtaa ggttaaagtg   9240
gatctgaagt cacattgtta tttttttgtat tgatctacta ctacctatca attgttttca   9300
ttttctaaat ttttagggag ttccaatgtt ctacatgggc gatgaatatg gtcacacaaa   9360
gggagggaac aacaatacgt actgccatga ccattatgtc agtccgatgc caacacatat   9420
taacacattg ttttaatcaa tttctttgac attcttgtaa tcttctagcc tttattttg    9480
gttgtgcagg tcaactattt ccgttgggat aagaaggaag aacaatcctc tgatttgtac   9540
agattctgcc gtctcatgac caaattccgc aagtaatact cttcccgcca atatttccg    9600
tgctataccg atgatggttc atctgttcac caaatggcga gatctgtaca gtttacgttg   9660
tcatactgtc tattcatgtt cttttggtgt gcaatacagg gaatgtgaat ctcttggcct   9720
tgaggacttc ccgacttcag aacggttgaa atggcacggt catcagcccg ggaagcctga   9780
ctggtcagag gcaagccgat tcgttgcctt caccatggta ctgacataac acctaccacc   9840
atcatcacta gtcatttcaa gaatcatttt tctaccatta gtaatcaga agatcaaaaa    9900
aggagtgctg atggtttcta tgtatctgtt actgcagaag gacgaaacca aaggcgagat   9960
ctacgtggcc ttcaacacca gtcaccttcc ggtggttgtc gggcttccag agcgctctgg  10020
gttccgatgg gagccggtgg tggacaccgg caaggaggca ccatatgact tcctcaccga  10080
tggcctacca gatcgtgctg tcaccgtcta ccagttctct catttcctca actccaatct  10140
```

-continued

```
ctatcctatg ctcagctact cctccatcat ccttgtattg cgccctgatg tctgaaagaa      10200
gcggatacaa tagagtatac tgtagcggtt gttctctagg ctgtagcatg cagtggaaac      10260
tggaaaatgt tggggttgct ctgttgtcgg tagtttacat gcgcatgtcg gtatgtgtag      10320
ctaaagctgg tggatctcag ttctcagatc ggactcgagc cggggaaaac cattgcccgg      10380
ttggctggtt ctctgaagtt gtgtttggtg taaagaaatg gtggtccatc atctactcaa      10440
tttttttctc ttttttttaat gaaataaatt gattcaaaat taactcattc ctcaacttaa     10500
taattagtat atacacgagg aataaattaa ttctatcaaa tttatgaaat gaaatccaac      10560
attattcgaa gaagaatcga caactactaa cacggcactg ctcccggaga aagaggaaaa      10620
cctggcaaat ggattacgat gtgagggtcg ctaaagtaaa gagtacgaca aaactttcat      10680
agcataagct cagaacttac gttgtcatta taggcgatac tgtcctacca actccgccgc      10740
ctgcgctaca aactccaggt atccttggtc atggtcacat accttcgaaa ggtatggagc      10800
attgtaccca cgtaaacaac ccatagtatt tttaaccaaa gtacgttggc aagaacgaag      10860
cacagtacca cacgcttgtc aacagaagac cctttttacc tttctacaca ctctccaaag      10920
gagatccttg taagaggaat cttccttgag ctataaaagg aagggttggt cttctctatt      10980
cagatgaaca cacactccga tccacgcacg cactactcac accagagact tgggacgctt      11040
ccctctctcg cctgcttgca cctcgtacta cgaataattt ggtgttggta gtgtagccac      11100
cgaagactaa gtagggatat tcggccgaac caatataatt ctgcgtccac atcacaaccc      11160
ccgagcctac gcgccctaca aatttattcg tcggtactta ctcaaactcg ccactaaggc      11220
cagggttcga gcccaatatc taacgctccc ataccattgt taggtgtcta ggacattggc      11280
tctgttgggg gcctttctct ttcgaaggtc ctcaaaagtg cgactaacca tttgtttttca     11340 gtatgatata tattattaca ggaagcttca gctttgggat gaaagttctc tcatgataaa      11400
ggcatgtgat atgaatatac aacccgaagg tgacatggat ggacgccaag ctgtggctca      11460
aggagcttca gcttggatgg aagacaaacc gacctaaggg ggaaaagact acttagtcct      11520
tgataacttg tattataact aagagtaaat gccaggggta tgaatgtaat cttatccggg      11580
ctgcatcctg tgcctataaa tagatgaaca gtatcactgt actgttcacg ctggattgta      11640
atctctctct cgcgtcatct ttgcattctc accttctggc gaactgaagg tacattgttt      11700
tataaatatc attaatgtta tcctatttgt aaatatgaat ataattgaat ggttttgttc      11760 tttccccccct tatttgtat                                                  11779
```

<210> SEQ ID NO 4
<211> LENGTH: 450
<212> TYPE: DNA
<213> ORGANISM: Zea mays

<400> SEQUENCE: 4

```
cgtctcgtca cacactccac tcgaacgcac tacttgatcg gccaaagcca aacgaactgg        60
gctccctccc ctccacttcc tctccccatg gcgcagcagc tccctgcgt ctcgtcgccg        120 cgcccgctgc tcgccgtgcc cgcgggccgg tggcgcgccg gcgtgcgggg ccggcccaat       180
gtggcgggac tgggcggggg gcggctgtct ctccacgccg ccgccgcgcg gcccgtggcc       240
gaggcggtgc aggcggagga ggacgacgac gacgacgacg aggaggtggc cgaggagagg       300
ttcgcgctgg gcggcgcgtg ccgggtgctc gcgggaatgc ccgcgccgct cggcgccacc       360
gcgctccgcg gcggtgtcaa cttcgccgtc tactccagcg gtgcctccgc cgcgtcgctg       420
tgcctcttcg ctcccggcga cctcaaggcg                                       450
```

<210> SEQ ID NO 5
<211> LENGTH: 244
<212> TYPE: DNA
<213> ORGANISM: Zea mays

<400> SEQUENCE: 5

| | | |
|---|---|---|
| gtgagcatcc cccaccccta gtctttgatg aatgcaattt ctgcaaccgg tgctcggatc | 60 |
| cttctgtgtc gttcttcttc tcttttggaa tttgaatgga agggaagtcg gcttactaac | 120 |
| ttactcctct atttctctct ctctcgaata acttgcttct cgatgctgta cgctaattgt | 180 |
| tggcttcata cgatacgccg gtgctgaaat ggactgagtt ctctgtattc ctggtatgat | 240 |
| gcag | 244 |

<210> SEQ ID NO 6
<211> LENGTH: 186
<212> TYPE: DNA
<213> ORGANISM: Zea mays

<400> SEQUENCE: 6

| | | |
|---|---|---|
| gatagggtga ccgaggaggt gcccctcgat cccctgctca accgaacggg aaacgtgtgg | 60 |
| cacgtgttca tccacgggga ccagctgcac ggcatgctct acggatacag gttcgatggc | 120 |
| gtgttcgccc tgagcgcgg acagtactac gatgtgtcca cgttgtggt ggatccatac | 180 |
| gctaag | 186 |

<210> SEQ ID NO 7
<211> LENGTH: 124
<212> TYPE: DNA
<213> ORGANISM: Zea mays

<400> SEQUENCE: 7

| | | |
|---|---|---|
| gtgacgggct gttgtcttta ctttggctat gcgtgtgagc tgtgacacac tcagaaactg | 60 |
| attgctgggt gcttgctcat gttttagttg tttacttctt cttgttgttg ttttctctag | 120 |
| gcag | 124 |

<210> SEQ ID NO 8
<211> LENGTH: 93
<212> TYPE: DNA
<213> ORGANISM: Zea mays

<400> SEQUENCE: 8

| | | |
|---|---|---|
| gcagtggtaa gccgaggtga atatggtgtg cctgcgcctg gtggtagttg ttggcctcaa | 60 |
| atggctggta tgatccctct tccctataat aag | 93 |

<210> SEQ ID NO 9
<211> LENGTH: 334
<212> TYPE: DNA
<213> ORGANISM: Zea mays

<400> SEQUENCE: 9

| | | |
|---|---|---|
| gtaagccaga actactctcg ctcacactac cttcctgttt gctttcatgc tgtatccttc | 60 |
| tcttccagtt ttatgatctc cccatgtctg actcactcac gattaaacaa taaaaagaaa | 120 |
| ccaccgcata tatttggctc attgatgcat ttgaaaagct ccgcatgaac taactgaaca | 180 |
| aagcgcctag atatcaactg taggttagga ctcattggct tctgcttact tagtttctgc | 240 |
| tttgccaggt tcaaatggag tcgaagttat atttcacgtg ctattcatgt tgtcttgtta | 300 |
| tttcatttcg tatgataagg gtttgcattt gcag | 334 |

```
<210> SEQ ID NO 10
<211> LENGTH: 153
<212> TYPE: DNA
<213> ORGANISM: Zea mays

<400> SEQUENCE: 10
tttgattggc aaggtgacct acccttggg taccatcaga aggaccttgt catatatgaa      60
atgcatttgc gtggattcac aaagcacaac tcaagcaaga caaaacaccc aggaacttac    120
attggtgctg tgtcaaagct tgaccatcta aag                                 153

<210> SEQ ID NO 11
<211> LENGTH: 456
<212> TYPE: DNA
<213> ORGANISM: Zea mays

<400> SEQUENCE: 11
gtactgttac gaacagacta gctataagtc tgcgaaagtg tcctcatgca tttgtttagg     60
ttttgcaact atgccaagta atgctgccct agtctattag ttcataggca taaacacaga   120
ttttactttg tgcttacata aatgttttg ctcagtaaac ttgtcagtgg tattggtcgt    180
cttagacttt ttggcatgtg tttgttgttg aatataata taagtgaatt gtcaaccttc    240
tcctatcagc ttaagctttt ggatagaaag aattggttgg tgcatgtaac ttaatatggt   300
attaaagaca gaggtcatga attcgaatcc tgactagcac aattaaataa aacccaaaag   360
cttaagctta taggaagaga tggataattc acttatatta tattctaaca tttatgacta   420
aactctttgt ttgacctgca taaactccct tcacag                             456

<210> SEQ ID NO 12
<211> LENGTH: 77
<212> TYPE: DNA
<213> ORGANISM: Zea mays

<400> SEQUENCE: 12
gaacttggag tgaactgtat agagctaatg ccctgccatg agttcaatga gctagagtac     60
ttcagctcct cttcgaa                                                    77

<210> SEQ ID NO 13
<211> LENGTH: 247
<212> TYPE: DNA
<213> ORGANISM: Zea mays

<400> SEQUENCE: 13
gtatgtggat ttggattaca gtatatagat gccatcagtt ttataggact ctggaactga     60 tatcttttg tttcattgag catgatcgta tatgaccttt tcgttctatt tccatgata     120 tttcccccat ttccagattt gctagtgtga tctccaattt tgtgccttac ccttatagct   180
tgatcacaac tgacttatat tcatatattg acacattatt tcatataatt gttcatcctt   240
gtgccag                                                             247

<210> SEQ ID NO 14
<211> LENGTH: 142
<212> TYPE: DNA
<213> ORGANISM: Zea mays
```

```
<400> SEQUENCE: 14
gatgaacttc tggggatatt ccacaataaa ttttttctca ccaatggcaa gatattcttc        60
aagtggcata agagactctg gatgtggtgc cataaatgaa tttaaagctt ttgtaaggga       120
ggcccacaaa cggggaattg ag                                                142

<210> SEQ ID NO 15
<211> LENGTH: 91
<212> TYPE: DNA
<213> ORGANISM: Zea mays

<400> SEQUENCE: 15
gtaaccaagc caatttaagt taatggctga atgctaaccg aaataagagc ttccttatat        60
catttttgac atggagatat gtcactatta g                                       91

<210> SEQ ID NO 16
<211> LENGTH: 108
<212> TYPE: DNA
<213> ORGANISM: Zea mays

<400> SEQUENCE: 16
gtgatcatgg atgttgtctt caatcataca gctgaaggta atgagaaagg cccaatatta        60
tcctttaggg ggatagataa tagtacatac tacatgcttg cacctaag                    108

<210> SEQ ID NO 17
<211> LENGTH: 118
<212> TYPE: DNA
<213> ORGANISM: Zea mays

<400> SEQUENCE: 17
gtgagataca ttattcatct tgtaatcgtt ctttcatgga ccacaaagta tttatgtatt        60
ccatttcata gattcacgtc tatataacaa gctatttgaa gagcatttat ttgtgcag        118

<210> SEQ ID NO 18
<211> LENGTH: 86
<212> TYPE: DNA
<213> ORGANISM: Zea mays

<400> SEQUENCE: 18
ggagagtttt ataattattc tggttgtgga aataccttca attgtaatca tcctgtagtc        60
cgtgaattta tagtggattg cttgag                                             86

<210> SEQ ID NO 19
<211> LENGTH: 270
<212> TYPE: DNA
<213> ORGANISM: Zea mays

<400> SEQUENCE: 19
gtacaaatct gtatataact tctgttaaat tgctcctaat ttccttctgc cgcttgtcat        60
tctattggat gatgcaagtt tttgagggat ggatagcaat gtttatgctt tgctgcctga       120
atatataagc atttttaaatt tctagtattc aaacaaaaca aagaaacaag ttttctttaa      180
ttgatatttc gtcattgact atcagtgttt aagctatata tttgttaaga taaattgttt      240
atgcactaat atttgagttt gatgttgcag                                        270

<210> SEQ ID NO 20
<211> LENGTH: 71
<212> TYPE: DNA
<213> ORGANISM: Zea mays
```

<400> SEQUENCE: 20

```
atactgggta acagaaatgc atgttgatgg ttttcgtttt gaccttgcat ctatactacc    60
agaggatgca g                                                         71
```

<210> SEQ ID NO 21
<211> LENGTH: 72
<212> TYPE: DNA
<213> ORGANISM: Zea mays

<400> SEQUENCE: 21

```
gtaaaatgtt attcttattt tctccttatt ttgtcttttt aggcattctt aagccaacct    60
ttcctttacc ag                                                        72
```

<210> SEQ ID NO 22
<211> LENGTH: 127
<212> TYPE: DNA
<213> ORGANISM: Zea mays

<400> SEQUENCE: 22

```
tctatgggat ccagttaatg tgtatggaag tccaatggaa ggtgacatga ttacgacagg    60
gacacctctt gttgccccac cacttattga catgattagc aatgacccaa ttcttggaaa   120
tgtcaag                                                             127
```

<210> SEQ ID NO 23
<211> LENGTH: 1708
<212> TYPE: DNA
<213> ORGANISM: Zea mays

<400> SEQUENCE: 23

```
gtagctgtta tattttatac ttatgtttta tttttttttct ccaaaagcgc aggagaactg    60
cgccccgtta tatattaaga aaagagaaac aaaggtctat agaagaccca gatacaagac   120
tctccttacg gaggccagaa acaagcatac aaaaaactgt ccataaagac actaaccctc   180
ccaacatctg cccctaagca ttaggaagcg gagccaacta cattcggggc cctagccagg   240
tctagtgagc ctagattttt agctccagcc ataacccaac atacaagttc atctaagaag   300
cttctctgta gtcttgctag tgaaggagat tccacattga agattacttt gttgcggtga   360
agccatacac accacgcccc cagaatgatg acactgttga gccccctttt cctacttttt   420
gtgccctcta ataaccagac gtctccacca ctccgcgaaa gaggttcatc aacagcagga   480
gtaaggtggc ccaagctgaa aggagataaa atactgaacc aaaattgacg ggtaaagatg   540
catgaggtta ggaggtactg aattgtttcc agttgttgat cacataagga gcaagcatct   600
ggatgtggca aacctctctt ttctaacctg tcagcggtcc aacacctatt cctcatagcc   660
aaccacagga agaatttgca tttcggagga gcccatgtct tccaaagcct tttccatggc   720
tcaaaggtgg ttgaacctga gaataagatt tttcaacaag atttagacga gaattccct   780
gagatctcat tcctccacct gtgctgatca ggaacttggg ataattcaac cccctcactg   840
aatcccataa cagcaggtac tgctgcagcc cagccagcga gagaggtgct ttaatatccc   900
taacccactg ccaattttca agggctcgag ccacagttct tgaatataga aatcttttgc   960
ccacttagc taccacctca ggggcaaaat ccctgatcgc agccccattt agccatctat  1020
cagtccagaa aagagtgctg gtgccattcc caaccataga aatcagagaa tctgaaaaca  1080
gattcttgac atgctgctgt ataggaagct tcagtccctg ccaaggcctg tttgggtcca  1140
ttttttttcca accataacca ttttgattga aaagcccagc tcatgaattg cagattaggg  1200
```

-continued

```
atttcccaag ccccccaaga tcaataggcc ttgtaacaat atctcaagaa accagacagc    1260
tgcctccatt agcctctttc cttctcttcc aaataaaccc ccttctaatt ttgtctatag    1320
ctttaatcat ccaattggat attcattgca ataagaagat agactgggat agccgaaggc    1380
acatatcgca caagagctat tctaccagca aggttaagaa gatgtgcttt ccaatttgca    1440
ataagaaggt tatttggttg attatgattc ttaatactta tgttttatca tctgcactaa    1500
ctgaagattc aaagccattt tgtggttttg gatacgtgta cacatgctat gtaactaatc    1560
tcagttacca tgtgcttgat gcttttgggt aatatatgaa cctgattggc tgttaaatat    1620
gcagaacagt atataataa atcgactgta tcaacatatt gtagtttctt ggtttttgtt    1680
ctcactactt cctccattgt atttatag                                      1708
```

<210> SEQ ID NO 24
<211> LENGTH: 87
<212> TYPE: DNA
<213> ORGANISM: Zea mays

<400> SEQUENCE: 24

```
ctcattgctg aagcatggga tgcaggaggt ctctatcaag ttggtcagtt tcctcactgg     60
aacgtttggt cagagtggaa tggaaag                                        87
```

<210> SEQ ID NO 25
<211> LENGTH: 774
<212> TYPE: DNA
<213> ORGANISM: Zea mays

<400> SEQUENCE: 25

```
gtaagatact ttcagagact tcaaagtctt tttgctactt ggtactttct aaataacaaa     60
tgaagccttg tcaaatacag aatgtaagtt tcaacagata tatttaaata gatgagtgct    120
tctatctacc tgtgaattgt tgcagggatc taaaactgtt taaaattcta atgttagttt    180
cttctagagg caaatcggta atttggtctg gtaagtggat acagtttgga ataatggatg    240
gaaccagaat ctacgttcag gcccaactat caaacagact cagggctgtt tgggggcaag    300
ttccagttcc agttttcaag cttctgaaga agctggctcc aaggaacctg agcctaggat    360
acttggatct catcattatg ttttttgttc tagagaagct gggttcagaa aggccaacac    420
ttaggacttc ccagcccaac tgtttttatg tgggttgagc agagaagccc agctagacag    480
aaaacacaaa taactgcatt tgttggactt atagaatttt aaaattataa acacaagaat    540 gattttgag atatacttca caggccaaca cttaggagta tgtttcaaac aatagcctca    600
ctgacaacat taggtaagtg catctttgat ctttatcaga gcatgatgct gatgaagttt    660
tgataattac catatgatct tttgcatcct tcttcagcta aaccaacagc ttccaacttt    720
ttgttctcta tagttgtttc accaaagtac taacttgctt agttgttttc tcag          774
```

<210> SEQ ID NO 26
<211> LENGTH: 93
<212> TYPE: DNA
<213> ORGANISM: Zea mays

<400> SEQUENCE: 26

```
tatcgcgata ccgtgcgtca gttcatcaaa ggcacagatg gatttgctgg tgcttttgct     60
gaatgcctat gtggaagtcc acagttatac cag                                 93
```

<210> SEQ ID NO 27
<211> LENGTH: 434
<212> TYPE: DNA
<213> ORGANISM: Zea mays

<400> SEQUENCE: 27

```
gtaatgtagc ataagtaccc atcaatgagc acggtgctac atgacctgaa cagaaacttt      60
tgaaggaact gggtgatagt gttacagata aacagaaata acataatatg acaatctagc     120
atatatttca gcctagaagt ttaacacaag ttccattcta tgtagtagta taacctttag     180
gatccatctg caagtgagag atcacattct tttctttgag tgtctaatgg acctcttcaa     240
gccattgaaa actcctacta tatatgtatt tgttggatg agaagccgca tgaataaata      300
ctatcttctg tgaactgatg aaagcattaa caatgaattg ccgaatactc catgtattgt     360
atgcaattag gtggattagt gtttatctac aaataatagt ttggtattga taagtacatg     420
ccttttatta tcag                                                       434
```

<210> SEQ ID NO 28
<211> LENGTH: 159
<212> TYPE: DNA
<213> ORGANISM: Zea mays

<400> SEQUENCE: 28

```
gcagggggga ggaagccttg gcacagtatc aactttgtat gtgcacacga tggatttaca      60
ctggctgatt tggtcacata caatagcaag tacaacttgt caaatggtga ggacaacaga     120
gatgggaaa atcataatct tagctggaat tgtggggag                             159
```

<210> SEQ ID NO 29
<211> LENGTH: 223
<212> TYPE: DNA
<213> ORGANISM: Zea mays

<400> SEQUENCE: 29

```
gtaatttgaa atctcatgct tttatctctt gtaggctttt tatgttagtc aaatgtctgt      60
caaatgactt gtcatagttt tctagccatg agtaccaaac tggtttcacc taaacaggct     120
atatagtttg tacacgtgca tttccagcta aatttatgtg gcaagtatat acagatcatc     180
tctatagtgt agcgcacttt agagtttcat ttgaataatg cag                       223
```

<210> SEQ ID NO 30
<211> LENGTH: 84
<212> TYPE: DNA
<213> ORGANISM: Zea mays

<400> SEQUENCE: 30

```
gaaggagaat ttgcaagtct gtcagtccga agattaagga agaggcaaat gcgcaatttc      60
tttgtttgtc ttatggtttc tcag                                            84
```

<210> SEQ ID NO 31
<211> LENGTH: 421
<212> TYPE: DNA
<213> ORGANISM: Zea mays

<400> SEQUENCE: 31

```
gtaagaatta gtatctgatg tttttaagttt tttatggatt gtgctttcag gtccctgttt      60
gttcagggta gaactcaagg ttgcatttgc agtcagtggt atgctggaat atgcatcatt     120
ggttcagtcc ttgagtttag tcacttgatg agggttacta cttgctaagt tgtgttgagg     180
```

```
atctgtgttt tccaaaagat tatgccatgt tgcattgaat atccaactag ctgtatttgt      240
acctgaagaa acatatttat ttaaacaaaa attactgtaa acatcattta tttgacaagg      300
tttcagtctt tccatgcatc ctaatatagg ggtaaggtta aagtggatct gaagtcacat      360
tgttattttt tgtattgatc tactactacc tatcaattgt tttcattttc taaattttta      420
g                                                                     421
```

```
<210> SEQ ID NO 32
<211> LENGTH: 81
<212> TYPE: DNA
<213> ORGANISM: Zea mays

<400> SEQUENCE: 32
ggagttccaa tgttctacat gggcgatgaa tatggtcaca caaagggagg gaacaacaat       60
acgtactgcc atgaccatta t                                                81
```

```
<210> SEQ ID NO 33
<211> LENGTH: 92
<212> TYPE: DNA
<213> ORGANISM: Zea mays

<400> SEQUENCE: 33
gtcagtccga tgccaacaca tattaacaca ttgttttaat caatttcttt gacattcttg       60
taatcttcta gccttttatt ttggttgtgc ag                                    92
```

```
<210> SEQ ID NO 34
<211> LENGTH: 83
<212> TYPE: DNA
<213> ORGANISM: Zea mays

<400> SEQUENCE: 34
gtcaactatt tccgttggga taagaaggaa gaacaatcct ctgatttgta cagattctgc       60
cgtctcatga ccaaattccg caa                                              83
```

```
<210> SEQ ID NO 35
<211> LENGTH: 127
<212> TYPE: DNA
<213> ORGANISM: Zea mays

<400> SEQUENCE: 35
gtaatactct tcccgccaaa tatttccgtg ctataccgat gatggttcat ctgttcacca       60
aatggcgaga tctgtacagt ttacgttgtc atactgtcta ttcatgttct tttggtgtgc      120
aatacag                                                               127
```

```
<210> SEQ ID NO 36
<211> LENGTH: 118
<212> TYPE: DNA
<213> ORGANISM: Zea mays

<400> SEQUENCE: 36
ggaatgtgaa tctcttggcc ttgaggactt cccgacttca gaacggttga atggcacgg        60 tcatcagccc gggaagcctg actggtcaga ggcaagccga ttcgttgcct tcaccatg       118
```

```
<210> SEQ ID NO 37
<211> LENGTH: 120
<212> TYPE: DNA
<213> ORGANISM: Zea mays
```

```
<400> SEQUENCE: 37
gtactgacat aacacctacc accatcatca ctagtcattt caagaatcat ttttctacca      60
ttaagtaatc agaagatcaa aaaggagtg ctgatggttt ctatgtatct gttactgcag     120

<210> SEQ ID NO 38
<211> LENGTH: 501
<212> TYPE: DNA
<213> ORGANISM: Zea mays

<400> SEQUENCE: 38
aaggacgaaa ccaaaggcga gatctacgtg gccttcaaca ccagtcacct tccggtggtt      60
gtcgggcttc cagagcgctc tgggttccga tgggagccgg tggtggacac cggcaaggag     120
gcaccatatg acttcctcac cgatggccta ccagatcgtg ctgtcaccgt ctaccagttc     180
tctcatttcc tcaactccaa tctctatcct atgctcagct actcctccat catccttgta     240
ttgcgccctg atgtctgaaa gaagcggata caatagagta tactgtagcg ttgttctct      300 aggctgtagc atgcagtgga acaggaaaa tgttggggtt gctctgttgt cggtagttta     360
catgcgcatg tcggtatgtg tagctaaagc tggtggatct cagttctcag atcggactcg     420
agccggggaa aaccattgcc cggttggctg gttctctgaa gttgtgtttg gtgtaaagaa     480
atggtggtcc atcatctact c                                              501

<210> SEQ ID NO 39
<211> LENGTH: 772
<212> TYPE: PRT
<213> ORGANISM: Pseudomonas

<400> SEQUENCE: 39

Met Lys Cys Pro Lys Ile Leu Gly Ala Leu Gly Cys Ala Val Leu
  1               5                  10                  15

Ala Gly Val Pro Ala Met Pro Ala His Ala Ala Ile Asn Ser Met Ser
                 20                  25                  30

Leu Gly Ala Ser Tyr Asp Ala Gln Gln Ala Asn Ile Thr Phe Arg Val
             35                  40                  45

Tyr Ser Ser Gln Ala Thr Arg Ile Val Leu Tyr Leu Tyr Ser Ala Gly
         50                  55                  60

Tyr Gly Val Gln Glu Ser Ala Thr Tyr Thr Leu Ser Pro Ala Gly Ser
 65                  70                  75                  80

Gly Val Trp Ala Val Thr Val Pro Val Ser Ser Ile Lys Ala Ala Gly
                 85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Cys Val Ser
            115                 120                 125

Asp Val Asp Ala Asn Gly Asp Arg Phe Asn Pro Asn Lys Leu Leu Leu
            130                 135                 140

Asp Pro Tyr Ala Gln Glu Asx Ser Gln Asp Pro Leu Asn Pro Ser Asn
145                 150                 155                 160

Gln Asn Gly Asn Val Phe Ala Ser Ala His Tyr Arg Thr Thr Asp Ser
                165                 170                 175

Gly Ile Tyr Ala Pro Lys Gly Val Val Leu Val Pro Ser Thr Gln Ser
            180                 185                 190

Thr Gly Thr Lys Pro Thr Arg Ala Gln Lys Asp Asp Val Ile Tyr Glu
            195                 200                 205
```

-continued

```
Val His Val Arg Gly Phe Thr Glu Gln Asp Thr Ser Ile Pro Ala Gln
    210                 215                 220

Tyr Arg Gly Thr Tyr Tyr Gly Ala Gly Leu Lys Ala Ser Tyr Leu Ala
225                 230                 235                 240

Ser Leu Gly Val Thr Ala Val Glu Phe Leu Pro Val Gln Glu Thr Gln
                245                 250                 255

Asn Asp Ala Asn Asp Val Val Pro Asn Ser Asp Ala Asn Gln Asn Tyr
            260                 265                 270

Trp Gly Tyr Met Thr Glu Asn Tyr Phe Ser Pro Asp Arg Arg Tyr Ala
        275                 280                 285

Tyr Asn Lys Ala Ala Gly Gly Pro Thr Ala Glu Phe Gln Ala Met Val
    290                 295                 300

Gln Ala Phe His Asn Ala Gly Ile Lys Val Tyr Met Asp Val Val Tyr
305                 310                 315                 320

Asn His Thr Ala Glu Gly Gly Thr Trp Thr Ser Ser Asp Pro Thr Thr
                325                 330                 335

Ala Thr Ile Tyr Ser Trp Arg Gly Leu Asp Asn Ala Thr Tyr Tyr Glu
            340                 345                 350

Leu Thr Ser Gly Asn Gln Tyr Phe Tyr Asp Asn Thr Gly Ile Gly Ala
        355                 360                 365

Asn Phe Asn Thr Tyr Asn Thr Val Ala Gln Asn Leu Ile Val Asp Ser
    370                 375                 380

Val Ala Tyr Trp Ala Asn Thr Met Gly Val Asp Gly Phe Arg Phe Asp
385                 390                 395                 400

Leu Ala Ser Val Leu Gly Asn Ser Cys Leu Asn Ala Val His Ala Ser
                405                 410                 415

Ala Pro Asn Cys Pro Asn Gly Gly Tyr Asn Phe Asp Ala Ala Asp Ser
            420                 425                 430

Asn Val Ala Ile Asn Arg Ile Leu Arg Glu Phe Thr Val Arg Pro Ala
        435                 440                 445

Ala Gly Gly Thr Val Trp Ile Cys Leu Arg Asn Leu Gly Pro Ser Ala
    450                 455                 460

Ala Thr Arg Thr Ser Trp Val Asp Ser Arg Arg Val Val Arg Val Glu
465                 470                 475                 480

Trp Ser Val Pro Arg Gln Leu Arg Gln Ala Gln Asn Glu Leu Gly Ser
                485                 490                 495

Met Thr Ile Tyr Val Thr Gln Asp Ala Asn Asp Phe Ser Gly Ser Ser
            500                 505                 510

Asn Leu Phe Gln Ser Ser Gly Arg Ser Pro Trp Asn Ser Ile Asn Phe
        515                 520                 525

Ile Asp Val His Asp Gly Met Thr Leu Lys Asp Val Tyr Ser Cys Asn
    530                 535                 540

Gly Ala Asn Asn Ser Gln Ala Ser Tyr Gly Pro Ser Asp Gly Gly Thr
545                 550                 555                 560

Ser Thr Asn Tyr Ser Trp Asp Gln Gly Met Ser Ala Gly Thr Gly Ala
                565                 570                 575

Ala Val Asp Gln Arg Arg Ala Ala Arg Thr Gly Met Ala Phe Glu Met
            580                 585                 590

Leu Ser Ala Gly Thr Pro Leu Met Gln Gly Gly Asp Glu Tyr Leu Arg
        595                 600                 605
```

-continued

```
Thr Leu Gln Cys Asn Asn Ala Tyr Asn Leu Asp Ser Ser Ala Asn
    610                 615                 620

Trp Leu Thr Tyr Ser Trp Thr Thr Asp Gln Ser Asn Phe Tyr Thr Phe
625                 630                 635                 640

Ala Gln Arg Leu Ile Arg Ser Ala Arg His Ile Pro Leu Arg Pro Ser
                645                 650                 655

Ser Trp Tyr Ser Gly Ser Gln Leu Thr Trp Tyr Gln Pro Ser Gly Ala
            660                 665                 670

Val Ala Asp Ser Asn Tyr Trp Asn Asn Thr Ser Asn Tyr Ala Ile Ala
        675                 680                 685

Tyr Ala Ile Asn Gly Pro Ser Leu Gly Asp Ser Asn Asp Ser Ile Tyr
    690                 695                 700

Val Ala Tyr Asn Gly Trp Ser Ser Val Thr Phe Thr Leu Pro Ala
705                 710                 715                 720

Pro Pro Ser Gly Thr Gln Trp Tyr Arg Val Thr Asp Thr Cys Asp Trp
                725                 730                 735

Asn Asp Gly Ala Ser Thr Phe Val Ala Pro Gly Ser Glu Thr Leu Ile
            740                 745                 750

Gly Gly Ala Gly Thr Thr Tyr Gly Gln Cys Gly Gln Ser Leu Leu Leu
        755                 760                 765

Leu Ile Ser Lys
    770

<210> SEQ ID NO 40
<211> LENGTH: 20
<212> TYPE: DNA
<213> ORGANISM: Zea mays

<400> SEQUENCE: 40
gtatgtacta ttatctatcc                                              20

<210> SEQ ID NO 41
<211> LENGTH: 21
<212> TYPE: DNA
<213> ORGANISM: Zea mays

<400> SEQUENCE: 41
gggatcatac cagccatttg a                                            21

<210> SEQ ID NO 42
<211> LENGTH: 15
<212> TYPE: DNA
<213> ORGANISM: Zea mays

<400> SEQUENCE: 42
ggctgtcgcg tgcgt                                                   15

<210> SEQ ID NO 43
<211> LENGTH: 15
<212> TYPE: DNA
<213> ORGANISM: Zea mays

<400> SEQUENCE: 43
gcgtacgtct ctaaa                                                   15
```